US011931380B2

(12) United States Patent
Albelda et al.

(10) Patent No.: US 11,931,380 B2
(45) Date of Patent: *Mar. 19, 2024

(54) INHIBITION OF DIACYLGLYCEROL KINASE TO AUGMENT ADOPTIVE T CELL TRANSFER

(71) Applicant: THE TRUSTEES OF THE UNIVERSITY OF PENNSYLVANIA, Philadelphia, PA (US)

(72) Inventors: Steven M. Albelda, Philadelphia, PA (US); Liang-Chuan Wang, Philadelphia, PA (US); Gary Koretzky, Thorton, PA (US); Matthew Riese, Mequon, WI (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 71 days.

This patent is subject to a terminal disclaimer.

(21) Appl. No.: 17/230,791

(22) Filed: Apr. 14, 2021

(65) Prior Publication Data

US 2021/0236553 A1    Aug. 5, 2021

Related U.S. Application Data

(60) Division of application No. 15/908,388, filed on Feb. 28, 2018, now abandoned, which is a continuation of application No. 14/425,452, filed as application No. PCT/US2013/057991 on Sep. 4, 2013, now Pat. No. 9,937,205.

(60) Provisional application No. 61/696,599, filed on Sep. 4, 2012.

(51) Int. Cl.
| | | |
|---|---|---|
| A61K 35/17 | (2015.01) | |
| C07K 2/00 | (2006.01) | |
| C07K 16/30 | (2006.01) | |
| C07K 16/40 | (2006.01) | |
| C12N 5/0783 | (2010.01) | |
| C12N 9/16 | (2006.01) | |
| C12N 15/113 | (2010.01) | |
| A61K 38/00 | (2006.01) | |
| A61K 38/45 | (2006.01) | |

(52) U.S. Cl.
CPC .......... *A61K 35/17* (2013.01); *C07K 2/00* (2013.01); *C07K 16/30* (2013.01); *C07K 16/40* (2013.01); *C12N 5/0638* (2013.01); *C12N 9/16* (2013.01); *C12N 15/1137* (2013.01); *A61K 38/00* (2013.01); *A61K 38/45* (2013.01); *C12N 2310/11* (2013.01); *C12N 2310/14* (2013.01); *C12N 2310/531* (2013.01); *C12Y 207/01107* (2013.01)

(58) Field of Classification Search
CPC ........ A61K 35/17; A61K 38/00; A61K 38/45; C07K 16/30; C07K 16/40; C12N 15/1137; C12N 2310/11; C12N 2310/14; C12N 2310/531
See application file for complete search history.

(56) References Cited

U.S. PATENT DOCUMENTS

| | | |
|---|---|---|
| 4,683,202 A | 7/1987 | Mullis |
| 5,023,243 A | 6/1991 | Tullis et al. |
| 5,168,053 A | 12/1992 | Altman et al. |
| 5,190,931 A | 3/1993 | Inouye et al. |
| 5,350,674 A | 9/1994 | Boenisch et al. |
| 5,356,802 A | 10/1994 | Chandrasegaran |
| 5,399,346 A | 3/1995 | Anderson et al. |
| 5,436,150 A | 7/1995 | Chandrasegaran |
| 5,487,994 A | 1/1996 | Chandrasegaran |
| 5,580,859 A | 12/1996 | Felgner et al. |
| 5,585,362 A | 12/1996 | Wilson et al. |
| 5,589,466 A | 12/1996 | Felgner et al. |
| 5,789,538 A | 8/1998 | Rebar et al. |
| 5,858,358 A | 1/1999 | June et al. |
| 5,883,223 A | 3/1999 | Gray |
| 5,925,523 A | 7/1999 | Dove et al. |
| 5,928,906 A | 7/1999 | Koester et al. |
| 6,007,988 A | 12/1999 | Choo et al. |
| 6,013,453 A | 1/2000 | Choo et al. |
| 6,140,466 A | 10/2000 | Barbas et al. |

(Continued)

FOREIGN PATENT DOCUMENTS

| | | |
|---|---|---|
| WO | 8909622 A1 | 10/1989 |
| WO | 9207065 A1 | 4/1992 |

(Continued)

OTHER PUBLICATIONS

PCT International Search Report and Written Opinion for PCT International Application No. PCT/US2013/057991 dated Jan. 3, 2014.

(Continued)

*Primary Examiner* — J. E. Angell
(74) *Attorney, Agent, or Firm* — Saul Ewing LLP; Kathryn Doyle

(57) ABSTRACT

The present invention provides compositions and methods for inhibiting one or more diacylglycerol kinase (DGK) isoform in a cell in order to enhance the cytolytic activity of the cell. In one embodiment, the cells may be used in adoptive T cell transfer. For example, in some embodiments, the cell is modified to express a chimeric antigen receptor (CAR). Inhibition of DGK in T cells used in adoptive T cell transfer increases cytolytic activity of the T cells and thus may be used in the treatment of a variety of conditions, including cancer, infection, and immune disorders.

4 Claims, 30 Drawing Sheets

(56) References Cited

U.S. PATENT DOCUMENTS

| | | | |
|---|---|---|---|
| 6,200,759 B1 | 3/2001 | Dove et al. | |
| 6,242,568 B1 | 6/2001 | Barbas et al. | |
| 6,326,193 B1 | 12/2001 | Liu et al. | |
| 6,352,694 B1 | 3/2002 | June et al. | |
| 6,410,248 B1 | 6/2002 | Greisman et al. | |
| 6,453,242 B1 | 9/2002 | Eisenberg et al. | |
| 6,534,055 B1 | 3/2003 | June et al. | |
| 6,534,261 B1 | 3/2003 | Cox et al. | |
| 6,607,882 B1 | 8/2003 | Cox et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 7,381,401 B2 | 6/2008 | Gajewski et al. | |
| 9,937,205 B2 * | 4/2018 | Albelda | A61K 35/17 |
| 2004/0101519 A1 | 5/2004 | June et al. | |
| 2005/0266510 A1 | 12/2005 | Gajewski et al. | |
| 2006/0034810 A1 | 2/2006 | Riley et al. | |
| 2006/0121005 A1 | 6/2006 | Berenson et al. | |

FOREIGN PATENT DOCUMENTS

| | | |
|---|---|---|
| WO | 9321319 A1 | 10/1993 |
| WO | 9837186 A1 | 8/1998 |
| WO | 9853057 A1 | 11/1998 |
| WO | 0027878 A1 | 5/2000 |
| WO | 0129058 A1 | 4/2001 |
| WO | 0188197 A2 | 11/2001 |
| WO | 0196584 A2 | 12/2001 |
| WO | 02077227 A2 | 10/2002 |
| WO | 2007014275 A2 | 2/2007 |

OTHER PUBLICATIONS

Ahmadzadeh , et al., "Tumor antigen-specific CD8 T cells infiltrating the tumor express high levels of PD-1 and are functionally impaired", Blood 114, 2009, 1537-1544.

An , et al., "Optimization and functional effects of stable short hairpin RNA expression in primary human lymphocytes via lentiviral vectors", Mol. Ther. 14, 2006, 494-504.

Bedi , et al., "Inhibition of TGF-β enhances the in vivo antitumor efficacy of EGF receptor-targeted therapy", Mol Cancer Ther 11, 2012, 2429-2439.

Beerli , et al., "Engineering polydactyl zinc-finger transcription factors", Nat. Biotechnol. 20, 2002, 135-141 (abstract only).

Belfort , et al., "Homing endonucleases: keeping the house in order", Nucleic Acids Res. 25, 1997, 3379-3388.

Bennett , et al., "Help for cytotoxic-T-cell responses is mediated by CD40 signalling", Nature 393, 1998, 478-480 (abstract only).

Berg , et al., "Selective expansion of a peripheral blood CD8+ memory T cell subset expressing both granzyme B and L-selectin during primary viral infection in renal allograft recipients", Transplant Proc. 30(8), 1998, 3975-3977.

Biocca , et al., "Expressing Intracellular Single-Chain Fv Fragments in Mammalian Cells", Springer Lab Manuals, 1995, 755-774 (abstract only).

Bird , et al., "Single-chain antigen-binding proteins", Science 242, 1988, 423-426.

Bollard , et al., "Adapting a transforming growth factor beta-related tumor protection strategy to enhance antitumor Immunity", Blood 99, 2002, 3179-3187.

Bronte , et al., "Boosting antitumor responses of T lymphocytes infiltrating human prostate cancers", J. Exp. Med. 201, 2005, 1257-1268.

Cai , et al., "A melanoma-specific VH antibody cloned from a fusion phage library of a vaccinated melanoma patient", Proc. Natl. Acad. Sci. USA. 93, 1996, 6280-6285.

Carpenito , et al., "Control of large, established tumor xenografts with genetically retargeted human T cells containing CD28 and CD137 domains.", Proc. Natl. Acad. Sci. U.S.A. 106:, 2009, 3360-3365.

Cartellieri , et al., "Chimeric antigen receptor-engineered T cells for immunotherapy of cancer", J Biomed Biotechnol 2010, 1992, 956304.

Cech , "Ribozymes and their medical implications", J. Amer. Med. Assn. 260, 1988, 3030-3034 (abstract).

Cech , et al., "RNA catalysis by a group I ribozyme. Developing a model for transition state stabilization", J. Biol. Chem. 267, 1992, 17479-17482.

Chambers , et al., "Secondary but not primary T cell responses are enhanced in CTLA-4-deficient CD8+ T cells", Eur J Immunol 28, 1998, 3137-3143 (abstract only).

Chen , et al., "Combined intra- and extracellular immunization against human immunodeficiency virus type 1 infection with a human anti-gp120 antibody", Proc Natl Acad Sci, USA 91, 1994, 5932-5936.

Chen , et al., "Intracellular antibodies as a new class of therapeutic molecules for gene therapy", Human Gene Therapy 5, 1994, 595-601 (abstract).

Chen , et al., "Transforming growth factor beta blocks Tec kinase phosphorylation, Ca2+ influx, and NFATc translocation causing inhibition of T cell differentiation", J Exp Med 197, 2003, 1689-1699.

Chiang , et al., "Ablation of Cbl-b provides protection against transplanted and spontaneous tumors", J Clin Invest 117, 2007, 1029-1036.

Chmielewski M , et al., "IL-12 release by engineered T cells expressing chimeric antigen receptors can effectively Muster an antigen-independent macrophage response on tumor cells that have shut down tumor antigen expression", Cancer Res. Sep. 1, 2011;71(17), 2011, 5697-5706.

Choo , et al., "Advances in zinc finger engineering", Curr. Opin. Struct. Biol. 10, 2000, 411-416.

Chowdhury , et al., "Improving Antibody Infinity by Mimicking Somatic Hypermutation in Vitro", Nat Biotechnol. 17(6), 1999, 568-572.

Cougot , et al., "Cap-tabolism", Trends in Biochem. Sci. 29, 2001, 436-444 (abstract only).

Das , et al., "Digital signaling and hysteresis characterize ras activation in lymphoid cells", Cell 136, 2009, 337-351.

Delong , et al., "Use of cyclooxygenase-2 inhibition to enhance the efficacy of immunotherapy", Cancer Res. 63, 2003, 7845-7852.

Di Bari , et al., "TGF-beta modulates the functionality of tumor-infiltrating CD8+ T cells through effects on TCR signaling and Spred1 expression", Cancer Immunol Immunother. 58, 2009, 1809-1818.

Dower , et al., "RasGRP is essential for mouse thymocyte differentiation and TCR signaling", Nat Immunol. 1, 2000, 317-321 (abstract only).

Doyon , et al., "Heritable targeted gene disruption in zebrafish using designed zinc-finger nucleases", Nat. Biotechnol. 26, 2008, 702-708.

Duan , et al., "Molecular and virological effects of intracellular anti-Rev single-chain variable fragments on the expression of various human immunodeficiency virus-1 strains", Human Gene Therapy 5, 1994, 1315-1324.

Eastham , et al., "Transforming growth factor-beta 1: comparative immunohistochemical localization in human primary and metastatic prostate cancer", Lab Invest. 73, 1995, 628-635 (abstract only).

Elango , et al., "Optimized transfection of mRNA transcribed from a d(A/T) 100 tail-containing vector", Biochim. Biophys. Res. Commun. 330, 2005, 958-966 (abstract only).

Eshhar , "Adoptive cancer immunotherapy using genetically engineered designer T-cells: First steps into the clinic", Curr. Opin. Mol. Ther. 12, 2010, 55-63 (abstract only).

Flavell , et al., "The polarization of immune cells in the tumour environment by TGFbeta", Nat Rev Immunol. 10, 2001, 3900-3907.

(56) References Cited

OTHER PUBLICATIONS

Gajewski, et al., "Absence of CTLA-4 lowers the activation threshold of primed CD8+ TCR-transgenic T cells: lack of correlation with Src homology domain 2-containing protein tyrosine phosphatase", J Immunol. 166, 2001, 3900-3907.

Garland, et al., "The use of Teflon cell culture bags to expand functionally active CD8+ cytotoxic T lymphocytes", Journal of Immunological Methods 227, 1999, 53-63.

Gorelik, et al., "Immune-mediated eradication of tumors through the blockade of transforming growth factor-beta signaling in T cells", Nat Med. 7, 2001, 1118-1122 (abstract only).

Haanen, et al., "Selective Expansion of Cross-reactive CD8+ Memory T Cells by Viral Variants", J. Exp. Med. 190(9), 1999, 1319-1328.

Hampel, et al., "RNA catalytic properties of the minimum (−)sTRSV sequence", Biochemistry 28, 1988, 585-591.

Hasselhoff, et al., "Simple RNA enzymes with new and highly specific endoribonuclease activities", Nature 334, 1988, 585-591.

Houston, et al., "Protein engineering of antibody binding sites: recovery of specific activity in an anti-digoxin single-chain Fv analogue produced in *Escherichia coli*", Proc. Natl. Acad. Sci. USA 85, 1988, 5879-5883.

Huse, et al., "Generation of a large combinatorial library of the immunoglobulin repertoire in phage lambda", Science 246, 1989, 1275-1281 (Abstract).

Isalan, et al., "A rapid, generally applicable method to engineer zinc fingers illustrated by targeting the HIV-1 promoter", Nat. Biotechnol. 19, 2001, 656-660 (abstract only).

Janicki, et al., "Loss of CTL function among high-avidity tumor-specific CD8+ T cells following tumor infiltration", Cancer Res. 68, 2008, 2993-3000.

Jena, et al., "Redirecting T-cell specificity by introducing a tumor-specific chimeric antigen receptor.", Blood, 116:, 2010, 1035-1044.

Jensen, et al., "Antitransgene Rejection Responses Contribute to Attenuated Persistence of Adoptively Transferred CD20/CD19-Specific Chimeric Antigen Receptor Redirected T Cells in Humans", Biol Blood Marrow Transplant 16:, 2010, 1245-1256.

Jespers, et al., "Crystal structure of HEL4, a soluble, refoldable human V(H) single domain with a germ-line scaffold", J. Mol. Biol. 337, 2004, 893-903 (abstract only).

Jordan, et al., "Functional hierarchy of the N-terminal tyrosines of SLP-76", J Immunol. 176, 2006, 2430-2438.

\* cited by examiner

INHIBITION OF DIACYLGLYCEROL KINASE TO AUGMENT ADOPTIVE T CELL TRANSFER

CROSS-REFERENCE TO RELATED APPLICATIONS

This application is a divisional of, and claims priority to, U.S. patent application Ser. No. 15/908,388, filed Feb. 28, 2018, which is a continuation of, and claims priority to, U.S. patent application Ser. No. 14/425,452, filed Mar. 3, 2015, now U.S. Pat. No. 9,937,205, which is the U.S. national phase application filed under 35 U.S.C. § 371 claiming benefit to International Patent Application No. PCT/US2013/057991 filed on Sep. 4, 2013, which is entitled to priority under 35 U.S.C. § 119(e) to U.S. Provisional Patent Application 61/696,599, filed Sep. 4, 2012, each of which is hereby incorporated by reference in its entirety herein.

STATEMENT REGARDING FEDERALLY SPONSORED RESEARCH OR DEVELOPMENT

This invention was made with government support under RO1AI058019 and P01 CA66726, awarded by the National Institutes of Health (NIH). The government has certain rights in the invention.

BACKGROUND OF THE INVENTION

Elicitation of T-cell effector responses requires signal transduction through the T-cell antigen receptor (TCR), a protein complex that binds antigenic peptide presented by MHC, as well as through costimulatory receptors such as CD28. The effector responses generated from TCR signal transduction differ across individual T-cell subsets that are classified according to the expression of cell surface molecules (Smith-Garvin et al., 2009, Annu Rev Immunol 27:591-619). Expression of the surface molecule CD8, for instance, identifies a subset of T cells that respond to antigenic peptides presented in the binding groove of MHC class I. $CD8^+$ T cells are responsible for the recognition and elimination of cells that express antigens derived from intracellular pathogens, such as viruses and intracellular bacteria, and also mutated or embryonic proteins generated by cells that have undergone malignant transformation. Although the extent to which $CD8^+$ T cells are capable of controlling the development and progression of tumorigenesis remains uncertain, it is clear that deficiency of these cells increases the potential for the development of malignancy and that enhanced function of these $CD8^+$ T cells can impart robust antitumor responses in both animal model systems and patients (Turcotte & Rosenberg, 2011, Adv Surg 45:341-60; June, 2007, J Clin Invest 117:1466-76). It is also clear in a number of models that although there may be an initial, potent $CD8^+$ T-cell response, this response is often insufficient to fully protect from tumors (Schreiber et al., 2011, Science 331:1565-70). Mechanisms underlying this failure include (i) the lack of specific antigens with sufficient avidity for the TCR expressed by tumors, (ii) the absence of costimulatory ligands expressed by antigen-presenting cells (APC) within tumor-draining lymph nodes, and (iii) direct suppression of T-cell responses within the tumor microenvironment mediated by inhibitory secreted factors such as TGFβ, prostaglandin E (PGE)-2, or adenosine, as well as inhibitory cells, such as regulatory T cells (Quezada et al., 2011, Immunol Rev 241:104-18).

The potential for effective responses by $CD8^+$ T cells in some instances of incurable malignancies, such as metastatic melanoma, has led to significant interest in defining ways to manipulate these cells to generate more potent responses as well as responses against a more diverse array of tumors. One promising approach has focused on engineering T cells to express chimeric antigen receptors (CAR). CARs are transmembrane fusion proteins that consist of an extracellular antibody domain capable of binding to a specific tumor antigen coupled to intracellular signaling domains from TCR and costimulatory components (Milone et al., 2009, Mol Ther 17:1453-64). In principle, CARs provide several advantages over the endogenous receptors of T cells. First, the engineered ligand-binding segment of CARs arises from an antibody, obviating the need for MHC presentation. Second, the antibody-binding component of the CAR can be chosen to be both specific and highly sensitive to antigens expressed selectively by tumor cells, increasing avidity of the T cell-tumor interaction and minimizing the potential for destruction of normal "bystander" host cells. Third, engagement of the CAR by ligand stimulates both TCR and costimulatory signaling modules, eliminating a requirement for expression of costimulatory ligands by tumor-draining APCs. CAR-expressing T cells that come into contact with tumor cells expressing the antigen of interest have been shown to develop functional responses that lead to tumor cell lysis and cytokine production.

There has been considerable success in the use of CARs in animal models (Milone et al., 2009, Mol Ther 17:1453-64; Dower et al., 2000, Nat Immunol 1:317-21), and recently, CAR-expressing T cells have been shown to be effective in patients to treat refractory chronic lymphocytic leukemias (CLL) (Chiang et al., 2007, J Clin Invest 117:1029-36; Loeser et al., 2007, J Exp Med 204:879-91). Although T cells engineered to express CARs are capable of overcoming some limitations of the endogenous immune system to combat tumors (e.g., CARs are not MHC restricted and hence will lyse tumor cells that have down-regulated MHC expression), CAR-expressing T cells still lack intrinsic programming to overcome, perhaps, the most important component that limits $CD8^+$ T-cell antitumor responses: the inhibitory tumor microenvironment.

However, there are a number of areas that appear to be important potential limitations to the success of CARs, especially for solid tumors. A major limitation is the loss of efficacy of the infused T cells. As reported by others (Ahmadzadeh et al., 2009, Blood 114:1537-1544; Whiteside, 2004, Cancer Immunol. Immunother. 53:865-878; Zippelius et al., 2004, Cancer Res. 64:2865-2873; Bronte et al., 2005, J. Exp. Med. 201:1257-1268; Prinz et al., 2012, J. Immunol. 188:5990-6000; Monu et al., 2007, Cancer Res. 67:11447-11454; Janicki et al., 2008, Cancer Res. 68:2993-3000), even when the T cells successfully traffic into tumors, in many instances, they appear to be inactivated within tumors rather rapidly. The mechanisms are not fully understood, but probably involve secreted immune-inhibitory factors such as TGFβ, PGE2, and adenosine within the tumor microenvironment, interactions with inhibitory leukocytes (i.e. T-regulatory cells and myeloid suppressor cells) and/or contact with inhibitory molecules on the surface of tumor cells.

The mechanisms of T cell inactivation are not well understood, especially in CARs, where, unlike native T cells, the signal transduction mechanisms have not been well studied. Thus, there is a need in the art to develop compositions and methods for enhancing T cell activation and killing ability during adoptive T cell transfer. The present invention satisfies this unmet need.

SUMMARY OF THE INVENTION

The present invention provides a composition for enhancing the cytolytic activity of a cell. In one embodiment, the composition comprises an inhibitor of diacylglycerol kinase (DGK) or a downstream effector protein thereof.

In one embodiment, the inhibitor is selected from the group consisting of a small interfering RNA (siRNA), short hairpin RNA (shRNA), an antisense nucleic acid, a ribozyme, a dominant negative mutant, an antibody, a peptide, a zinc finger nuclease, and a small molecule.

In one embodiment, the cell is a T cell.

In one embodiment, the T cell is an activated T cell.

In one embodiment, the T cell is modified to express a chimeric antigen receptor (CAR).

In one embodiment, the composition inhibits the DGK isoform selected from the group consisting of DGKα and DGKζ.

In one embodiment, the composition inhibits both DGKα and DGKζ.

The invention provides an isolated cell having enhanced cytolytic activity, wherein the cell comprises an inhibitor of DGK or a downstream effector protein thereof.

The invention also provides a method of enhancing the cytolytic activity of a cell. In one embodiment, the method comprises administering to the cell an effective amount of a composition comprising an inhibitor of DGK or a downstream effector protein thereof.

In one embodiment, the inhibitor is selected from the group consisting of a small interfering RNA (siRNA), short hairpin RNA (shRNA), an antisense nucleic acid, a ribozyme, a dominant negative mutant, an antibody, a peptide, a zinc finger nuclease, and a small molecule.

In one embodiment, the cell is a T cell.

In one embodiment, the T cell is an activated T cell.

In one embodiment, the T cell is modified to express a chimeric antigen receptor (CAR).

In one embodiment, the composition inhibits the DGK isoform selected from the group consisting of DGKα and DGKζ.

In one embodiment, the composition inhibits both DGKα and DGKζ.

In one embodiment, the cell is genetically modified to express the inhibitor.

In one embodiment, administering the inhibitor comprises administering the inhibitor in an ex vivo environment.

The invention also provides a method of enhancing adoptive T cell transfer in a subject. In one embodiment, the method comprises administering to a T cell an effective amount of a composition comprising an inhibitor of DGK or a downstream effector protein thereof, wherein the T cell is administered to the subject during adoptive T cell transfer.

In one embodiment, the T cell is an activated T cell.

In one embodiment, the T cell is an autologous T cell.

In one embodiment, the T cell is modified to express a chimeric antigen receptor (CAR).

In one embodiment, the composition inhibits the DGK isoform selected from the group consisting of DGKα and DGKζ.

In one embodiment, the composition inhibits both DGKα and DGKζ.

In one embodiment, the cell is genetically modified to express the inhibitor.

In one embodiment, administering the inhibitor comprises administering the inhibitor in an ex vivo environment.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 8A-8B, depicts how the elimination of DGK resulted in T cells less sensitive to TGFβ-mediated-inhibition of tumor killing. FIG. 8A is a graph depicting how DGKα knockout cells are resistant to the inhibitory effects of TGFβ in a killing assay. FIG. 8B is a graph depicting how DGKα knockout cells are resistant to the inhibitory effects of TGFβ in an INFγ release assay.

FIG. 16A through FIG. 16D, depicts the results of experiments demonstrating that DGKζ-deficient activated CD8+ T cells show enhanced tumor responses in vivo. FIG. 16A: Twenty thousand naïve ($CD44^{lo}$) CD8+ wild-type (wt) or DGKζ-deficient OT-I cells were injected intravenously into congenically marked (CD90.1) mice. Twenty-four hours later, the mice were injected intravenously with 5,000 cfu Listeria-ova, and one week later, mice were euthanized, and the presence of donor OT-I T cells (CD90.2$^+$, ova tetramer+) was assessed (n=5, quantitation of 1 of 3 representative experiments is shown). CD90.2$^+$ cells from FIG. 16A were isolated magnetically and 1×10$^6$ cells were injected intravenously into CD45.1$^+$ mice bearing 2-week-old subcutaneous EL4-ova tumors. One week later, mice were euthanized and assessed for tumor size (FIG. 16B), persistence of donor (CD45.2$^+$, ova tetramer+) T cells (FIG. 16C), and tumor-infiltrating donor T cells (FIG. 16D). "No T cell" mice did not receive donor T cells, and CD45.2 cells were not detected in any organ tissue (FIG. 16B, data from 3 pooled experiments. FIG. 16C and FIG. 16D, data from 1 of 3 representative experiments, n=5 in each group).

FIG. 17A through FIG. 17C, depicts the results of experiments demonstrating enhanced CAR effector function in DGKζ-deficient CD8$^+$ T cells. CD8$^+$ wild-type (wt) or DGKζ-deficient OT-I T cells were isolated and transduced with mesoCAR retrovirus expressing gfp from an internal ribosomal entry site. FIG. 17A: Cells were evaluated for expression of gfp, CD44 as a marker of activation, and ovalbumin tetramer to assess TCR expression. B and C, mesoCAR-transduced wt or DGKζ-deficient OT-I cells were incubated with 5,000 AE17 ovalbumin cells or AE17 cells expressing both mesothelin and ovalbumin at a ratio of 40:1 in a 96-well plate for 24 hours, and the presence of IFNγ (FIG. 17B) or luciferase (cytotoxicity; FIG. 17C) in cell supernatants was assessed. Calculated estimates of cytotoxicity were confirmed by visual evaluation of cell culture wells. One of the 3 representative experiments is shown; each well was carried out in triplicate. (FIG. 17B and FIG. 17C, P<0.0001 between DGK/AE17ova and wt/AE17ova or DGK/AE17ovameso and wt AE17ovameso. FIG. 17B, P=0.0327 between DGK/AE17ova and DGK/AE17ovameso, P=0.002 between wt/AE17ova and wt/AE17ovameso. FIG. 17C, P<0.0001 between DGK/AE17ova and DGK/AE17ovameso, P=0.007 between wt/AE17ova and wt/AE17ovameso).

FIG. 18A through FIG. 18C, depicts the results of experiments demonstrating that deletion of both T-cell DGK isoforms significantly enhances CAR-T cell effector functions. T cells were isolated from wt, dgkα−/−, dgkζ−/−, or DKO mice, transduced with meso-CAR, and assessed for IFNγ production (FIG. 18A) and cytotoxicity of target cells (FIG. 18B and FIG. 18C) at indicated ratios as described in FIG. 17. In FIG. 18C, a ratio of 40:1 was used for experimental (AE17ovameso) or control (AE17ova) cell lines. One of the 3 representative experiments is shown; each data point was conducted in triplicate (P for all mesoCAR-expressing constructs <0.0001 for AE17ova and AE17ovameso).

FIG. 19A through FIG. 19C, depicts the results of experiments demonstrating enhanced CAR signaling in DGK-deficient CD8$^+$ T cells. FIG. 19A: A total of 1×10$^6$ CAR-transduced (MesoCAR) or vector control (MIGR) CD8$^+$ T cells were incubated with 4×10$^6$ albumin-coated beads (alb) or mesothelin-coated beads (meso or M) or 2.5 μg/mL α-CD3 (α-CD3ε or a) for the indicated times and assessed for phosphorylated (α-pERK) or total Erk (α-ERK) by immunoblotting. FIG. 19B: Levels of pERK, total ERK, and actin were assessed after stimulation of 1×10$^6$ wild-type (wt) or dgkα−/−dgkζ−/− (double knockout; DKO) CD8$^+$ CAR-T cells with 4×10$^6$ mesothelin-coated beads (M) and 2.5 μg/mL α-CD3 (a) for 15 minutes. Each immunoblot analysis is a representative experiment from at least 3 independent iterations. FIG. 19C: A total of 1×10$^6$ wt or DKO-deficient CD8$^+$ CAR T cells were incubated with 4×10$^6$ beads coated with albumin (alb) or mesothelin (meso) for 5 hours and surface expression of CD69 was assessed by flow cytometry.

FIG. 20A through FIG. 20C, depicts the results of experiments demonstrating that DGK-deficient mesoCAR-transduced T cells control mesothelioma in vivo. FIG. 20A: A total of 1×10$^6$ TC1 meso cells were coinjected subcutaneously with 2×10$^5$ wild-type (wt) mesoCAR-transduced T cells or mesoCAR-transduced T cells lacking one or both (DKO) of the indicated DGK. Ten days later, mice were euthanized and tumors were measured. One of the 2 representative experiments (n=4-5) is shown. P of wt versus DKO mesoCAR T cells is 0.05. FIG. 20B: A total of 2×10$^6$ AE17meso cells were injected into flanks of C57Bl/6 mice. One week later, 1×10$^7$ CAR-transduced T cells of indicated genotype were injected intravenously into mice and tumors were measured at indicated time points (n=5 in each genotype, P for DKO CAR-T cells versus wt CAR-T cells=0.0141 at day 10 posttransfer). FIG. 20C: Alternatively, mice were sacrificed 3 and 6 days after T-cell transfer of indicated genotypes as in FIG. 20B and the presence of mesoCAR T cells in tumor (top) or spleen (bottom) was determined [n=3 in each group, 1 of 2 representative experiments. P=0.0082 (tumor) and 0.0461 (spleen) at day 6; day 3 results did not differ significantly].

FIG. 21A and FIG. 21B, depicts the results of experiments demonstrating that DGK inhibitors enhance the cytotoxic capacity of impaired human meso-CAR-transduced T cells. FIG. 21A: MesoCAR-transduced primary human cells were left unexposed or exposed to a human tumor line that does not express mesothelin (EM) or expresses high levels of mesothelin (EM-meso) for 96 hours. A total of 10$^5$ T cells were then isolated and recultured with 5×10$^3$ luciferase-expressing EM-meso cells for 18 hours in the absence or presence of DGK inhibitors R59022 (DGK1 Inhibitor) or R59949 (DGK2 inhibitor) and cell death of target cells was assessed by luciferase release (data from triplicate wells of one of the 3 representative experiments are shown. P of EM-meso exposed T cells to EM exposed T cells=0.004 in no inhibitor group. P of EM-meso-exposed T cells in the absence of inhibitor to DGK1 inhibitor=0.006 or DGK2 inhibitor=0.003). FIG. 20B: Lysis of 5×10$^3$ EM-meso cells was assessed during incubation with no T cells or 10$^5$ untransduced or mesoCAR-transduced primary human T cell for 18 hours in the presence or absence of the indicated concentration of TGFβ (data from triplicate wells of one of the 3 representative experiments. P of mesoCAR T cells between 0 and 10 μg/mL=0.05, 0 and 100 μg/mL=0.025, and 0 and 1000 μg/mL=0.017).

FIG. 22A and FIG. 22B, depicts the results of experiments demonstrating that DGK-deficient T cells are less inhibited by TGFβ. A total of 1×10$^5$ naïve (CD44) mesoCAR-transduced T cells of the indicated genotype were incubated with 5,000 AE17meso target cells at a ratio of 40:1 in the absence or presence of TGFβ at the indicated concentration. IFNγ (FIG. 22A) and cytotoxicity (FIG. 22B) of target cells at 24 hours was assessed as described in FIG. 17. One of the 3 representative experiments is shown. Each data point was conducted in triplicate [P<0.0001 between wild-type (wt) and all DGK-deficient T cells treated with TGFβ].

FIG. 23A and FIG. 23B, depicts the results of experiments demonstrating that MesoCAR-transduced DGKζ-deficient T cells demonstrate resistance to multiple inhibitory stimuli. MesoCAR transduced wt or DGKζ-deficient T cells were incubated with AE17meso target cells for 24 hours at a ratio of 40:1 in the presence or absence of indicated concentrations of (FIG. 23A) adenosine or (FIG. 23B) prostaglandin E2 (PGE2) and cytotoxicity or IFNg production of target cells was assessed as in FIG. 17.

FIG. 24A and FIG. 24B, depicts the results of experiments demonstrating that enhanced expression of FasL and TRAIL in DGKζ-deficient mesoCAR T cells. $2 \times 10^6$ MesoCAR T cells replete (wt) for or lacking the indicated isoform of DGKs were stimulated with $2 \times 10^6$ mesothelin-coated beads for 18 hours in presence of IL2. FasL (FIG. 24A) and TRAIL (FIG. 24B) expression was determined by flow cytometry. One of two experimental iterations is shown, both experiments yielded similar data.

FIG. 25A and FIG. 25B, depicts the results of experiments demonstrating similar expression of Granzyme B and perforin in DGK-deficient mesoCAR T cells. Under conditions identical to FIG. 24, wt or DGK-deficient mesoCAR T cells were incubated with mesothelin-coated beads and the expression of perforin (FIG. 25A) and granzyme B (FIG. 25B) was determined by flow cytometry using an intracellular staining protocol recommended by the manufacturer.

DETAILED DESCRIPTION

Figure 1:
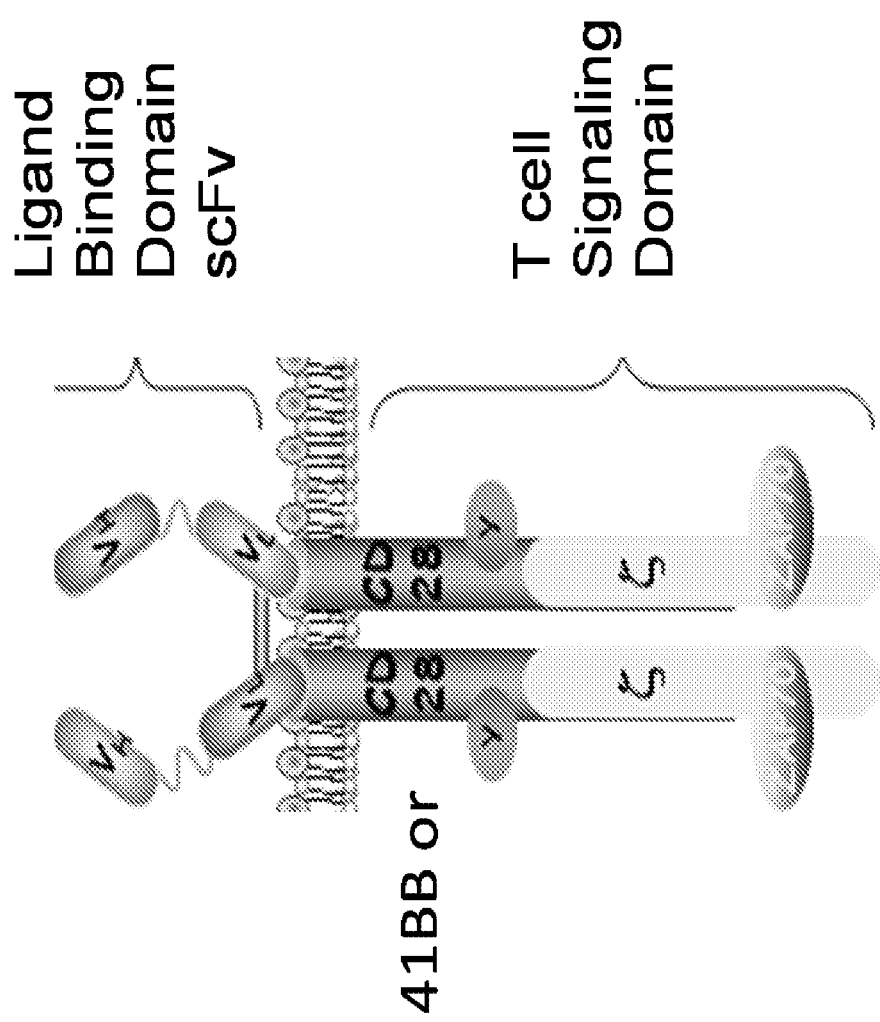
FIG. 1 is an illustration depicting a chimeric antigen receptor (CAR) construct.

The present invention provides compositions and methods for regulating Diacylglycerol Kinase (DGK) in a cell, preferably a T cell. The invention is based upon the discovery that blockade of DGK isoforms enhances the cytolytic activity and persistence of T cells. In one embodiment, the invention provides inhibition of one or more DGK isoform in a T cell in order to augment adoptive T cell transfer.

Accordingly, the present invention provides compositions and methods for inhibiting one or more DGK isoform for augmenting cytolytic activity in a cell. In one embodiment, inhibiting one or more DGK isoform enhances cytolytic activity in T cell modified to express a desired protein (e.g., a chimeric antigen receptor (CAR)). That is, the invention is based on the discovery that inhibition of DGK enhances tumor killing activity of CAR modified T cells. However, the invention should not be limited to only T cells expressing a CAR. Rather, the invention includes any T cell, genetically modified or not, expressing a gene of interest for adoptive T cell transfer.

In one embodiment, the present invention provides methods for treating a wide variety of conditions by inhibiting one or more DGK isoform during adoptive T cell transfer. In one embodiment, T cells are genetically modified ex vivo to express at least one inhibitor. The present methods are useful for treating any condition where adoptive T cell transfer is used. Exemplary conditions for which the present method can be used to treat include various types of cancers, HIV, Hepatitis C, immune disorders, bacterial infections, viral infections, and the like.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. An antibody of the invention includes intracellularly expressed antibody, or intrabody. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies, human antibodies, and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')$_2$, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

"Antisense" refers particularly to the nucleic acid sequence of the non-coding strand of a double stranded DNA molecule encoding a polypeptide, or to a sequence which is substantially homologous to the non-coding strand. As defined herein, an antisense sequence is complementary to the sequence of a double stranded DNA molecule encoding a polypeptide. It is not necessary that the antisense sequence be complementary solely to the coding portion of the coding strand of the DNA molecule. The antisense sequence may be complementary to regulatory sequences specified on the coding strand of a DNA molecule encoding a polypeptide, which regulatory sequences control expression of the coding sequences.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body.

Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "heterologous" as used herein is defined as DNA or RNA sequences or proteins that are derived from the different species.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron (s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types.

"Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). Examples of subjects include humans, dogs, cats, mice, rats, and transgenic species thereof.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides compositions and methods for modulating Diacylgylceral Kinase (DGK) activity in a cell, preferably a T cell. The invention also provides compounds and methods of modulating downstream targets of DGK and its functional equivalents. In one embodiment, the invention is used to augment adoptive T cell transfer in the treatment of a wide variety of conditions, including, but not limited to cancer, infections, and immune disorders.

The present invention is based on the discovery that removal or blockade of DGK isoforms enhances the efficacy of T cells used in adoptive T cell transfer. In certain embodiments, the T cell is an activated T cell. In one embodiment, the T cells used in adoptive T cell transfer are modified to express a desired protein (e.g., a chimeric antigen receptor (CAR)). However, the invention should not be limited to only T cells expressing a CAR. Rather, the invention includes any T cell, genetically modified or not, expressing a gene of interest for adoptive T cell transfer.

In one embodiment, T cells are genetically modified ex vivo to express an inhibitor of one or more DGK isoforms. An advantage of a genetic approach to DGK inhibition is that the effects will be isolated only to the transfused T cells, thus minimizing systemic toxicity and enhancing safety. For example, T cells can be modified to by introducing specific inhibitors of DGK including but not limited to, a siRNA, shRNA, a microRNA, an antisense nucleic acid, a ribozyme, a dominant negative mutant, an intracellular antibody, a peptide, a zinc finger nuclease, and a small molecule. It is described herein, that expression of such an inhibitor will augment tumor killing efficacy.

The present invention provides methods for treating a variety of conditions including, but not limited to, cancer, infection, and immune disorders. In one embodiment, inhibition of one or more DGK isoforms enhances T cell cytolytic activity, thereby reducing the size and growth of a tumor. In one embodiment, the methods comprise inhibiting one or more DGK isoform in a T cell directed to target a specific antigen. In one embodiment, the methods comprise inhibiting one or more DGK isoform in a T cell genetically modified to express a CAR. In one embodiment, the CAR directs the modified T cell to a specific tumor antigen. The methods of the present invention augment CAR T cell therapy by enhancing the cytolytic activity of the CAR modified T cells.

In one embodiment, inhibiting DGK in a T cell results in T cells that are less capable of "turning-off" DAG-mediated signaling within T cells whereby the DGK inhibited T cells are less sensitive to inhibition of tumor killing mediated by inhibitor signals in the tumor microenvironment. For example, the present invention is partly based upon the discovery that PGE2, adenosine, and TGFβ were less able to suppress effector functions in T cells that lacked one or both T-cell isoforms of DGK. The resistance to the inhibitory effects of PGE2, adenosine, and TGFβ is an important factor in a therapeutic context since tumors make large amounts of these inhibitors of tumor killing.

Compositions

The invention is based partly on the discovery that inhibition of DGK activity or expression improves the cytolytic activity of T cells, for example T cells genetically modified to express a chimeric antigen receptor (CAR). However, the invention should not be limited to only T cells expressing a CAR. Rather, the invention includes any T cell, genetically modified or not, expressing a gene of interest for adoptive T cell transfer. As such, the data presented herein indicates that therapeutic inhibition of DGK and/or its down-stream effector proteins may be beneficial, in addition to other effects, by providing sustained targeted lysis of unwanted cells (i.e. tumor cells).

The present invention relates to the discovery that inhibition of any one or more DGK isoform in a cell, preferably a T cell, provides a therapeutic benefit. Thus, the invention comprises compositions and methods for modulating any of these proteins in a T cell thereby enhancing cytolytic activity of the T cell.

The present invention includes a generic concept for inhibiting one or more DGK isoform or any component of the signal transduction pathway associated with the phosphorylation of diacyglycerol (DAG), thereby increasing the cytolytic activity of the T cell. In one embodiment, the composition of the invention inhibits DGKα. In one embodiment, the composition of the invention inhibits DGKζ.

In one embodiment, the invention comprises a composition for enhancing the cytolytic activity of a T cell. In certain embodiments, the T cell is an activated T cell. In one embodiment, the T cell is a genetically modified T cell. In one embodiment the T cell is modified to express a CAR. The composition comprises an inhibitor of any one or more DGK isoforms. In one embodiment, the DGK inhibitor of the invention includes any one or more compositions disclosed in U.S. Patent Application Publication No. 20050266510, the entire content of which is incorporated herein by reference. In another embodiment, the composition comprising the DGK inhibitor is selected from the group consisting of a small interfering RNA (siRNA), a short hairpin RNA (shRNA), a microRNA, an antisense nucleic acid, a ribozyme, a dominant negative mutant, an intracellular antibody, a peptide, a zinc finger nuclease, and a small molecule. However, the invention should not be limited these types of inhibitors. Rather, any type of inhibitor known in the art or to be identified can be used to inhibit DGK. For example, techniques recently published to knock down RNA or delete genes include Transcription activator-like effector nucleases (TALENs) and CRISPR technology (Pennisi, 2013 Science 341: 833).

In one embodiment, the DGK inhibitor of the invention is an interfering RNA which reduces translation of at least one DGK isoform. An interfering RNA can include a siRNA, a shRNA, and a microRNA. An siRNA polynucleotide is an RNA nucleic acid molecule that interferes with RNA activity that is generally considered to occur via a post-transcriptional gene silencing mechanism. An siRNA polynucleotide preferably comprises a double-stranded RNA (dsRNA) but is not intended to be so limited and may comprise a single-stranded RNA (see, e.g., Martinez et al., 2002 Cell 110:563-74). The siRNA polynucleotide included in the invention may comprise other naturally occurring, recombinant, or synthetic single-stranded or double-stranded polymers of nucleotides (ribonucleotides or deoxyribonucleotides or a combination of both) and/or nucleotide analogues as provided herein (e.g., an oligonucleotide or polynucleotide or the like, typically in 5' to 3' phosphodiester linkage). Accordingly it will be appreciated that certain exemplary sequences disclosed herein as DNA sequences capable of directing the transcription of the siRNA polynucleotides are also intended to describe the corresponding RNA sequences and their complements, given the well-established principles of complementary nucleotide base-pairing.

Preferred siRNA polynucleotides comprise double-stranded polynucleotides of about 18-30 nucleotide base pairs, preferably about 18, about 19, about 20, about 21, about 22, about 23, about 24, about 25, about 26, or about 27 base pairs, and in other preferred embodiments about 19, about 20, about 21, about 22 or about 23 base pairs, or about 27 base pairs, whereby the use of "about" indicates that in certain embodiments and under certain conditions the processive cleavage steps that may give rise to functional siRNA polynucleotides that are capable of interfering with expression of a selected polypeptide may not be absolutely efficient. Hence, siRNA polynucleotides, may include one or more siRNA polynucleotide molecules that may differ (e.g., by nucleotide insertion or deletion) in length by one, two, three, four or more base pairs as a consequence of the variability in processing, in biosynthesis, or in artificial synthesis of the siRNA. The siRNA polynucleotide of the present invention may also comprise a polynucleotide sequence that exhibits variability by differing (e.g., by nucleotide substitution, including transition or transversion) at one, two, three or four nucleotides from a particular sequence. These differences can occur at any of the nucleotide positions of a particular siRNA polynucleotide sequence, depending on the length of the molecule, whether situated in a sense or in an antisense strand of the double-stranded polynucleotide. The nucleotide difference may be found on one strand of a double-stranded polynucleotide, where the complementary nucleotide with which the substitute nucleotide would typically form hydrogen bond base pairing, may not necessarily be correspondingly substituted. In preferred embodiments, the siRNA polynucleotides are homogeneous with respect to a specific nucleotide sequence.

Based on the present disclosure, it should be appreciated that the siRNAs of the present invention may effect silencing of the target polypeptide expression to different degrees. The siRNAs thus must first be tested for their effectiveness. Selection of siRNAs are made therefrom based on the ability of a given siRNA to interfere with or modulate the expression of the target polypeptide. Accordingly, identification of specific siRNA polynucleotide sequences that are capable of interfering with expression of a desired target polypeptide requires production and testing of each siRNA. The methods for testing each siRNA and selection of suitable siRNAs for use in the present invention are fully set forth herein the Examples. Since not all siRNAs that interfere with protein expression will have a physiologically important effect, the present disclosure also sets forth various physiologically relevant assays for determining whether the levels of interference with target protein expression using the siRNAs of the invention have clinically relevant significance.

It is appreciated by one skilled in the art, that siRNAs are easily designed and manufactured. Further, effects of siRNA are typically transient in nature, which make them optimal for certain therapies where sustained inhibition is undesired. Another form of an interfering RNA, shRNA polynucleotides utilize the endogenous processing machinery of the cell and are often designed for high potency, sustainable effects, and fewer off-target effects (Rao et al., 2009, Adv Drug Deliv Rev, 61: 746-759). As would be understood by those skilled in the art, the present invention encompasses both siRNA and shRNA polynucleotides, which can be designed and delivered to inhibit one or more DGK isoform.

One skilled in the art will readily appreciate that as a result of the degeneracy of the genetic code, many different nucleotide sequences may encode the same polypeptide. That is, an amino acid may be encoded by one of several different codons, and a person skilled in the art can readily determine that while one particular nucleotide sequence may differ from another, the polynucleotides may in fact encode polypeptides with identical amino acid sequences. As such, polynucleotides that vary due to differences in codon usage are specifically contemplated by the present invention.

One skilled in the art will appreciate, based on the disclosure provided herein, that one way to decrease the mRNA and/or protein levels of one or more DGK isoform in a cell is by reducing or inhibiting expression of the nucleic acid encoding the DGK isoform. Thus, the protein level of the DGK isoform in a cell can also be decreased using a molecule or compound that inhibits or reduces gene expression such as, for example, an antisense molecule or a ribozyme.

In a preferred embodiment, the modulating sequence is an antisense nucleic acid sequence which is expressed by a plasmid vector. The antisense expressing vector is used to transfect a mammalian cell or the mammal itself, thereby causing reduced endogenous expression of a desired protein in the cell. However, the invention should not be construed to be limited to inhibiting expression of a protein by transfection of cells with antisense molecules. Rather, the invention encompasses other methods known in the art for inhibiting expression or activity of a protein in the cell including, but not limited to, the use of a ribozyme, the expression of a non-functional protein (i.e. dominant negative mutant) and use of an intracellular antibody.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is the fact that ribozymes are sequence-specific.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

Ribozymes useful for inhibiting the expression of a protein may be designed by incorporating target sequences into the basic ribozyme structure which are complementary to the mRNA sequence of the desired protein of the present invention, including but not limited to one or more DGK isoform, and equivalents thereof. Ribozymes targeting the desired protein may be synthesized using commercially available reagents (Applied Biosystems, Inc., Foster City, Calif.) or they may be genetically expressed from DNA encoding them.

In another aspect of the invention, the protein can be inhibited by way of inactivating and/or sequestering the DGK protein. As such, inhibiting the effects of a protein can be accomplished by using a dominant negative mutant. Alternatively an antibody specific for the desired protein, otherwise known as an antagonist to the protein may be used. In one embodiment, the antagonist is a protein and/or compound having the desirable property of interacting with a binding partner of the protein and thereby competing with the corresponding wild-type protein. In another embodiment, the antagonist is a protein and/or compound having the desirable property of interacting with the protein and thereby sequestering the protein.

In another aspect of the invention, expression of the protein is inhibited by a zinc finger nuclease administered to a cell. In general, a zinc finger nuclease comprises a zinc finger binding domain and a cleavage domain.

Zinc finger binding domains may be engineered to recognize and bind to any nucleic acid sequence of choice, for example a nucleic acid sequence associated with the expression of one or more DGK isforms. See, for example, Beerli et al. (2002) Nat. Biotechnol. 20:135-141; Pabo et al. (2001) Ann. Rev. Biochem. 70:313-340; Isalan et al. (2001) Nat. Biotechnol. 19:656-660; Segal et al. (2001) Curr. Opin. Biotechnol. 12:632-637; Choo et al. (2000) Curr. Opin. Struct. Biol. 10:411-416; Zhang et al. (2000) J. Biol. Chem. 275 (43):33850-33860; Doyon et al. (2008) Nat. Biotechnol. 26:702-708; and Santiago et al. (2008) Proc. Natl. Acad. Sci. USA 105:5809-5814. An engineered zinc finger binding domain may have a novel binding specificity compared to a naturally-occurring zinc finger protein. Engineering methods include, but are not limited to, rational design and various types of selection. Rational design includes, for example, using databases comprising doublet, triplet, and/or quadruplet nucleotide sequences and individual zinc finger amino acid sequences, in which each doublet, triplet or quadruplet nucleotide sequence is associated with one or more amino acid sequences of zinc fingers which bind the particular triplet or quadruplet sequence. See, for example, U.S. Pat. Nos. 6,453,242 and 6,534,261, the disclosures of which are incorporated by reference herein in their entireties. As an example, the algorithm of described in U.S. Pat. No. 6,453,242 may be used to design a zinc finger binding domain to target a preselected sequence.

A zinc finger binding domain may be designed to recognize a DNA sequence ranging from about 3 nucleotides to about 21 nucleotides in length, or from about 8 to about 19 nucleotides in length. In general, the zinc finger binding domains of the zinc finger nucleases disclosed herein comprise at least three zinc finger recognition regions (i.e., zinc fingers). In one embodiment, the zinc finger binding domain may comprise four zinc finger recognition regions. In another embodiment, the zinc finger binding domain may comprise five zinc finger recognition regions. In still another embodiment, the zinc finger binding domain may comprise six zinc finger recognition regions. A zinc finger binding domain may be designed to bind to any suitable target DNA sequence. See for example, U.S. Pat. Nos. 6,607,882; 6,534,261 and 6,453,242, the disclosures of which are incorporated by reference herein in their entireties.

Exemplary methods of selecting a zinc finger recognition region may include phage display and two-hybrid systems, and are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237, each of which is incorporated by reference herein in its entirety. In addition, enhancement of binding specificity for zinc finger binding domains has been described, for example, in WO 02/077227.

In some embodiments, the zinc finger nuclease may further comprise a nuclear localization signal or sequence (NLS). A NLS is an amino acid sequence which facilitates targeting the zinc finger nuclease protein into the nucleus to introduce a double stranded break at the target sequence in the chromosome. Nuclear localization signals are known in the art. See, for example, Makkerh et al. (1996) Current Biology 6:1025-1027.

A zinc finger nuclease also includes a cleavage domain. The cleavage domain portion of the zinc finger nucleases disclosed herein may be obtained from any endonuclease or exonuclease. Non-limiting examples of endonucleases from which a cleavage domain may be derived include, but are not limited to, restriction endonucleases and homing endonucleases. See, for example, 2002-2003 Catalog, New England Biolabs, Beverly, Mass.; and Belfort et al. (1997) Nucleic Acids Res. 25:3379-3388 or www.neb.com. Additional enzymes that cleave DNA are known (e.g., SI Nuclease; mung bean nuclease; pancreatic DNase I; micrococcal nuclease; yeast HO endonuclease). See also Linn et al. (eds.) Nucleases, Cold Spring Harbor Laboratory Press, 1993. One or more of these enzymes (or functional fragments thereof) may be used as a source of cleavage domains.

A cleavage domain also may be derived from an enzyme or portion thereof, as described above, that requires dimerization for cleavage activity. Two zinc finger nucleases may be required for cleavage, as each nuclease comprises a monomer of the active enzyme dimer. Alternatively, a single zinc finger nuclease may comprise both monomers to create an active enzyme dimer. As used herein, an "active enzyme dimer" is an enzyme dimer capable of cleaving a nucleic acid molecule. The two cleavage monomers may be derived from the same endonuclease (or functional fragments thereof), or each monomer may be derived from a different endonuclease (or functional fragments thereof).

When two cleavage monomers are used to form an active enzyme dimer, the recognition sites for the two zinc finger nucleases are preferably disposed such that binding of the two zinc finger nucleases to their respective recognition sites places the cleavage monomers in a spatial orientation to each other that allows the cleavage monomers to form an active enzyme dimer, e.g., by dimerizing. As a result, the near edges of the recognition sites may be separated by about 5 to about 18 nucleotides. For instance, the near edges may be separated by about 5, 6, 7, 8, 9, 10, 11, 12, 13, 14, 15, 16, 17 or 18 nucleotides. It will however be understood that any integral number of nucleotides or nucleotide pairs may intervene between two recognition sites (e.g., from about 2 to about 50 nucleotide pairs or more). The near edges of the recognition sites of the zinc finger nucleases, such as for example those described in detail herein, may be separated by 6 nucleotides. In general, the site of cleavage lies between the recognition sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. See, for example, U.S. Pat. Nos. 5,356,802; 5,436,150 and 5,487, 994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31, 978-31, 982. Thus, a zinc finger nuclease may comprise the cleavage domain from at least one Type IIS restriction enzyme and one or more zinc finger binding domains, which may or may not be engineered. Exemplary Type IIS restriction enzymes are described for example in International Publication WO 07/014,275, the disclosure of which is incorporated by reference herein in its entirety. Additional restriction enzymes also contain separable binding and cleavage domains, and these also are contemplated by the present disclosure. See, for example, Roberts et al. (2003) Nucleic Acids Res. 31:418-420.

A zinc finger nuclease may be engineered to introduce a double stranded break at the targeted site of integration. The double stranded break may be at the targeted site of integration, or it may be up to 1, 2, 3, 4, 5, 10, 15, 20, 25, 30, 35, 40, 45, 50, 100, or 1000 nucleotides away from the site of integration. In some embodiments, the double stranded break may be up to 1, 2, 3, 4, 5, 10, 15, or 20 nucleotides away from the site of integration. In other embodiments, the double stranded break may be up to 10, 15, 20, 25, 30, 35, 40, 45, or 50 nucleotides away from the site of integration. In yet other embodiments, the double stranded break may be up to 50, 100, or 1000 nucleotides away from the site of integration.

Modification of Nucleic Acid Molecules

Inhibition of one or more DGK isoform can be accomplished using a nucleic acid molecule. For example, the inhibitor is selected from the group consisting of a small interfering RNA (siRNA), short hairpin RNA (shRNA), a microRNA, an antisense nucleic acid, a ribozyme, a zinc finger nuclease, an expression vector encoding a dominant negative mutant, and the likes.

By way of example, modification of nucleic acid molecules is described in the context of an siRNA molecule. However, the methods of modifying nucleic acid molecules can be applied to other types of nucleic acid based inhibitors of the invention.

Polynucleotides of the siRNA may be prepared using any of a variety of techniques, which are useful for the preparation of specifically desired siRNA polynucleotides. For example, a polynucleotide may be amplified from a cDNA prepared from a suitable cell or tissue type. Such a polynucleotide may be amplified via polymerase chain reaction (PCR). Using this approach, sequence-specific primers are designed based on the sequences provided herein, and may be purchased or synthesized directly. An amplified portion of the primer may be used to isolate a full-length gene, or a desired portion thereof, from a suitable DNA library using well known techniques. A library (cDNA or genomic) is screened using one or more polynucleotide probes or primers suitable for amplification. Preferably, the library is size-selected to include larger polynucleotide sequences. Random primed libraries may also be preferred in order to identify 5' and other upstream regions of the genes. Genomic libraries are preferred for obtaining introns and extending 5' sequences. The siRNA polynucleotide contemplated by the present invention may also be selected from a library of siRNA polynucleotide sequences.

For hybridization techniques, a partial polynucleotide sequence may be labeled (e.g., by nick-translation or end-labeling with $^{32}P$) using well known techniques. A bacterial or bacteriophage library may then be screened by hybridization to filters containing denatured bacterial colonies (or lawns containing phage plaques) with the labeled probe (see, e.g., Sambrook et al., Molecular Cloning: A Laboratory Manual, Cold Spring Harbor Laboratories, Cold Spring Harbor, N.Y., 2001). Hybridizing colonies or plaques are selected and expanded, and the DNA is isolated for further analysis.

Alternatively, numerous amplification techniques are known in the art for obtaining a full-length coding sequence from a partial cDNA sequence. Within such techniques, amplification is generally performed via PCR. One such technique is known as "rapid amplification of cDNA ends" or RACE (see, e.g., Sambrook et al., Molecular Cloning: A Laboratory Manual, Cold Spring Harbor Laboratories, Cold Spring Harbor, N.Y., 2001).

A number of specific siRNA polynucleotide sequences useful for interfering with target polypeptide expression are presented in the Examples, the Drawings, and in the Sequence Listing included herein. siRNA polynucleotides may generally be prepared by any method known in the art, including, for example, solid phase chemical synthesis. Modifications in a polynucleotide sequence may also be introduced using standard mutagenesis techniques, such as oligonucleotide-directed site-specific mutagenesis. Further, siRNAs may be chemically modified or conjugated with other molecules to improve their stability and/or delivery properties. Included as one aspect of the invention are siRNAs as described herein, wherein one or more ribose sugars has been removed therefrom.

Alternatively, siRNA polynucleotide molecules may be generated by in vitro or in vivo transcription of suitable DNA sequences (e.g., polynucleotide sequences encoding a target polypeptide, or a desired portion thereof), provided that the DNA is incorporated into a vector with a suitable RNA polymerase promoter (such as for example, T7, U6, H1, or SP6 although other promoters may be equally useful). In addition, an siRNA polynucleotide may be administered to a mammal, as may be a DNA sequence (e.g., a recombinant nucleic acid construct as provided herein) that supports transcription (and optionally appropriate processing steps) such that a desired siRNA is generated in vivo.

In one embodiment, an siRNA polynucleotide, wherein the siRNA polynucleotide is capable of interfering with expression of a target polypeptide can be used to generate a silenced cell. Any siRNA polynucleotide that, when contacted with a biological source for a period of time, results in a significant decrease in the expression of the target polypeptide is included in the invention. Preferably the decrease is greater than about 10%, more preferably greater than about 20%, more preferably greater than about 30%, more preferably greater than about 40%, about 50%, about 60%, about 70%, about 75%, about 80%, about 85%, about 90%, about 95% or about 98% relative to the expression level of the target polypeptide detected in the absence of the siRNA. Preferably, the presence of the siRNA polynucleotide in a cell does not result in or cause any undesired toxic effects, for example, apoptosis or death of a cell in which apoptosis is not a desired effect of RNA interference.

In another embodiment, the siRNA polynucleotide that, when contacted with a biological source for a period of time, results in a significant decrease in the expression of the target polypeptide. Preferably the decrease is about 10%-20%, more preferably about 20%-30%, more preferably about 30%-40%, more preferably about 40%-50%, more preferably about 50%-60%, more preferably about 60%-70%, more preferably about 70%-80%, more preferably about 80%-90%, more preferably about 90%-95%, more preferably about 95%-98% relative to the expression level of the target polypeptide detected in the absence of the siRNA. Preferably, the presence of the siRNA polynucleotide in a cell does not result in or cause any undesired toxic effects.

In yet another embodiment, the siRNA polynucleotide that, when contacted with a biological source for a period of time, results in a significant decrease in the expression of the target polypeptide. Preferably the decrease is about 10% or more, more preferably about 20% or more, more preferably about 30% or more, more preferably about 40% or more, more preferably about 50% or more, more preferably about 60% or more, more preferably about 70% or more, more preferably about 80% or more, more preferably about 90% or more, more preferably about 95% or more, more preferably about 98% or more relative to the expression level of the target polypeptide detected in the absence of the siRNA. Preferably, the presence of the siRNA polynucleotide in a cell does not result in or cause any undesired toxic effects.

Any polynucleotide of the invention may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl-methyl-, thio- and other modified forms of adenine, cytidine, guanine, thymine, and uridine.

Antibodies

The concept of "Intracellular Immunization" or "Intracellular Inhibition" has in the last decade emerged as an important strategy to counteract functionalities of pathogenic bacteria, viruses and parasites. Intracellular Immunization utilizes molecular modulators such as anti-sense RNA, ribozymes, dominant negative mutants and intracellular antibodies (intrabodies) for inhibiting functional gene expression within the cell. Previous studies have shown the efficacy of intrabodies (e.g., sFvs and Fabs) targeting expression in different compartments of the cell, including the nucleus, ER, cytoplasm, golgi, plasma membrane, mitochondria, where they act to counteract antigens or molecules in a specific pathway. (Marasco, W. A., et al, Proc. Natl. Acad. Sci., USA 90:7889-7893 (1993); Chen, S. Y., et al., Human Gene Therapy 5:595-601 (1994); Chen, S. Y., et al., Proc Natl Acad Sci, USA 91:5932-5936 (1994); Mhashilkar, A. M., et al., Embo J 14:1542-1551 (1995); Marasco, W. A., et al. Gene Therapy 4:11-15 (1997); Richardson, J. H., et al., Proc Natl Acad Sci, USA 92:3137-3141 (1995); Duan, L., et al., Human Gene Therapy 5:1315-1324 (1994)). The antibodies can be localized to specific cellular compartments, e.g., the ER, nucleus, inner surface of the plasma membrane, the cytoplasm and the mitochondria. (See e.g., Marasco et al, 1993; Mhashilkar et al., 1995; Biocca et al., 1995).

As will be understood by one skilled in the art, any antibody that can recognize and bind to an antigen of interest is useful in the present invention. Preferably, the antibody is an intracellularly expressed antibody, or otherwise referred to as an intrabody. That is, the antibody can inhibit one or more DGK isoforms to provide a beneficial effect, in addition to other effects, by enhancing cytolytic activity of a T cell.

Accordingly, the invention provides a single domain intrabody that binds to an intracellular (cytosolic) protein or intracellular domain of a protein (e.g., one or more DGK isoforms). The intrabody is used to, e.g., specifically inhibit an enzymatic activity of the intracellular protein or domain. Intracellular proteins and domains that can be targets for the intrabody include kinases, a proteases, nucleases, telomerases, transferases, reductases, hydrolyases, and isomerases. In an embodiment of the invention, the intrabody is specific for one or more DGK isoforms.

The intrabody comprises whole antibodies, heavy chains, Fab' fragments, single-chain antibodies and diabodies. In one preferred method of the present invention, the intrabody comprises a single-chain antibody (sFv). The antibodies for use in the present invention can be obtained by methods known in the art against the antigen of interest. For example, single chain antibodies are prepared according to the teaching of PCT/US93/06735, filed on Jan. 17, 1992 and U.S. patent application Ser. No. 08/350,215, filed on Dec. 6, 1994, incorporated herein by reference.

According to the invention, an intrabody is created that specifically inhibits an intracellular protein or protein activity. The intrabody can be selected to bind to an intracellular protein of any organism. Notably, because of the degree of evolutionary conservation of enzymes, protein-protein interactions, and signal transduction pathways, even though the intrabody will preferably be specific for an enzyme in a cell, it can also be expected that the intrabody will inhibit a homologous enzyme in a related species.

Domain intrabodies specific for any particular enzyme or catalytic region thereof can be readily identified by screening a single domain antibody library. Antibody engineering has enabled the production of single domain antibody libraries, and such libraries have been constructed from a number of variable domain scaffolds, including human $V_H$ or $Y_L$ (Jespers, L. et al., 2004, J. Mol. Biol. 337:893-903), camelid $V_H$ (Tanha, J. et al., 2001, J. Biol. Chem. 276:24774-80), and shark V-NAR (Nuttall, S. D., et al., 2004, Proteins 55:187-97). Libraries from other species exist as well. However, to avoid adverse immune responses when domain intrabodies are administered to a subject, it is generally preferable that source of domain intrabody correspond to the subject to which the intrabody will be administered.

In an embodiment of the invention, domain intrabodies are obtained by selecting a single variable domain from a variable region of an antibody having two variable domains (i.e., a heterodimer of a heavy chain variable domain and a light chain variable domain). Methods for obtaining heavy chain-light chain heterodimers include, for example, the immunological method described by Kohler and Milstein, Nature 256:495-497 (1975) and Campbell, Monoclonal Antibody Technology, The Production and Characterization of Rodent and Human Hybridomas, Burdon et al., Eds., Laboratory Techniques in Biochemistry and Molecular Biology, Volume 13, Elsevier Science Publishers, Amsterdam (1985); as well as by the recombinant. DNA methods such as described by Huse et al, Science 246, 1275-81. (1989). The antibodies can also be obtained from phage display or yeast surface display libraries bearing combinations of $V_H$ and $V_L$ domains in the form of scFv or Fab. The $V_H$ and $V_L$ domains can be encoded by nucleotides that are synthetic, partially synthetic, or naturally derived. Single variable domain antibodies can also be found in Fab and scFv phage display libraries (Cai, X. et al., 1996, Proc. Natl. Acad. Sci. USA. 93:6280-5). In certain embodiments, phage display libraries bearing human antibody fragments are preferred. Other sources of human antibodies are transgenic mice engineered to express human immunoglobulin genes.

The invention also includes functional equivalents of the antibodies described herein. Functional equivalents have binding characteristics comparable to those of the antibodies, and include, for example, hybridized and single chain antibodies, as well as fragments thereof. Methods of producing such functional equivalents are disclosed in PCT Application WO 93/21319 and PCT Application WO 89/09622.

Functional equivalents include polypeptides with amino acid sequences substantially the same as the amino acid sequence of the variable or hypervariable regions of the antibodies. "Substantially the same" amino acid sequence is defined herein as a sequence with at least 70%, preferably at least about 80%, more preferably at least about 90%, even more preferably at least about 95%, and most preferably at least 99% homology to another amino acid sequence (or any integer in between 70 and 99), as determined by the FASTA search method in accordance with Pearson and Lipman, 1988 Proc. Nat'l. Acad. Sci. USA 85: 2444-2448. Chimeric or other hybrid antibodies have constant regions derived substantially or exclusively from human antibody constant regions and variable regions derived substantially or exclusively from the sequence of the variable region of a monoclonal antibody from each stable hybridoma.

Genetic Modification

The invention includes an isolated nucleic acid operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In one embodiment, the expression of natural or synthetic nucleic acids encoding the inhibitor is typically achieved by operably linking a nucleic acid to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The desired nucleic can be cloned into a number of types of vectors. However, the present invention should not be construed to be limited to any particular vector. Instead, the present invention should be construed to encompass a wide plethora of vectors which are readily available and/or well-known in the art. For example, a desired polynucleotide of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For expression of the desired polynucleotide, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. Nos. 4,683,202, 5,928, 906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2001). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, the HER-2 promoter and the PSA associated promoter sequences.

In order to assess the expression of the inhibitor, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479:79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast or insect cell by any method in the art. For example, the expression vector can be transferred into a host cell by physical, chemical or biological means. It is readily understood that the introduction of the expression vector comprising the polynucleotide of the invention yields a silenced cell with respect to a protein.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In one embodiment, the inhibitor of the invention encompasses in vitro transcribed RNA. In one embodiment, an in vitro transcribed RNA can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA.

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

Genes that can be used as sources of DNA for PCR include genes that encode polypeptides that provide a therapeutic or prophylactic effect to an organism or that can be used to diagnose a disease or disorder in an organism. Preferred genes are genes which are useful for a short term treatment, or where there are safety concerns regarding dosage or the expressed gene. For example, for treatment of cancer, autoimmune disorders, parasitic, viral, bacterial, fungal or other infections, the transgene(s) to be expressed may encode a polypeptide that functions as a ligand or receptor for cells of the immune system, or can function to stimulate or inhibit the immune system of an organism. In some embodiments, t is not desirable to have prolonged ongoing stimulation of the immune system, nor necessary to produce changes which last after successful treatment, since this may then elicit a new problem. For treatment of an autoimmune disorder, it may be desirable to inhibit or suppress the immune system during a flare-up, but not long term, which could result in the patient becoming overly sensitive to an infection.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as OOT tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001);

Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Modified Cell

In one embodiment, the instant invention provides a cell-based system for expressing an inhibitor that is capable of inhibiting one or more DGK isoform. The invention includes a cell that has been modified to possess heightened cytolytic activity as compared to an otherwise identical cell. The modified cell is suitable for administration to a mammalian recipient alone or in combination with other therapies.

In one embodiment, the instant invention provides a cell for use in adoptive T cell transfer, wherein the T cell is modified to express an inhibitor that is capable of inhibiting one or more DGK isoform. In one embodiment, the invention provides a T cell modified to express a CAR and an inhibitor capable for inhibiting one or more DGK isoform.

In general, a CAR and CAR modified T cells are described in PCT/US2011/064191, which is incorporated herein by reference. In one embodiment, a CAR comprises an extracellular domain and an intracellular domain. The extracellular domain comprises a target-specific binding element otherwise referred to as an antigen binding moiety. The intracellular domain or otherwise the cytoplasmic domain comprises, a costimulatory signaling region and a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

As would be understood by those skilled in the art, CAR modified T cells can be generated by any method known in the art. For example, the CAR modified T cells can be generated by introducing an expression vector encoding the CAR to a T cell, as described elsewhere herein. In one embodiment, the DGK inhibited cells of the invention are generated by a method comprising administering an expression vector which encodes a CAR and further encodes the inhibitor of the invention, to a T cell. In another embodiment, the method comprises administering an expression vector encoding a CAR and an expression vector encoding the inhibitor, to the T cell.

In another embodiment, the CAR modified T cells can be generated by administering in vitro transcribed RNA encoding a CAR, as described elsewhere herein. In one embodiment, the DGK inhibited cells of the invention are generated by a method comprising transfecting an RNA which encodes a CAR and further encodes the inhibitor of the invention, to a T cell. In another embodiment, the method comprises transfecting an RNA encoding a CAR and an RNA encoding the inhibitor, to the T cell.

In another embodiment, the DGK inhibited cells of the invention are generated by a method comprising transfecting an expression vector encoding a CAR and an RNA encoding the inhibitor, to a T cell. In yet another embodiment, the DGK inhibited cells of the invention are generated by a method comprising transfecting an RNA encoding a CAR and an expression vector encoding the inhibitor, to a T cell.

In some embodiments, the nucleic acids of the invention are delivered into cells using a retroviral or lentiviral vector. Retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In other embodiments, the nucleic acids of the invention are delivered into cells using in vitro transcribed mRNA. In vitro transcribed mRNA can be delivered into different types of eukaryotic cells as well as into tissues and whole organisms using transfected cells as carriers or cell-free local or systemic delivery of encapsulated, bound or naked mRNA. The method used can be for any purpose where transient expression is required or sufficient.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

Sources of T Cells

Prior to expansion and genetic modification of the T cells of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of $CD8^+$ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11 b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

Whether prior to or after genetic modification of the T cells to express a desirable protein (e.g., a CAR), the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besangon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, 104 to 109 T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-7, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

Therapeutic Application

The present invention includes an inhibitor of any one or more DGK isoform in a cell. The invention also includes a cell having heighted cytolytic activity wherein one or more DGK isoform in the cell has been inhibited.

In one embodiment, the DGK inhibitor of the invention can be administered to a subject in need thereof. When the DGK inhibitor of the invention is prepared for administration, it is preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the DGK inhibitors of the invention can be prepared by procedures known in the art using well known and readily available ingredients. The DGK inhibitor of the invention can also be formulated as solutions appropriate for parenteral administration, for instance by intramuscular, subcutaneous or intravenous routes.

In one embodiment, the present invention includes a type of cellular therapy where T cells are genetically modified to express a DGK inhibitor and the modified T cell is infused to a recipient in need thereof. In one embodiment, the modified T cell is modified to express a desired protein (e.g., a CAR). The infused cell is able to kill tumor cells in the recipient.

The present invention includes a method of enhancing the immune response during adoptive T cell transfer comprising the steps of contacting one or more T cells with an inhibitor of one or more DGK isoform. The modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding the inhibitor to the cells, and/or iii) cryopreservation of the cells.

Ex vivo procedures are well known in the art. Briefly, cells are isolated from a mammal (preferably a human) and modified to enhance its cytolytic activity according to the methods of the invention. For example, the cell is modified to have any one or more DGK isoform inhibited. The heighted immunogenic cell can be administered to a mammalian recipient to provide a therapeutic benefit. The mammalian recipient may be a human and the cell so modified can be autologous with respect to the recipient. Alternatively, the cells can be allogeneic, syngeneic or xenogeneic with respect to the recipient.

In addition to using a cell-based therapy in terms of ex vivo modification of T cells, the present invention also provides compositions and methods for in vivo therapies to elicit an immune response directed against an antigen in a patient.

In one embodiment, the mammal has a type of cancer which expresses a tumor-specific antigen. In accordance with the present invention, a composition can be made which recognizes a specific tumor-specific antigen. In such cases, the inhibitor of one or more DGK isoform is administered to a T cell that is directed to a given tumor-specific antigen, resulting in an improved therapeutic outcome for the patient, evidenced by, e.g., a slowing or diminution of the growth of cancer cells or a solid tumor which expresses the tumor-specific antigen, or a reduction in the total number of cancer cells or total tumor burden.

In another embodiment, the compounds of the present invention may be used in combination with existing therapeutic agents used to treat cancer. In some instances, the compounds of the invention may be used in combination these therapeutic agents to enhance the antitumor effect of the therapeutic agent.

In order to evaluate potential therapeutic efficacy of the compounds of the invention in combination with the antitumor therapeutics described elsewhere herein, these combinations may be tested for antitumor activity according to methods known in the art.

In one aspect, the present invention contemplates that the inhibitors of the invention may be used in combination with a therapeutic agent such as an anti-tumor agent including but not limited to a chemotherapeutic agent, an anti-cell proliferation agent or any combination thereof.

The invention should not be limited to any particular chemotherapeutic agent. Rather, any chemotherapeutic agent can be linked to the antibodies of the invention. For example, any conventional chemotherapeutic agents of the following non-limiting exemplary classes are included in the invention: alkylating agents; nitrosoureas; antimetabolites; antitumor antibiotics; plant alkyloids; taxanes; hormonal agents; and miscellaneous agents.

Alkylating agents are so named because of their ability to add alkyl groups to many electronegative groups under conditions present in cells, thereby interfering with DNA replication to prevent cancer cells from reproducing. Most alkylating agents are cell cycle non-specific. In specific aspects, they stop tumor growth by cross-linking guanine bases in DNA double-helix strands. Non-limiting examples include busulfan, carboplatin, chlorambucil, cisplatin, cyclophosphamide, dacarbazine, ifosfamide, mechlorethamine hydrochloride, melphalan, procarbazine, thiotepa, and uracil mustard.

Anti-metabolites prevent incorporation of bases into DNA during the synthesis (S) phase of the cell cycle, prohibiting normal development and division. Non-limiting examples of antimetabolites include drugs such as 5-fluorouracil, 6-mercaptopurine, capecitabine, cytosine arabinoside, floxuridine, fludarabine, gemcitabine, methotrexate, and thioguanine.

There are a variety of antitumor antibiotics that generally prevent cell division by interfering with enzymes needed for cell division or by altering the membranes that surround cells. Included in this class are the anthracyclines, such as doxorubicin, which act to prevent cell division by disrupting the structure of the DNA and terminate its function. These agents are cell cycle non-specific. Non-limiting examples of antitumor antibiotics include dactinomycin, daunorubicin, doxorubicin, idarubicin, mitomycin-C, and mitoxantrone.

Plant alkaloids inhibit or stop mitosis or inhibit enzymes that prevent cells from making proteins needed for cell growth. Frequently used plant alkaloids include vinblastine, vincristine, vindesine, and vinorelbine. However, the invention should not be construed as being limited solely to these plant alkaloids.

The taxanes affect cell structures called microtubules that are important in cellular functions. In normal cell growth, microtubules are formed when a cell starts dividing, but once the cell stops dividing, the microtubules are disassembled or destroyed. Taxanes prohibit the microtubules from breaking down such that the cancer cells become so clogged with microtubules that they cannot grow and divide. Non-limiting exemplary taxanes include paclitaxel and docetaxel.

Hormonal agents and hormone-like drugs are utilized for certain types of cancer, including, for example, leukemia, lymphoma, and multiple myeloma. They are often employed with other types of chemotherapy drugs to enhance their effectiveness. Sex hormones are used to alter the action or production of female or male hormones and are used to slow the growth of breast, prostate, and endometrial cancers. Inhibiting the production (aromatase inhibitors) or action (tamoxifen) of these hormones can often be used as an adjunct to therapy. Some other tumors are also hormone dependent. Tamoxifen is a non-limiting example of a hormonal agent that interferes with the activity of estrogen, which promotes the growth of breast cancer cells.

Miscellaneous agents include chemotherapeutics such as bleomycin, hydroxyurea, L-asparaginase, and procarbazine that are also useful in the invention.

An anti-cell proliferation agent can further be defined as an apoptosis-inducing agent or a cytotoxic agent. The apoptosis-inducing agent may be a granzyme, a Bcl-2 family member, cytochrome C, a caspase, or a combination thereof. Exemplary granzymes include granzyme A, granzyme B, granzyme C, granzyme D, granzyme E, granzyme F, granzyme G, granzyme H, granzyme I, granzyme J, granzyme K, granzyme L, granzyme M, granzyme N, or a combination thereof. In other specific aspects, the Bcl-2 family member is, for example, Bax, Bak, Bcl-Xs, Bad, Bid, Bik, Hrk, Bok, or a combination thereof.

In additional aspects, the caspase is caspase-1, caspase-2, caspase-3, caspase-4, caspase-5, caspase-6, caspase-7, caspase-8, caspase-9, caspase-10, caspase-11, caspase-12, caspase-13, caspase-14, or a combination thereof. In specific aspects, the cytotoxic agent is TNF-α, gelonin, Prodigiosin, a ribosome-inhibiting protein (RIP), *Pseudomonas exotoxin*, *Clostridium difficile* Toxin B, *Helicobacter pylori* VacA, *Yersinia enterocolitica* YopT, Violacein, diethylenetriaminepentaacetic acid, irofulven, Diptheria Toxin, mitogillin, ricin, botulinum toxin, cholera toxin, saporin 6, or a combination thereof.

In some embodiments, an effective amount of a compound of the invention and a therapeutic agent is a synergistic amount. As used herein, a "synergistic combination" or a "synergistic amount" of a compound of the invention and a therapeutic agent is a combination or amount that is more effective in the therapeutic or prophylactic treatment of a disease than the incremental improvement in treatment outcome that could be predicted or expected from a merely additive combination of (i) the therapeutic or prophylactic benefit of the compound of the invention when administered at that same dosage as a monotherapy and (ii) the therapeutic or prophylactic benefit of the therapeutic agent when administered at the same dosage as a monotherapy.

Screening Agents

The samples used in the detection methods of the present invention include, but are not limited to, cells or tissues, protein, membrane, or nucleic acid extracts of the cells or tissues, and biological fluids such as blood, serum, and plasma. The sample used in the methods of the invention will vary based on the assay format, nature of the detection method, and the tissues, cells or extracts which are used as the sample. Methods for preparing protein extracts, membrane extracts or nucleic acid extracts of cells are well known in the art and can be readily be adapted in order to obtain a sample which is compatible with the method utilized (see, for example, Ausubel et al., Current Protocols in Molecular Biology, Wiley Press, Boston, Mass. (1993)).

Candidate compounds are screened for the ability to inhibit any one or more DGK isoform. The determination of the inhibitory function of the candidate agent to any one or more DGK isoform may be done in a number of ways. In any event, the candidate agent should increase the cytolytic activity of the cell compare to a cell not contacted with the agent.

The method of identifying an agent capable of inhibiting any one or more DGK isoform includes the initial step of contacting a cell with the agent and determining the activity or level of any one or more DGK isoform. A decrease in the activity or level of any one or more DGK isoform indicates that the agent is an inhibitor. Preferably, the agent is also capable of enhancing the cytolytic activity of a cell.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Augmenting Efficacy of Chimeric Antigen Receptor T Cells

The loss of anti-tumor efficacy of CD8 T cells within murine tumors has been recognized for many years. However, virtually nothing is known about the effects of the tumor microenvironment on genetically altered CAR-T cells. Described herein is the identification of a new target within T cells, the molecule Diacylgylceral Kinase (DGK), which appears to limit T cell killing and cytokine release. By genetically inhibiting this pathway in CAR T cells, their anti-tumor efficacy is able to be increased. The results presented herein demonstrate that inhibition of DGK can augment adoptive T cell transfer.

Activation of T cells through the T-cell antigen receptor (TCR) or through CAR, results in a series of molecular events that culminate in T cell activation. Perhaps the most crucial event downstream of these receptors is in the cleavage of the phospholipid PIP2 (phosphotidyl-4,5-inositol) by phospholipase C g1 (PLCg1) into the second messengers diacylglycerol (DAG) and inositol-1,4,5-phosphate (IP3). Whereas IP3 serves to activate calcium signaling in T cells, DAG binds and activates proteins important in T cell activation, such as the Ras activating protein RasGRP1. At the same time that T cells produce DAG, DGK's are recruited to sites of T cell signaling to phosphorylate DAG to form phosphatidic acid, terminating DAG-mediated signaling (Zheng et al., 2008, EMBO Rep. 9:50-55; Zhong et al., 2008, Immunol. Rev. 224:249-264). There are a number of DGK isoforms, but DGKα and DGK appear to be the most important (Zhong et al., 2008, Immunol. Rev. 224:249-264). Deletion of DGK thus results in T cells that are less capable of "turning-off" DAG-mediated signaling within T cells. It has been previously shown that deletion of either isoform of DGK, DGKα or DGKζ, results in T cells that demonstrate enhanced signal transduction and appear more resistant to anergy-inducing stimuli, but that do not appear to induce spontaneous auto-immunity. Recent work by Prinz et al. (Prinz et al., 2012, J. Immunol. 188:5990-6000) in freshly isolated human tumor infiltrating lymphocytes (TIL) from renal cell cancers revealed elevated levels of DGKα in their hypofunctional TIL. They found that pharmacologic inhibition of DGK with DGK Type 1 inhibitor could improve TIL function. Thus, it was examined whether deletion of either or both isoforms of DGK could result in more potent responses downstream of CAR signal transduction (Zhong et al., 2003, Nat. Immunol.:882-890; Olenchock et al., 2006, Nat. Immunol. 7:1174-1181; Zha et al., 2006, Nat. Immunol. 7:1166-1173).

The results presented herein also show that intravenous injection of the DGK KO mesoCAR T cells augments efficacy. This was important as this would be the preferred route of administration in human patients.

The materials and methods employed in these experiments are now described.

Chimeric Antigen Receptor (CAR)

A CAR (FIG. 1) is generally comprised of three main components: 1) the external single chain fragment variable region (scFv) derived from the linked $V_H$ and $V_L$ domains of the antigen binding region of a monoclonal antibody (mAb), 2) a flexible hinge sequence, such as from a CD8α or immunoglobulin sequence, 3), and one or more intracellular signaling domains, which may include cytoplasmic domains from CD3-ε, CD3-γ, or CD3-ζ from the TCR construct or high-affinity receptor FcεRI. T cells expressing the "first generation" CARs, which signaled solely via a lone CD3-ζ domain, were found to be rapidly lost, so that peripheral T cell persistence was very short in a number of early clinical trials (Jensen et al., 2010, Biol. Blood Marrow Transplant 16:1245-1256; Till et al., 2008, Blood 112:2261-2271; Pule et al., 2008, Nat. Med. 14:1264-1270; Park et al., 2007, Mol. Ther. 15:825-833). However, the CAR design has evolved to contain up to 3 internal signal domains (e.g. chimeric CD28, CD134, CD137 (41BB), Lck, ICOS, and DAP10 that enhance T cell activation and survival upon antigen binding (Zhao et al., 2009, J. Immunol. 183:5563-5574; Kowolik et al., 2006, Cancer Res. 66:10995-11004; Wang et al., 2007, Hum. Gene Ther. 18:712-725; Yvon et al., 2009, Clin. Cancer Res. 15:5852-5860; Milone et al., 2009, Mol. Ther. 17:1453-1464). The "right" combination of internal signaling domains needs to induce CAR-dependent killing, but avoid supraphysiologic T cell activation which may lead to T-cell death or systemic toxic effects (Morgan et al., 2010, Mol. Ther. 18:843-851). The main advantages of CAR technology include: i) harnessing the high affinity/specificity antigen binding of the scFv, ii) freedom from MHC restriction, and iii) the relative ease with which patient-derived blood lymphocytes can be expanded and transduced with the desired CAR (June, 2007, J. Clin. Invest. 117:1466-1476; Jena et al., 2010, Blood 116:1035-1044; Peinert et al., 2009, Immunotherapy 1:905-912; Eshhar, 2010, Curr. Opin. Mol. Ther. 12:55-63). Despite extensive research about signaling through the native T cell receptor (TCR), there has been relatively little research done on CAR signaling, especially in human CAR T cells. Although the "basics" seem to be similar between TCR and CAR signaling, there are likely some differences, since unlike signaling through a standard TCR, CAR signaling will not involve the CD8 molecule, nor the majority of the CD3 complex.

Mouse Models

Figure 2:
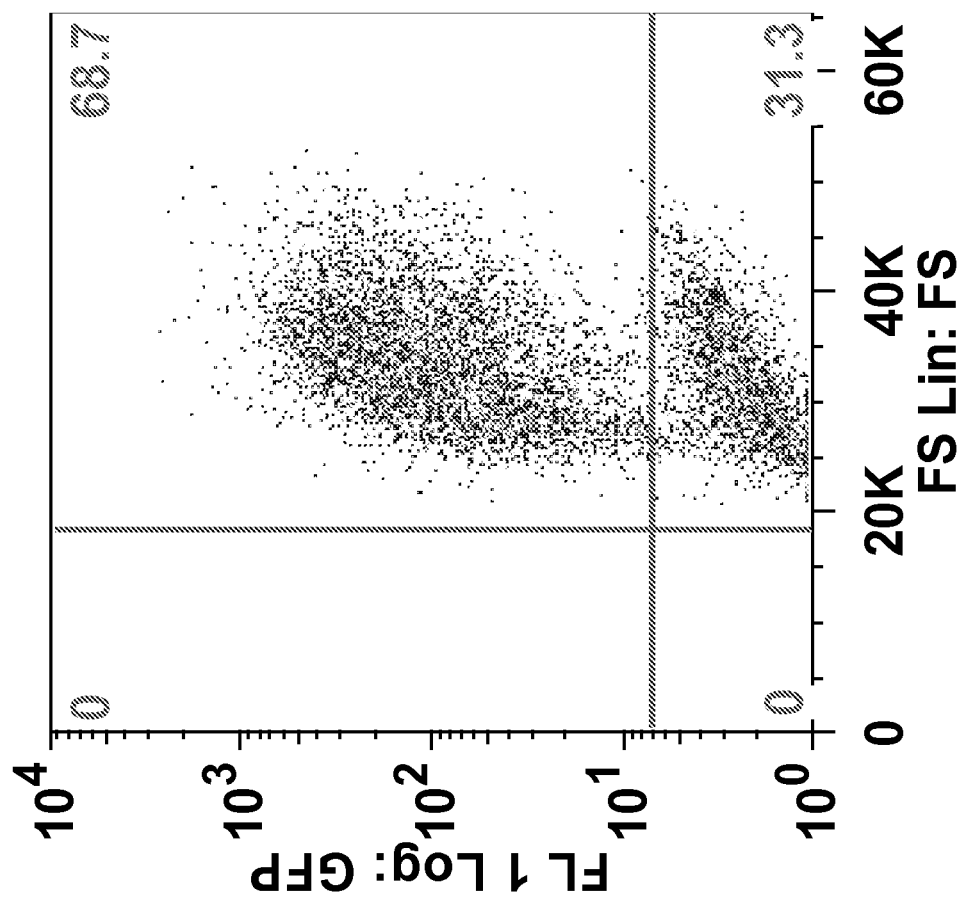
FIG. 2 is a graph depicting the results from the transduction of mouse T cells with retrovirus encoding a CAR. As depicted, transduction leads to surface expression of the CAR on nearly 70% of T cells.
Figure 3:
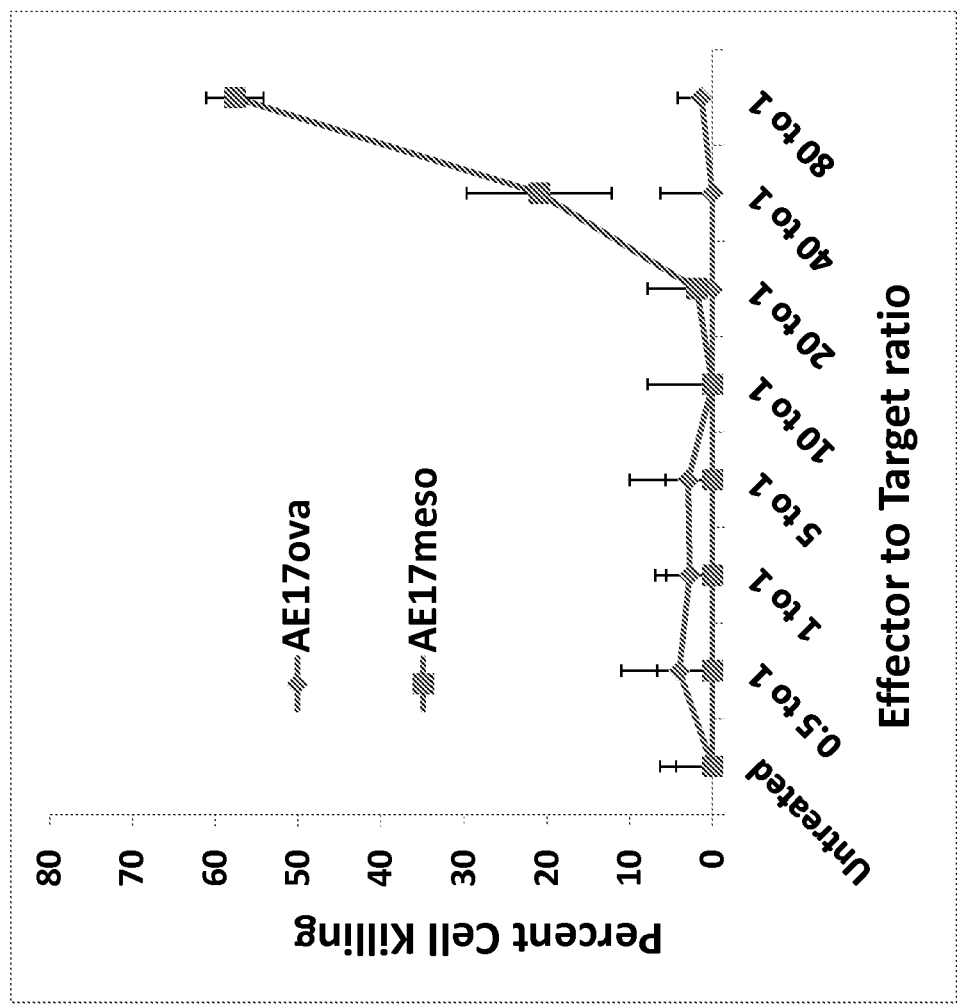
FIG. 3 is a graph depicting the results of an assay examining the percent cell killing of AE17 tumor cells using mouse T cell CARs at a variety of ratios of T cell CARs per tumor cell.

The techniques necessary to transduce activated mouse T cells with CARs using modified retroviruses were developed. After genetic engineering, between 40-70% of the T cells expressed a CAR targeting the human protein mesothelin on the surface of mouse or human tumor cells (FIG. 2). When added to mesothelin-expressing tumor cells, the mouse T cell CARs can kill about 20% of tumor cells over 24 hours at a ratio of 40 T cells per one tumor cell (FIG. 3).

It was examined whether mouse T cells lacking DGKζ, DGKα or both, might persist longer in mice and retain greater activation. Accordingly, Mouse T cells from wild type mice (WT), DGKα KO mice, and DGKζ KO mice were transduced with the mesothelin CAR transcript and were observed to achieved the same levels of expression (~60%). As a prelude to studying their effect after IV injection into tumor-bearing mice, their in vitro ability to kill tumor cells and secrete the inhibitory cytokine interferon-γ was examined. Transduced T cells were mixed at varying ratios with tumor cells expressing mesothelin (AE17meso) or with tumor cells which did not express mesothelin (AE17). The cells were allowed to co-incubate for 18 hours. At that time, the percent killing of tumor cells was determined and supernatants were removed for measurement of INFγ.

The results of the experiments are now described.

Figure 4:
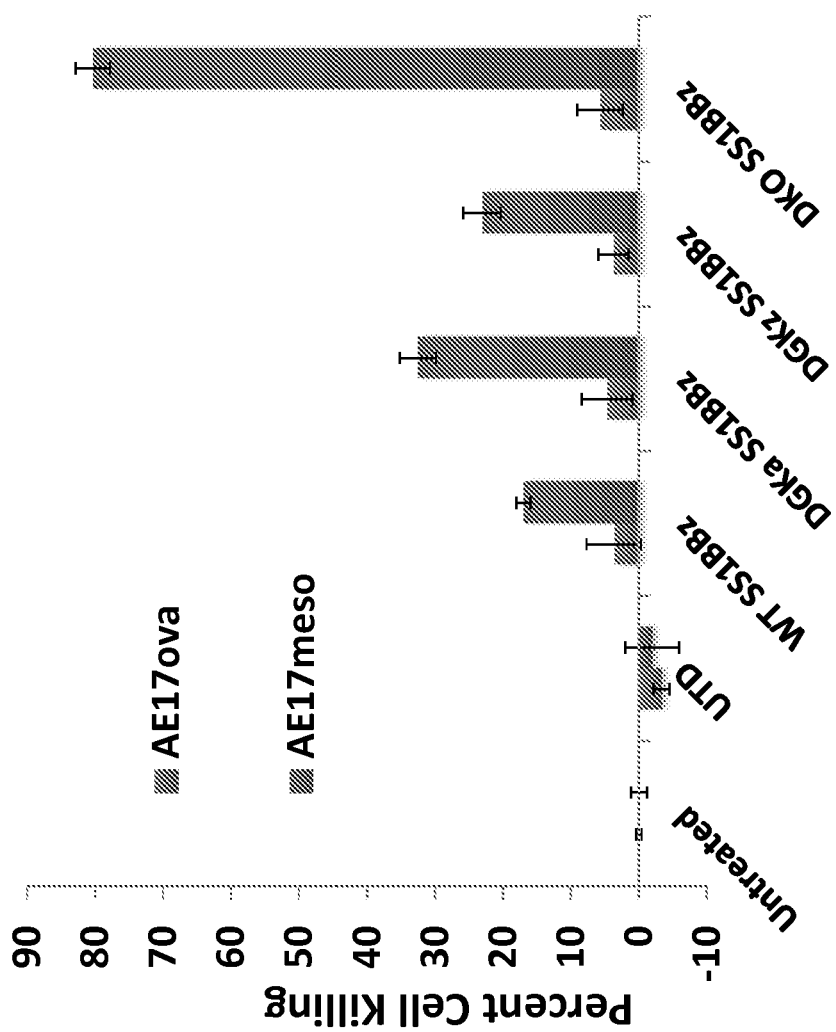
FIG. 4 is a graph depicting the killing of tumor cells when using a 40:1 ratio of T cells per one tumor cell.
Figure 5:
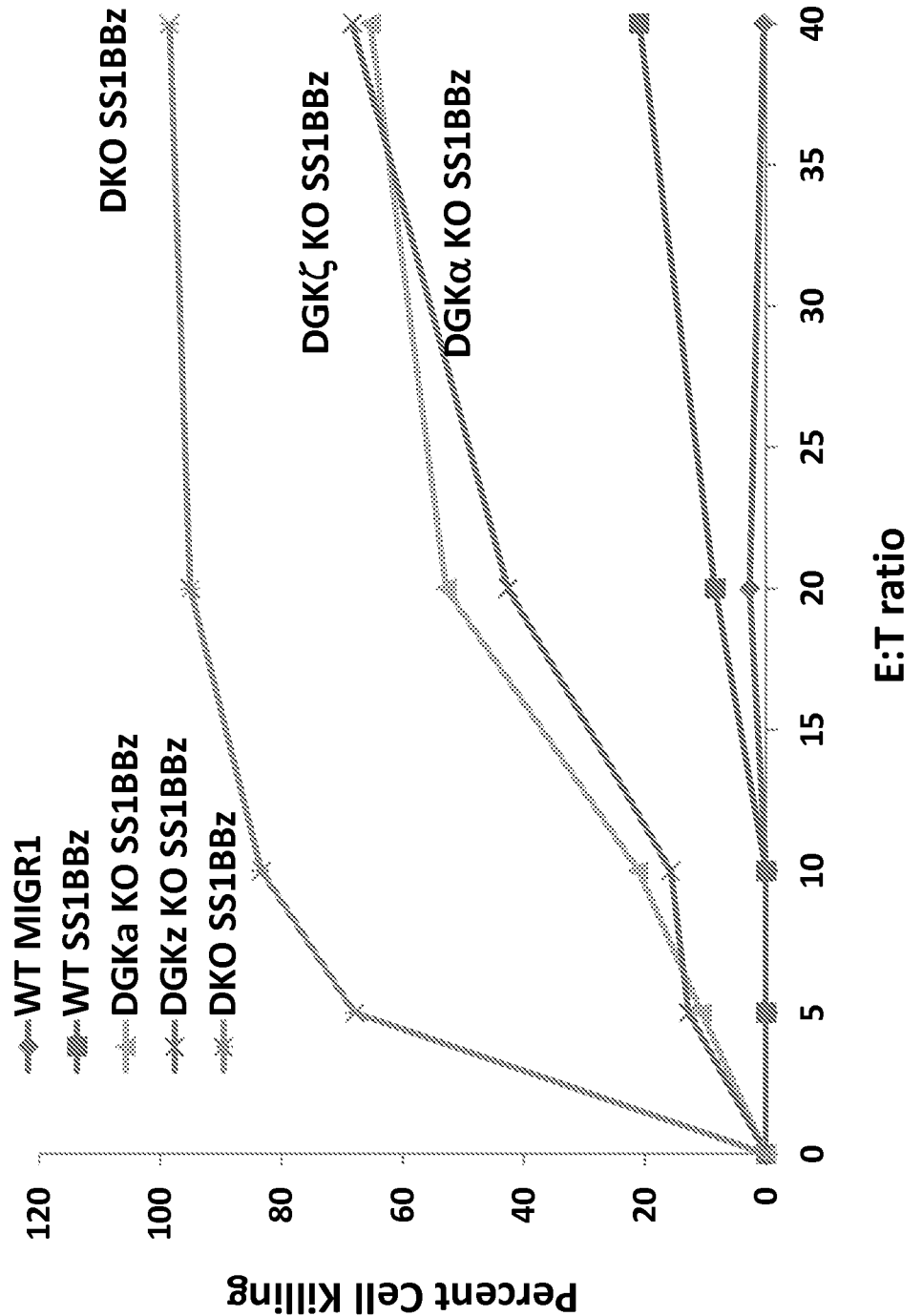
FIG. 5 is a graph depicting the ability of the T cell CARs to kill tumor cells in wild-type, DGKα knockout, DGKζ knockout, or double DGKα/DGKζ knockout T cells.
Figure 6:
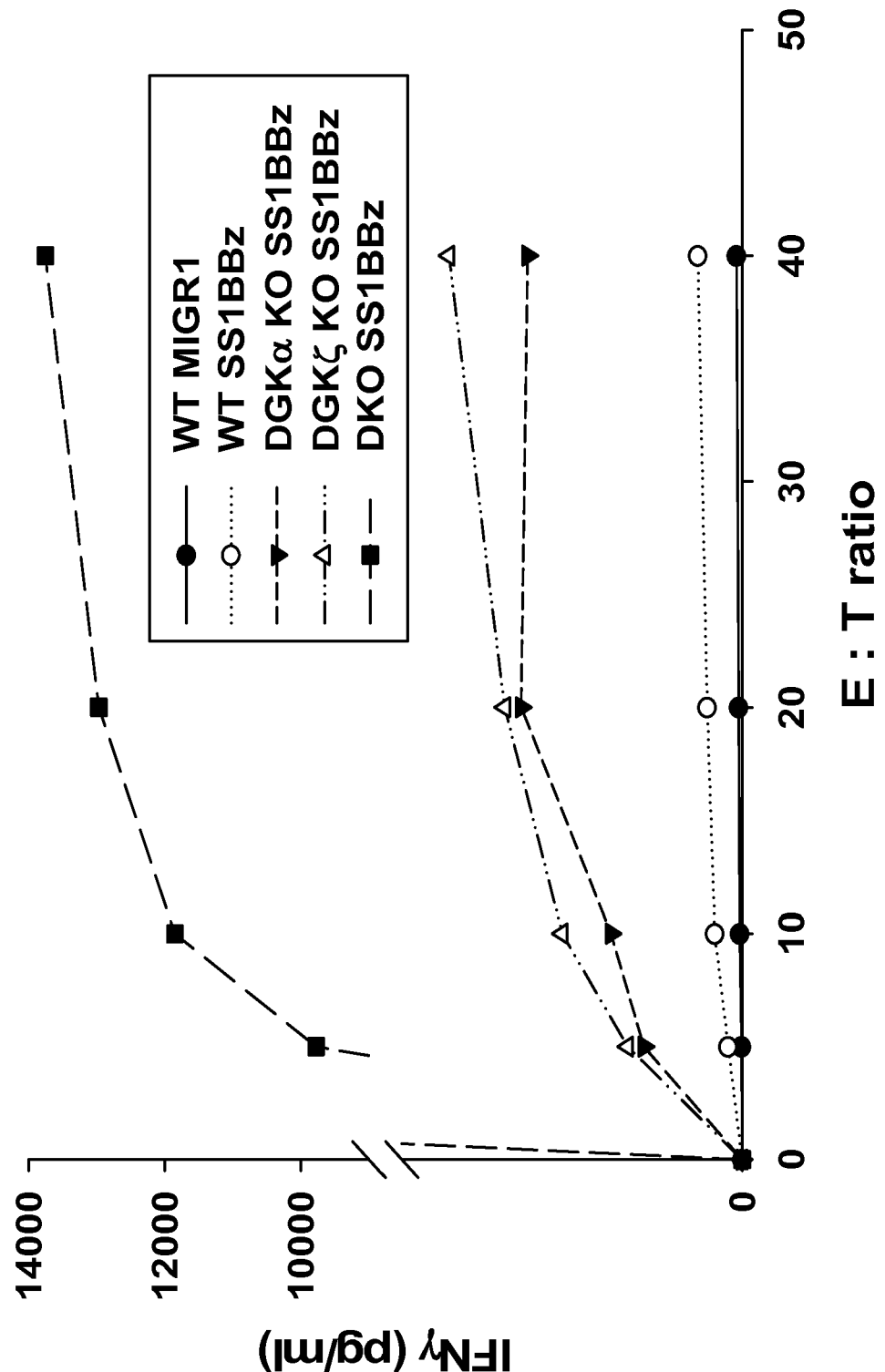
FIG. 6 is a graph depicting INFγ release by T cells induced by tumor cells.
Figure 7:
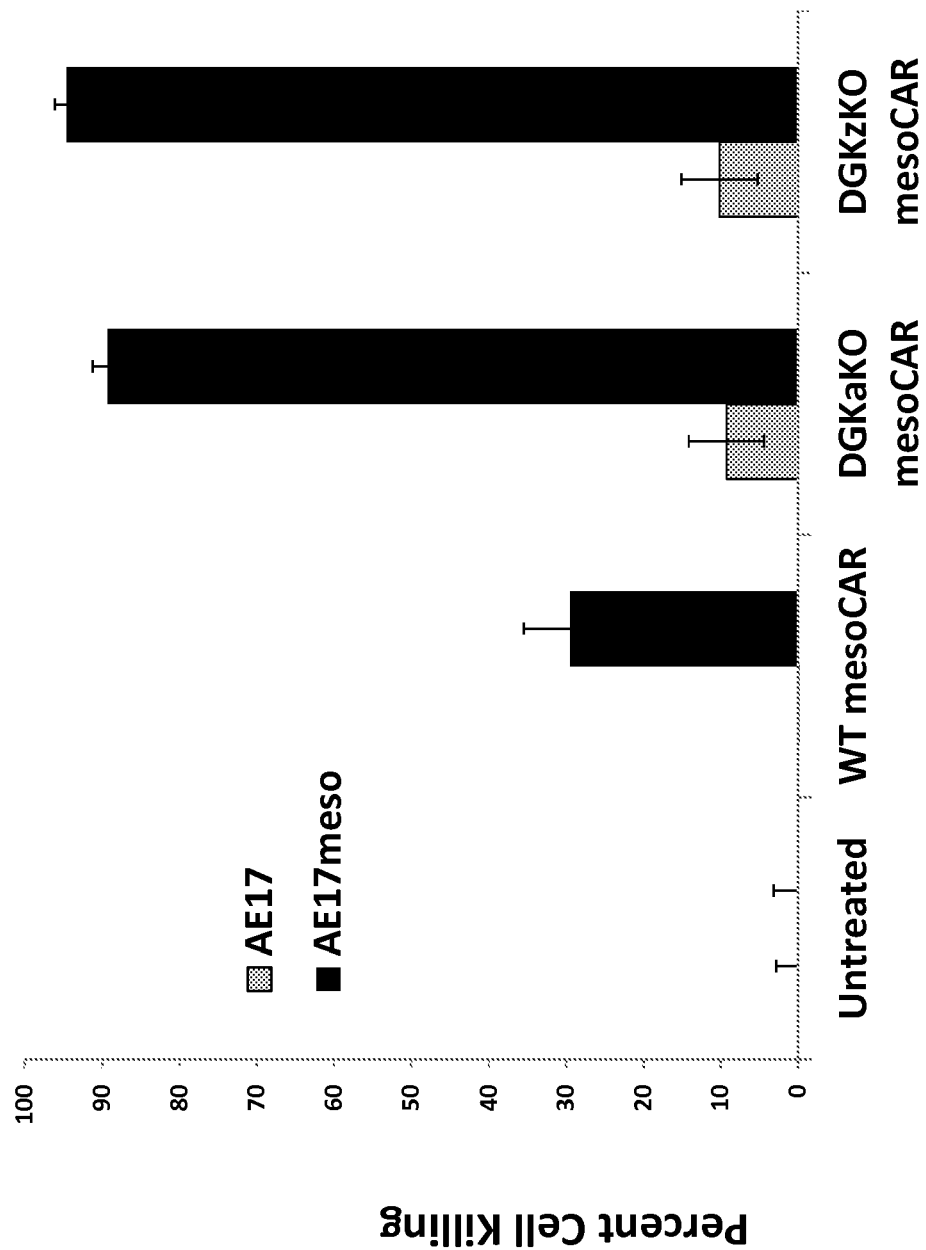
FIG. 7 is a graph depicting the killing of tumor cells by wild type and DGK knockout meso-CAR T cells.

Loss of DGKζ, DGKα or Both Markedly Enhanced the Ability of the T Cells to Kill Tumor Cells Unexpectedly, loss of DGKζ, DGKα or both markedly enhanced the ability of the T cells to kill tumor cells (FIGS. 4 and 5) and substantially increased the amount of IFNγ released (FIG. 6). Thus, at a ratio of 40 T cells to one tumor cell, the standard CAR T cells killed about 15-20% of the tumors. This killing rate was nearly triple (90-95%) in the DGKα or DGKζ KO T cells. The CAR T cells in the double knockout (DKO) cells (lacking both isoforms of DGK) were able to kill 90% of the tumor cells. The DKO cells had activity at a very low E:T ratio (1:5), while killing was not seen at this ratio with the control CAR T cells. A similar synergy was seen in IFNγ release. FIG. 7 shows that when incubated at a 20:1 ratio for 20 hours, T cells from DGK knockout mice significantly increased killing compared to wild type. Furthermore, the AE17 cells were not killed (FIG. 7).

Figure 8:
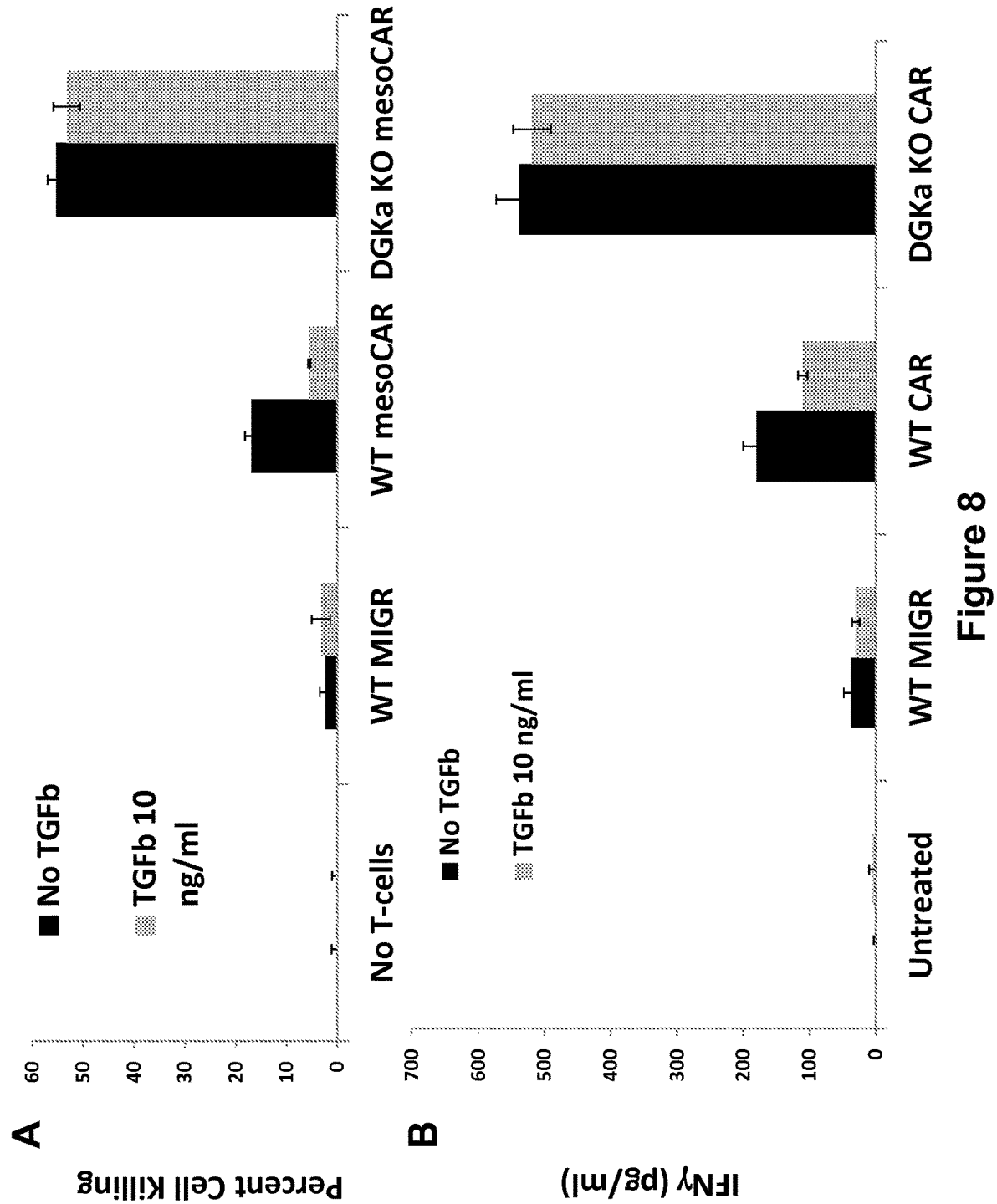
FIG. 8, comprising

It was also observed that elimination of DGK made T-cells less sensitive to TGFβ-mediated-inhibition of tumor killing. As shown in FIG. 8A, when WT-mesoCAR T cells are exposed to TGFβ, their ability to kill tumor cell is decreased by more than 60%. However, TGFβ had virtually no effect on the ability of DGKα KO cells to kill tumor cells. It was also observed that TGFβ decreased the amount of IFNγ that was released (FIG. 8B). This was also blunted in the DGKα cells. These effects are likely to be important in a therapeutic context since tumors make large amounts of TGFβ.

Figure 9:
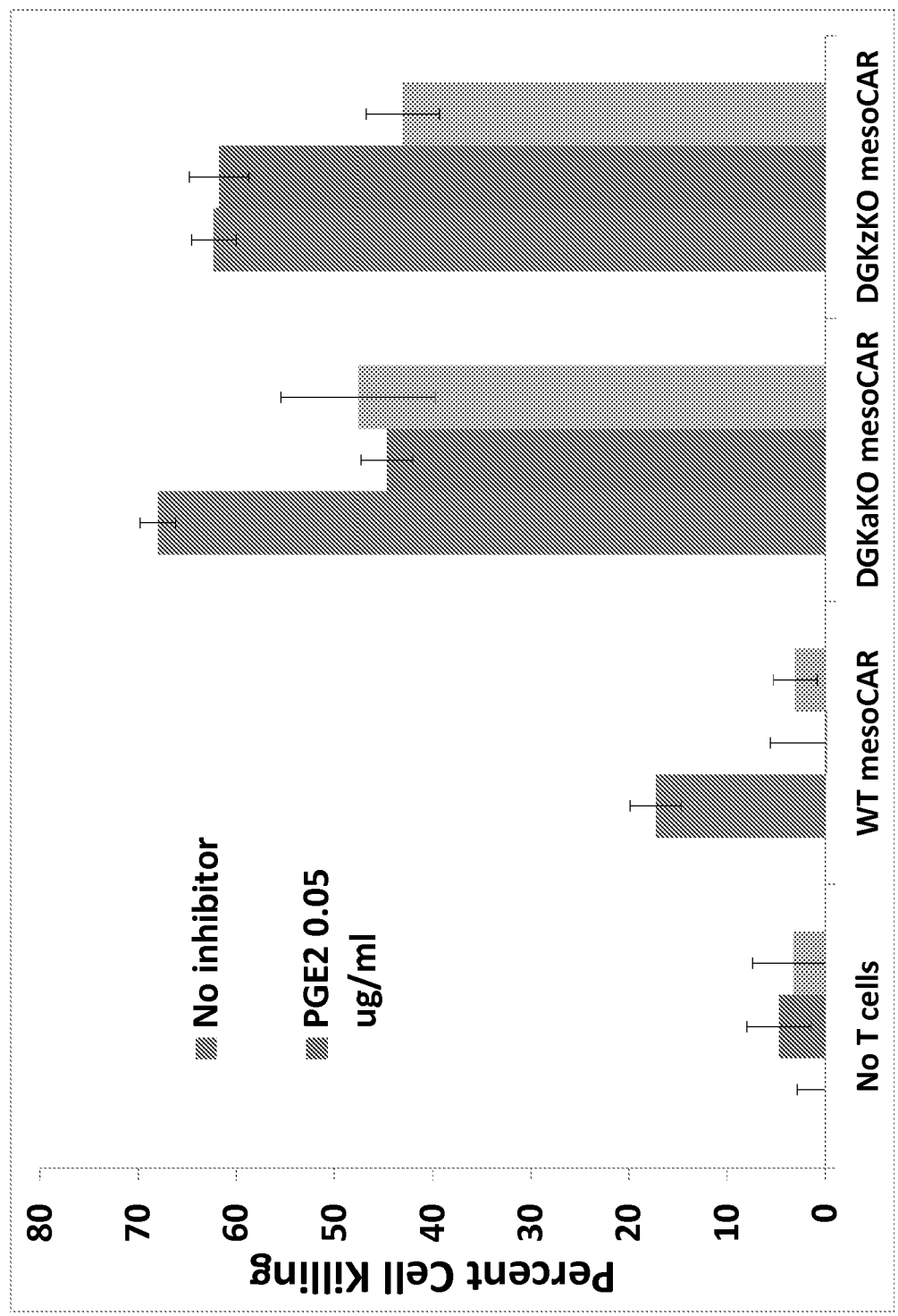
FIG. 9 is a graph depicting the effect of DGK knockout cells on preventing tumor growth. The results of the WINN assay were collected two weeks post-injection.
Figure 10:
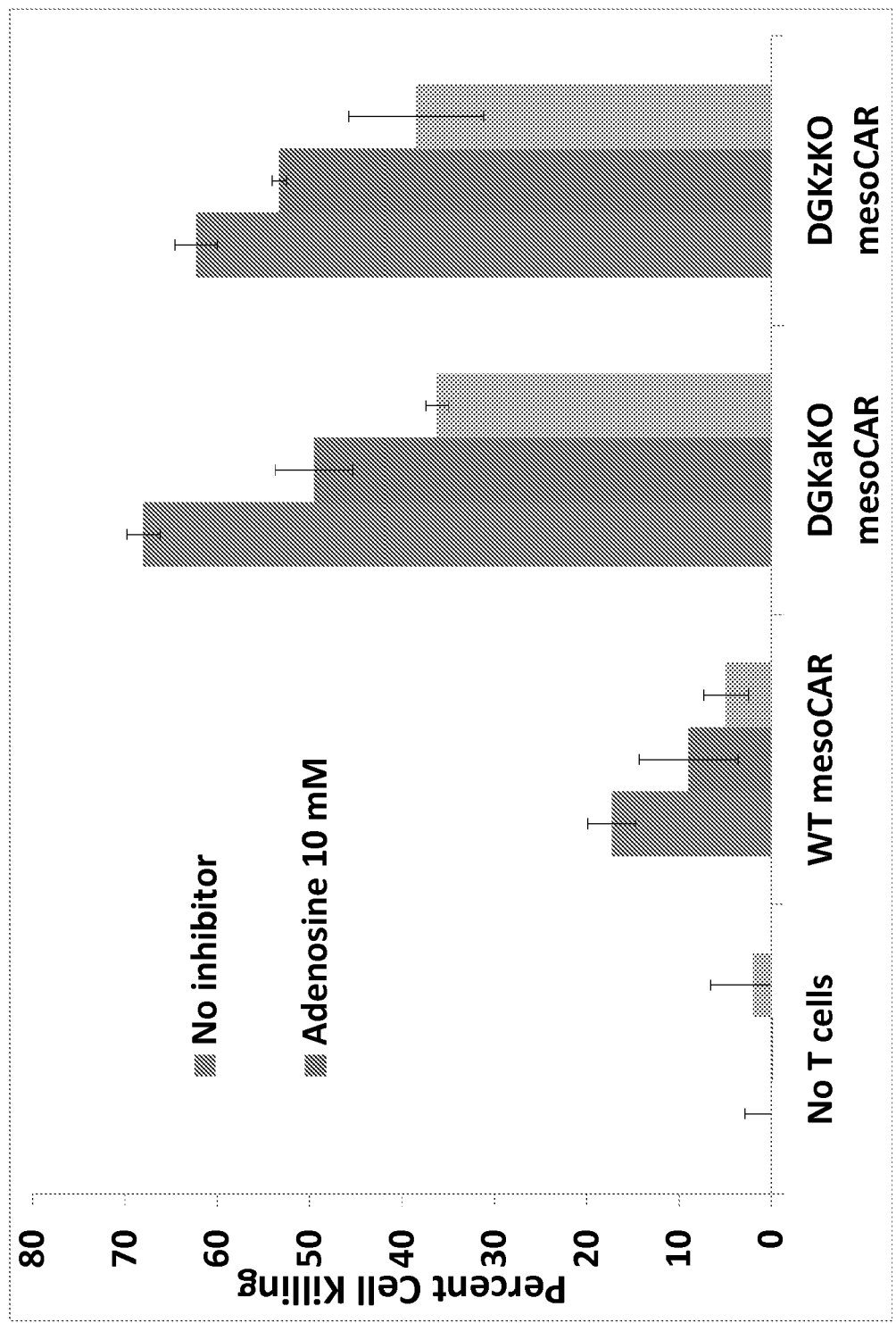
FIG. 10 is a graph depicting the effect of DGK knockout cells on preventing tumor growth, when using an E:T ratio of 1:10.

It was also observed that elimination of DGK made T-cells less sensitive to PGE2 and adenosine-mediated inhibition of tumor killing. As shown in FIG. 9, when WT-mesoCAR T cells are exposed to PGE2, their ability to kill tumor cell was almost completely inhibited. However, PGE2 inhibited the ability of DGKα KO or DGKz KO cells to kill tumor cells by only about 30%. Very similar results are shown in FIG. 10, where the ability of adenosine to inhibit tumor cell killing is markedly blocked in the KO cells. These effects are likely to be important in a therapeutic context since tumors make large amounts of adenosine and PGE2 which inhibit T cell function.

Figure 11:
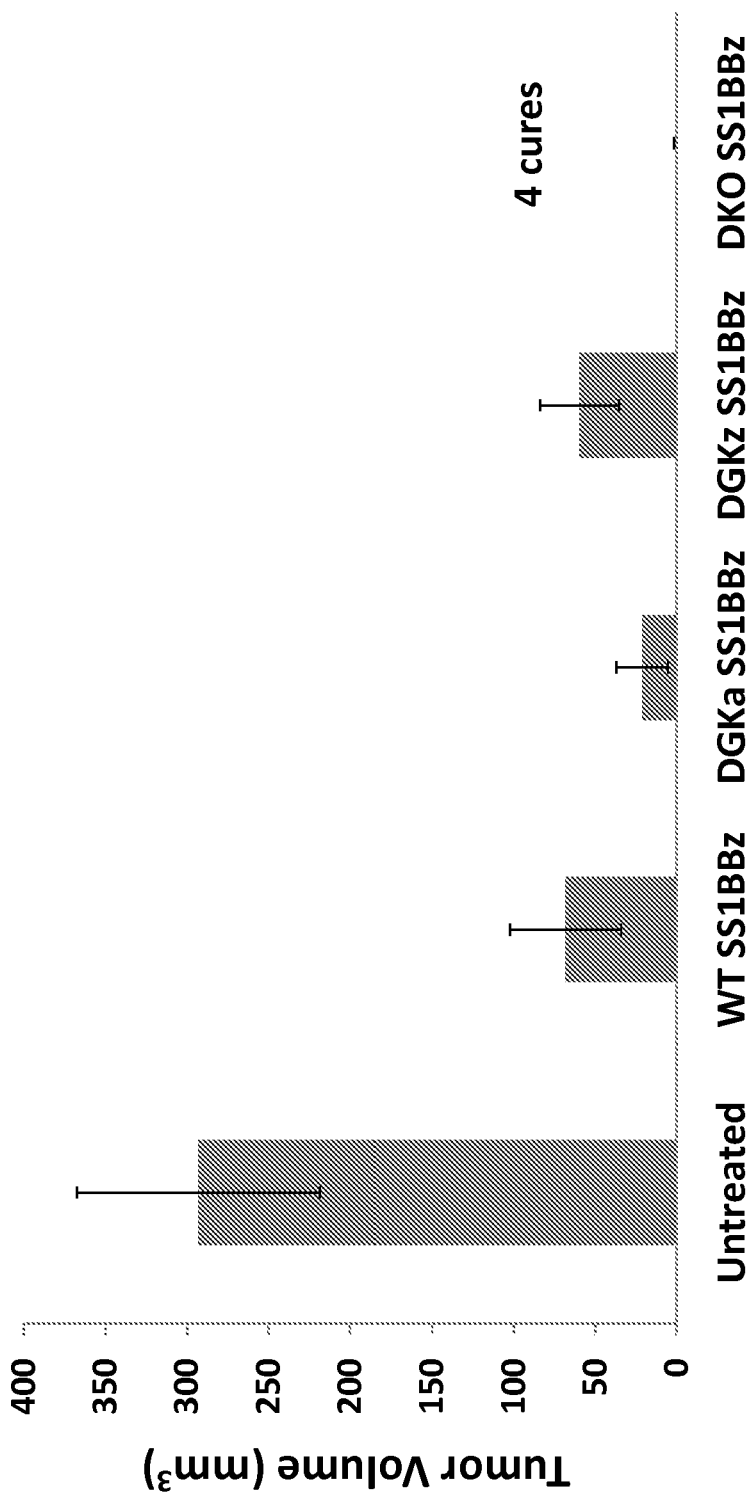
FIG. 11 is a graph depicting the results of an intratumoral injection study. The results comprise tumor measurements tabulated four days post-T cell injection.
Figure 12:
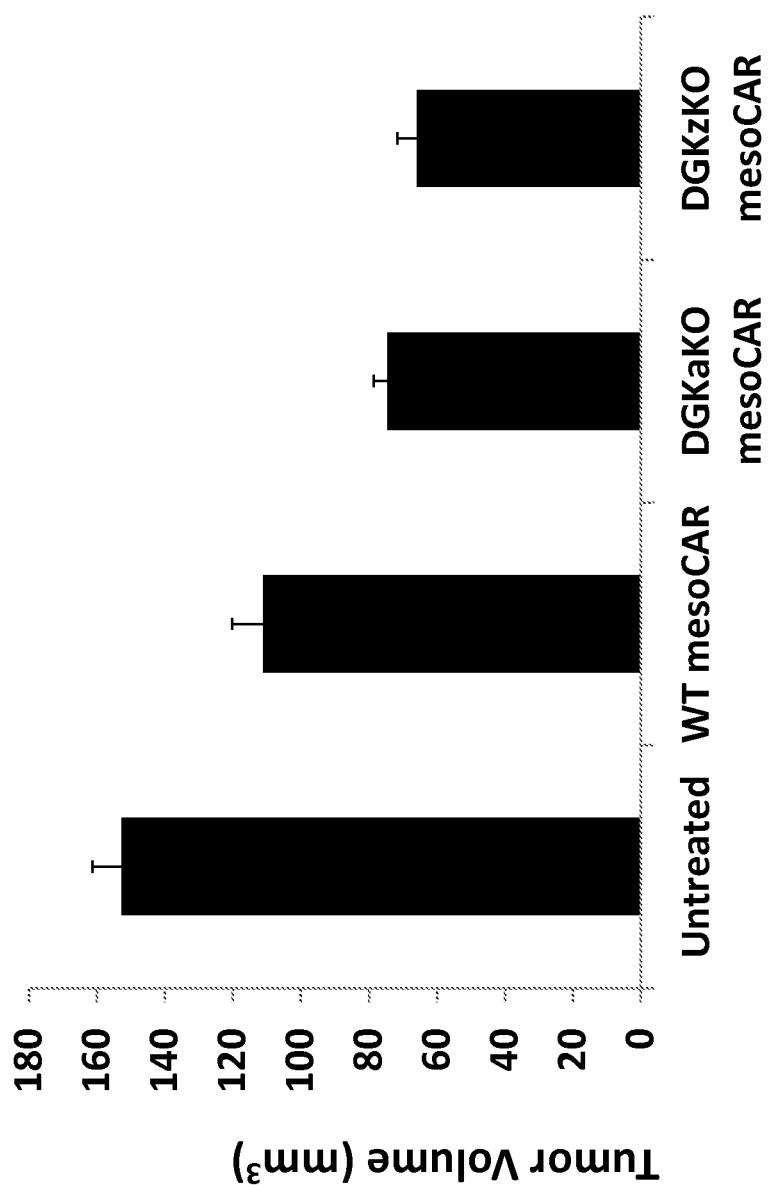
FIG. 12 is a graph depicting the effect of DGK inhibitors on the killing activity of human CAR-T cells (TIL) extracted from a tumor in an animal model.

To determine the impact of DGK loss in an in vivo context, equal numbers of each type of wild type and DGK knockout T cells were mixed with mesothelin-expressing tumor cells, which were then injected into the flanks of B6 mice. Measuring the tumor sizes at 2 weeks provided an estimation of the killing efficacy of the T cells. FIG. 11 shows that while all of the T cells inhibited tumor growth, DGK KO cells were far more effective. The DKO cells actually cured all of the mice of tumors. Even when a very low ratio of T cells to tumor cells was used (1 T cell to 10 tumor cells) WT CAR inhibited growth by about 24%, while both types of DGK KO T cells inhibited tumor growth by nearly twice as much (43-46%) (FIG. 12).

Figure 13:
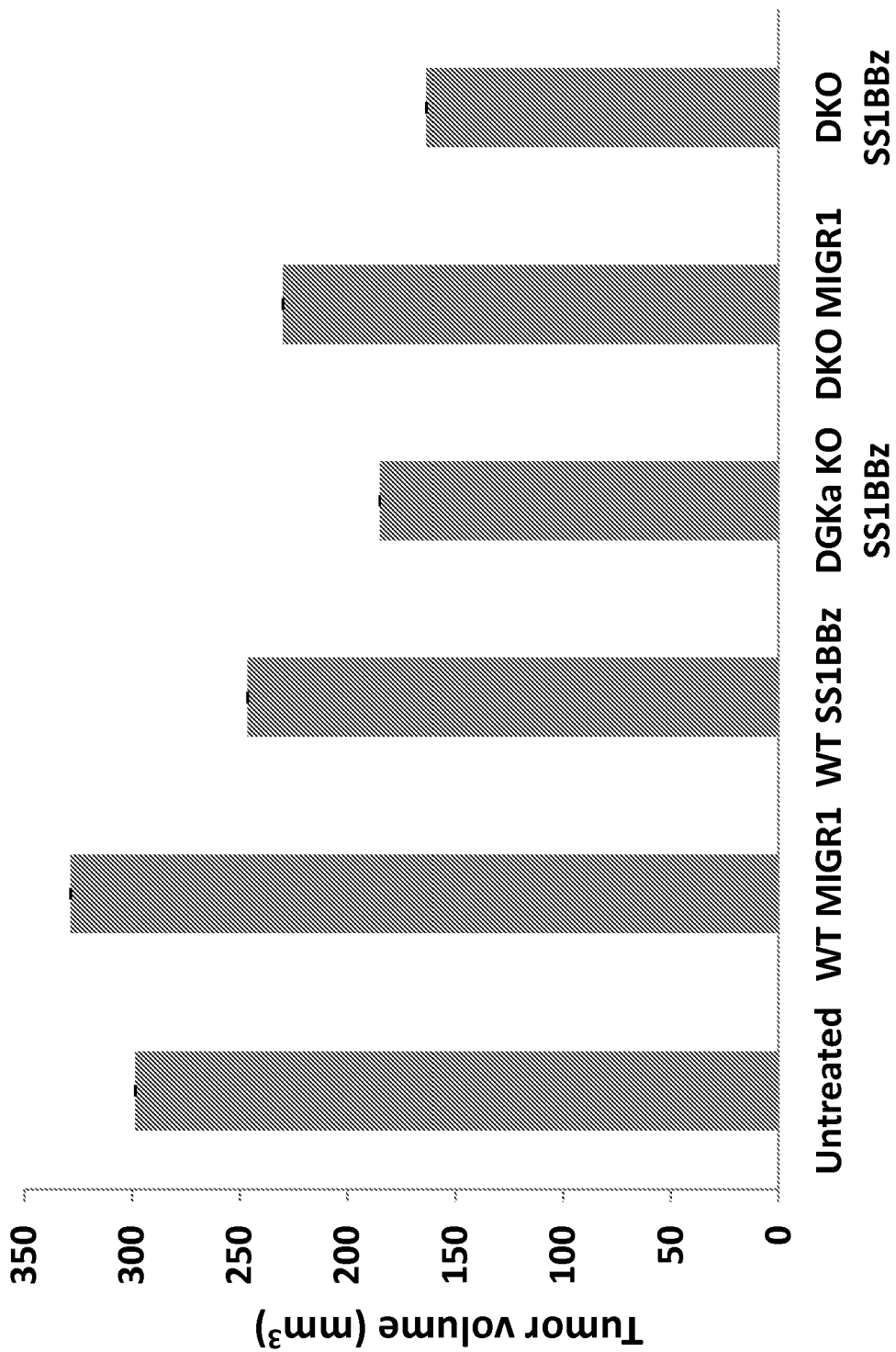
FIG. 13 is an image demonstrating that various types of T cells were injected intratumorally and the size of tumors were measured after 4 days. The DGKα knockout and DKO cells were more effective in reducing tumor size.

In another experiment, various types of T cells were injected intratumorally, and the size of tumors measured after 4 days. As shown in FIG. 13, the DGKα knockout and DKO cells were more effective in reducing tumor size.

Figure 14:
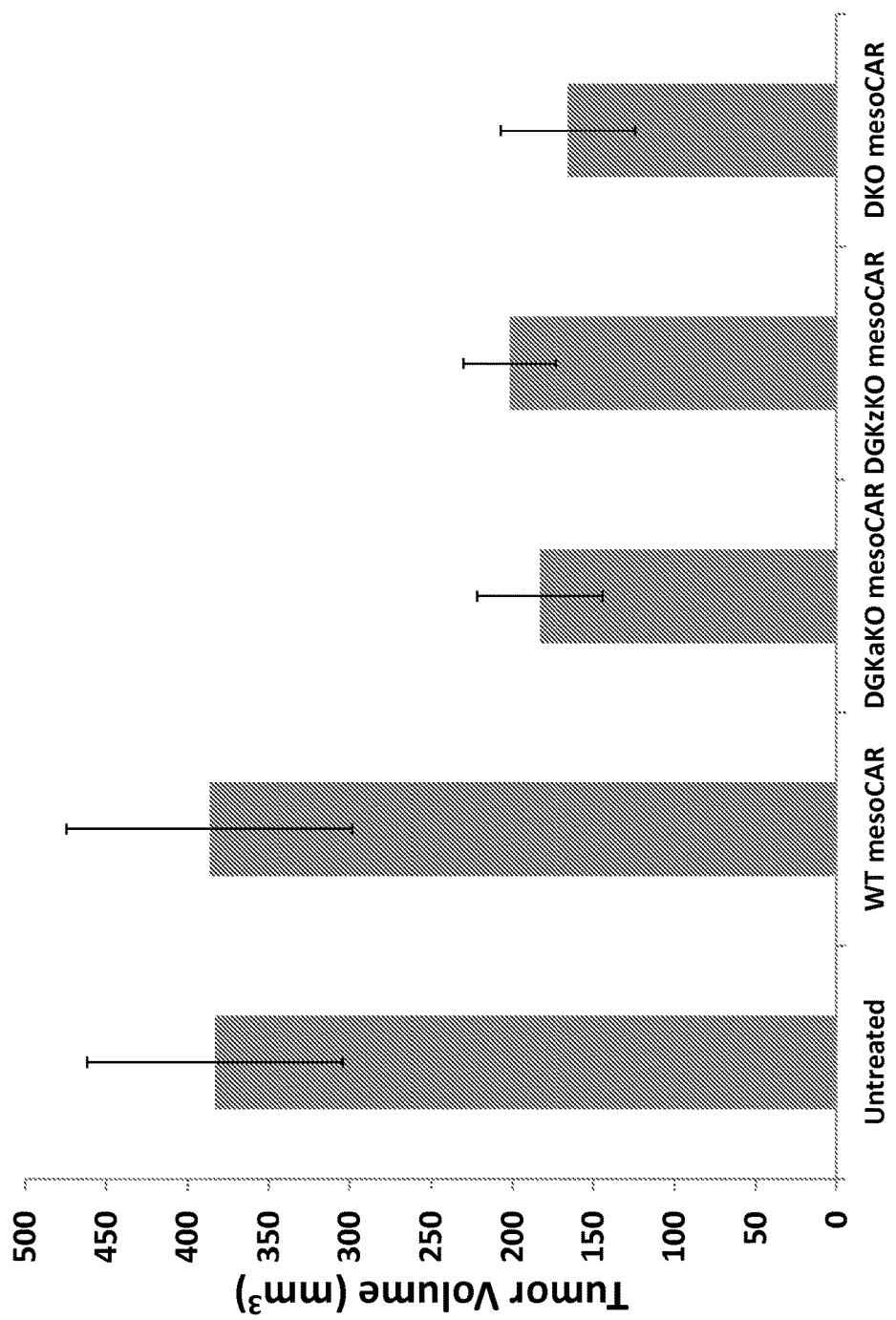
FIG. 14 is an image demonstrating that mice with established tumors were injected intravenously with $10^7$ wild type T cells or the three types of DGK knockout T cells. Whereas the wild type meso-CAR T cells had no real antitumor effect, all three types of KO T cells reduced the tumor size by about 50%, showing they have much more anti-tumor activity than WT CAR T cells.
Figure 15:
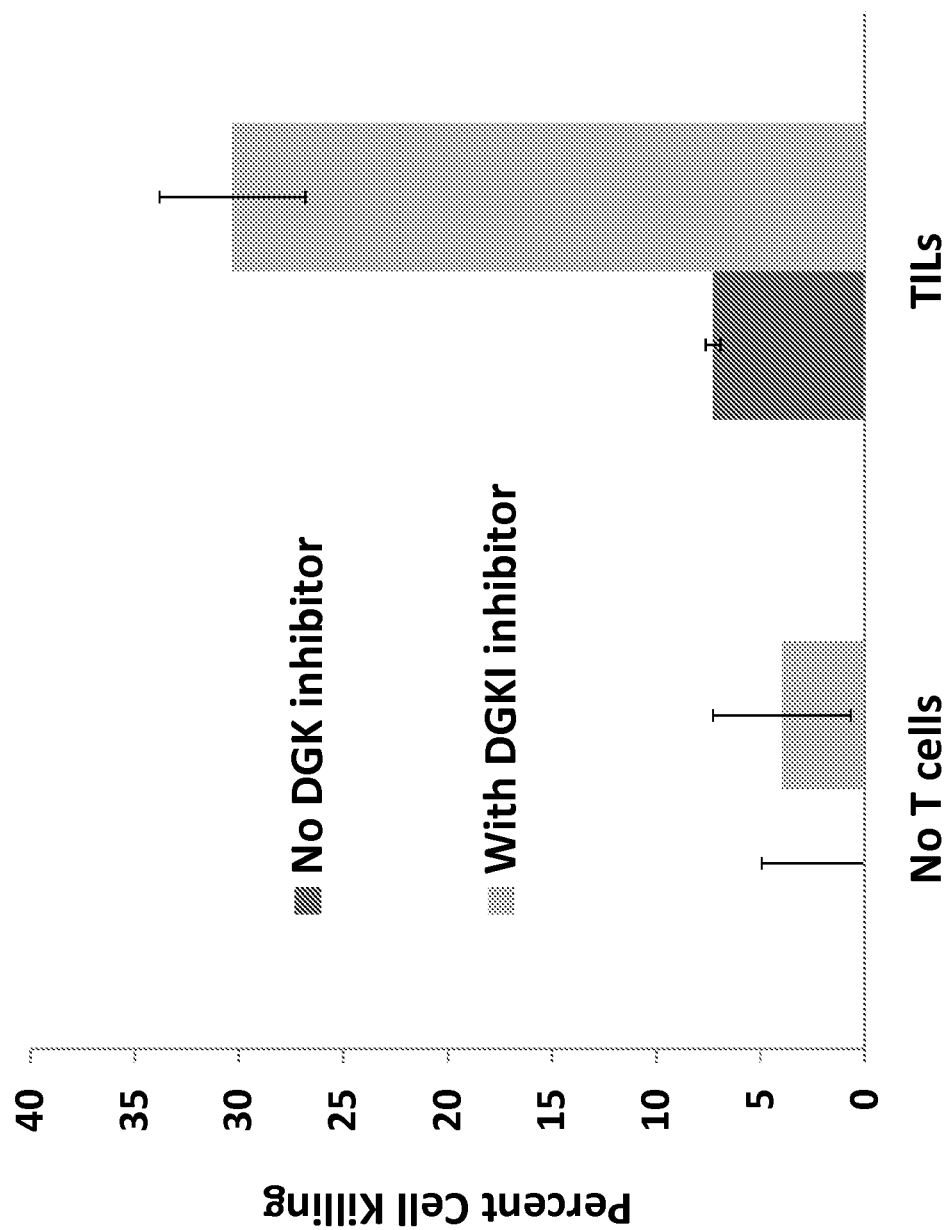
FIG. 15 is an image demonstrating the percent cell killing by tumor infiltrating lymphocytes (TILs) in the presence and absence of DGK inhibitor.

In addition, experiments were conducted to mimic potential human trials in which mice with established tumors were injected intravenously with $10^7$ wild type T cells or the three types of DGK knockout T cells. As shown in FIG. 14, whereas the wild type meso-CAR T cells had no real antitumor effect, under these conditions, all three types of KO T cells reduced the tumor size by about 50%, showing they have much more anti-tumor activity than WT CAR T cells. Preliminary relevant observations in human CAR T cells have been recorded using a commercially available DGK inhibitor (R59022). Human mesothelin-CAR T cells mixed with human mesothelin tumor cells (at a 1:1 ratio) were injected into immunodeficient mice. The tumor growth was slowed, but not prevented by the CAR-T cells. After 2-3 weeks, tumors were harvested and the human CAR-T cells were purified. When these T cells (Tumor infiltrating lymphocytes, or TILs) are allowed to react with fresh tumors, they can kill only 5-10% of the tumor cells showing they are hypofunctional compared to freshly made CAR-T cells which kill 70% of tumor cells (FIG. 15). Although this inhibitor is not entirely specific, and not wishing to be bound by any particular theory, these data support the idea that inhibiting DGK in human CAR-TIL augments function. As described above, these data are very similar to that seen in human TIL (Prinz et al., 2012, J. Immunol. 188:5990-5600).

In another study, a human codon-optimized version of a dominant negative (DN) DGKα with insertion of a myc tag and the proper restriction sites can be placed into a bicistronic lentiviral vector with a CAR, and used to transfect human T cells. The presence of the DN construct can be confirmed using the myc-tag. Effective knockdown of DGK can be confirmed by showing increased active ras production and presumably increased phospho-ERK. After in vitro assays, the signaling, cytokine release, and tumor killing ability of the CAR-DGK DN T cells can be tested and compared to CAR T cells.

The CAR-DGK DN T cell TILs show enhanced signaling and cytokine release when exposed to antigen coated beads and enhanced antigen specific tumor killing. Enhanced anti-tumor activity can be seen in the animal models. The CAR-TILs isolated can be less hypofunctional with improved cytokine release and killing when exposed to fresh tumor cells.

A siRNA/shRNA approach can also be undertaken. Validated siRNAs and shRNAs for DGKα are commercially available from Origene, Santa Cruz, and other companies. These can be tested in the CAR-T cells using anti-DGKα staining and the most effective CAR-T cells subcloned into the lentiviral vector with the H1 promoter (An et al., 2006, Mol. Ther. 14:494-504). Zinc finger nucleases can also be used to inhibit DGKα activity.

As described herein, it was observed that that loss or blockade of DGK isoforms augments efficacy of adoptive T cell transfer. DGK inhibitors or genetic reduction of DGK (using, for example, shRNA or zinc-finger nucleases) can be used to augment the efficacy of adoptive transfer of human T cells (containing CARs or transgenic T cell receptors) by increasing their effector function. This would include, but is not limited to, blood T cells, cord blood T cells, bone marrow T cells, and T cells derived from iPSC. This technology may be used to enhance efficacy of T cells for use in tumors and to enhance response in chronic infections such as Hepatitis C virus and HIV virus.

Example 2: Enhanced Effector Responses in Activated CD8+ T Cells Deficient in Diacylglycerol Kinases Recent clinical trials have shown promise in the use of chimeric antigen receptor (CAR)-transduced T cells; however, augmentation of their activity may broaden their clinical use and improve their efficacy. Since CAR action requires proteins essential for T-cell receptor (TCR) signal transduction, it was examined herein whether deletion of negative regulators of these signaling pathways would enhance CAR signaling and effector T-cell function.

For the studies presented herein, it was chosen to target an inhibitor of diacylglycerol (DAG), an essential second messenger that is created by the cleavage of phosphatidyl (4,5) inositol bisphosphate by phospholipase Cγ1 (PLCγ1) after PLCγ1 is phosphorylated and activated by the protein tyrosine kinases that are recruited to the stimulated TCR (Smith-Garvin et al., 2009, Annu Rev Immunol 27:591-619). DAG activates signaling molecules leading to several second messenger cascades, most notably the Ras/ERK pathway that is known to be essential for T-cell activation (Dower et al., 2000, Nat Immunol 1:317-21). After its generation, DAG is actively metabolized into phosphatidic acid by one of the 2 isoforms of diacylglycerol kinases (DGK) present within T cells, DGKα or DGKζ (Topham & Prescott, 2001, J Cell Biol 152:1135-43). Previously, it has been observed that deletion of either DGK isoform potentiates DAG-mediated Ras and extracellular signal-regulated kinase (ERK) activation and augments TCR-induced cytokine production and T-cell proliferation (Zhong et al., 2003, Nat Immunol 4:882-90; Zha et al., 2006, Nat Immunol 7:1166-73; Olenchock et al., 2006, Nat Immunol 7:1174-81). Further, it has been found that deletion of DGK results in improved CD8+ T-cell responses by augmenting signaling via the TCR when mice are challenged with a transplantable subcutaneous tumor (Riese et al., 2011, J Biol Chem 286: 5254-65). However, neither the absence of DGKα or DGKζ is sufficient to enable a completely successful antitumor response. It is examined here whether combining CAR therapy with DGK deficiency might boost the ability of T cells to respond to a tumor challenge. The data presented herein demonstrates this augmentation, suggesting that such a combined therapeutic approach may have use in future clinical trials.

The materials and methods employed in these experiments are now described.

Mice

Mice deficient in dgkα, dgkζ, or both backcrossed to C57Bl/6 have been described previously (Zhong et al., 2003, Nat Immunol 4:882-90; Olenchock et al., 2006, Nat Immunol 7:1174-81). C57Bl/6 mice containing a transgene for the OVAp TCR (OT-I mice) were obtained from the Jackson Laboratories. DGKζ-deficient CD45.2 CD90.2 OT-I mice were created by backcrossing these 2 strains. All experiments were carried out in mice 6 to 12 weeks old.

*Listeria* Infection and EL4-Ova Tumor Model Experiment

Splenic CD8+ T cells were isolated from wild-type or DGKζ-deficient CD45.2 CD90.2 OT-I mice by flow cytometry (CD8+ CD44$^{lo}$) as described (Riese et al., 2011, J Biol Chem 286:5254-65). Twenty thousand cells were transferred intravenously into CD45.2, CD90.1 recipient mice subsequently infected intravenously with 5,000 cfu *Listeria*-ova 24 hours after T-cell transfer. One week later, CD45.2+ donor cells were isolated from spleens of recipient mice according to the manufacturer's instructions (Miltenyi Biotec), and $1.5 \times 10^6$ of isolated cells were transferred intravenously into CD45.1, CD90.2 mice that had been inoculated with $2.5 \times 10^5$ EL4-ovalbumin (EL4-ova) tumor cells, a murine lymphoma line that stably expresses ovalbumin (Moore et al., 1988, Cell 54:777-85), in the right flank 2 weeks prior. Tumors were barely palpable at time of T-cell transfer. One week later, mice were euthanized, tumor size was measured, and T cells from spleens and tumors were analyzed.

T-Cell Transduction

MesoCAR, a fusion protein that contains the antigen-binding region of an antibody specific for the human tumor antigen mesothelin fused with CD8α transmembrane domain, CD3ζ, and the costimulatory domain of 4-1BB, has been described previously (Moon et al., 2011, Clin Cancer Res 17:4719-30). cDNA encoding mesoCAR was subcloned into the MIGR retrovirus (Pear et al., 1993, Proc Natl Acad Sci USA 90:8392-6), which also expresses GFP using an internal ribosomal entry site. The sequence of antimesothelin Fv was provided (Chowdhury & Pastan, 1999, Nat Biotechnol 17:568-72). Infective particles were generated from the supernatants of 293T cells transfected with retroviral vector plasmid and helper plasmids using Lipofectamine 2000 (Invitrogen), as previously described (Jordan et al., 2006, J Immunol 176:2430-8). Primary murine T cells were isolated as suggested by the manufacturer (Miltenyi Biotec) from the spleens of wild-type or DGK-deficient mice and incubated in 24-well plates [$4 \times 10^6$ cells/well in 2 mL T-cell media with 100 U/mL interleukin (IL)-2] coated with α-CD3 (1 µg/mL) and α-CD28 (2 µg/mL). After 48 hours, cells ($1 \times 10^6$ cells/well) were mixed with retrovirus (1 mL crude viral supernatant) in a 24-well plate coated with Retronectin (50 µg/mL; Clontech) and centrifuged without braking at room temperature for 30 minutes at 1,200 g. After overnight incubation, cells were expanded with 50 U/mL of IL-2 for 48 hours.

Coating Beads with Recombinant Human Mesothelin

Target antigens were chemically crosslinked to tosylactivated 4.5 µm Dynabeads (Invitrogen, #140-13), using the manufacturers' instructions. In brief, $4 \times 10^7$ beads were incubated 16 to 18 hours at 37° C. in the presence of 20 µg of recombinant human mesothelin (RayBiotech, #230-00043) in 0.1 mol/L sodium phosphate buffer (pH 7.4) with shaking. After incubation, beads were washed and resuspended in PBS containing 0.5% bovine serum albumin to a final volume of 1 mL.

Evaluation of CAR T-Cell Effector Functions

Cytotoxicity and IFN ELISA

A stable cell line of the mouse mesothelioma line AE17 expressing human mesothelin subsequently engineered to express luciferase has been described (Moon et al., 2011, Clin Cancer Res 17:4719-30; Tchou, et al., 2012, Breast Cancer Res Treat 133:799-804). Cytokine release assays were conducted by co-culture of T cells with target cells at the described ratios, in triplicate, in 96-well round bottom plates in 200 µL. After 18 hours, cell lysis was determined from the detection of luciferase from the remaining cells using a previously described assay (Moon et al., 2011, Clin Cancer Res 17:4719-30). An ELISA Kit (Biolegend) was used to measure IFN-γ.

WINN Assay

A total of $1 \times 10^6$ mesothelin-expressing TC1 cells, a murine non-small cell lung cancer line with well-established use in the WINN assay (DeLong et al., 2003, Cancer Res 63:7845-52), were coinjected into the right flank along with $2 \times 10^5$ CAR-transduced T cells (routinely 50% of which were gfp positive, and thus transduced with CAR). Ten days later, mice were euthanized, and tumor volume was assessed.

Intravenous Transfer of CAR-T Cells in Mice with Pre-existing Tumor

C57Bl/6 mice were inoculated subcutaneously with $2 \times 10^6$ AE17 meso cells. Seven days later, at which point tumors were approximately 100 mm$^3$, mice were injected with $1 \times 10^7$ CAR-transduced T cells intravenously by tail vein. Tumor development was monitored by caliper measurement of tumor diameter over an additional 10 days. Each volumetric determination was derived from the formula 0.52a$^2$b, with a representing the minor axis and b representing the major axis. Alternately, mice were sacrificed at 3 or 6 days after transfer, and the presence of T cells within spleen or tumor was determined by evaluating for gfp expression within T-cell subsets by flow cytometry.

Expression of Cytotoxic Markers Following CAR Activation.

A total of $2\times10^6$ mesoCAR-T cells derived from mouse splenocytes replete or deficient in DGKs were placed in individual wells of a 24-well plate with or without $2\times10^6$ mesothelin-coated beads for 18 hours, at 37° C. in the presence of 30 U/mL of IL-2. After incubation, T cells were stained for the presence of the surface markers TRAIL (eBioscence, #12-5951-82) or FasL (eBioscience, #12-5911-81), or the intracellular markers granzyme B (BD, #51-2090KZ) or perforin (eBioscience, #12-9392-82), using protocols described by the manufacturer. Flow cytometry histograms of marker expression were evaluated from cells that were positive for gfp (indicating expression of CAR) and CD8, and negative for CD4.

T-Cell Immunoblotting and CD69 Upregulation

To assess for Erk phosphorylation, $1\times10^6$ mesoCAR-transduced T cells were incubated either with mesothelin- or albumin-coated beads in a 1:4 ratio (cells:beads), or with α-CD3ε antibody at 2.5 µg/mL final concentration for indicated time points. Lysates were prepared and immunoblotted for phosphorylated Erk, total Erk, or tubulin (antibodies all from Cell Signaling) as previously described (Riese et al., 2011, J Biol Chem 286:5254-65). Alternately, protein-bead stimulations were allowed to proceed for 5 hours, and then the surface upregulation of CD69 was determined by flow cytometry.

Primary Human CAR-T-Cell Assays

Primary human T cells were obtained and mock infected or transduced with lentivirus expressing mesoCAR as previously described (Moon et al., 2011, Clin Cancer Res 17:4719-30). A total of $5\times10^6$ T cells were subsequently added to 24-well plates that had been seeded with $5\times10^5$ cells either from the epithelial mesothelioma (EM) human mesothelioma line or a stable derivative cell line, EM-meso, engineered to express high levels of mesothelin, in a 24-well dish. After 96 hours of coincubation (which included the addition of another $3\times10^5$ EM or EM-meso cells at the midpoint of coincubation), cells were resuspended, and T cells were isolated via Lymphoprep density gradient separation (Axis-Shield) as suggested by the manufacturer. Cells were assessed for viability using Trypan blue, and $1\times10^5$ live T cells were cocultured with $5\times10^3$ EM-meso-luc cells expressing luciferase in 96-well plates in the presence or absence of the DGK inhibitors DGK1 (R59022) or DGK2 (R59949; Sigma) at 5 µg/mL. After 18 hours, remaining tumor cells were washed and lysed, and luminescence was evaluated. Cell lysate determinations were corroborated with visual estimate of remaining numbers of tumor cells.

For studies with TGFβ, $1\times10^5$ primary human T cells that had been mock infected or transduced with lentivirus-expressing mesoCAR were coincubated with $5\times10^3$ EM-meso-luc cells in the presence of indicated concentrations of TGFβ for 18 hours, and cell numbers were determined as described above.

The results of experiments are now described.

DGKζ-Deficient Activated CD8+ T Cells Show Enhanced Response to Tumor

Figure 16:
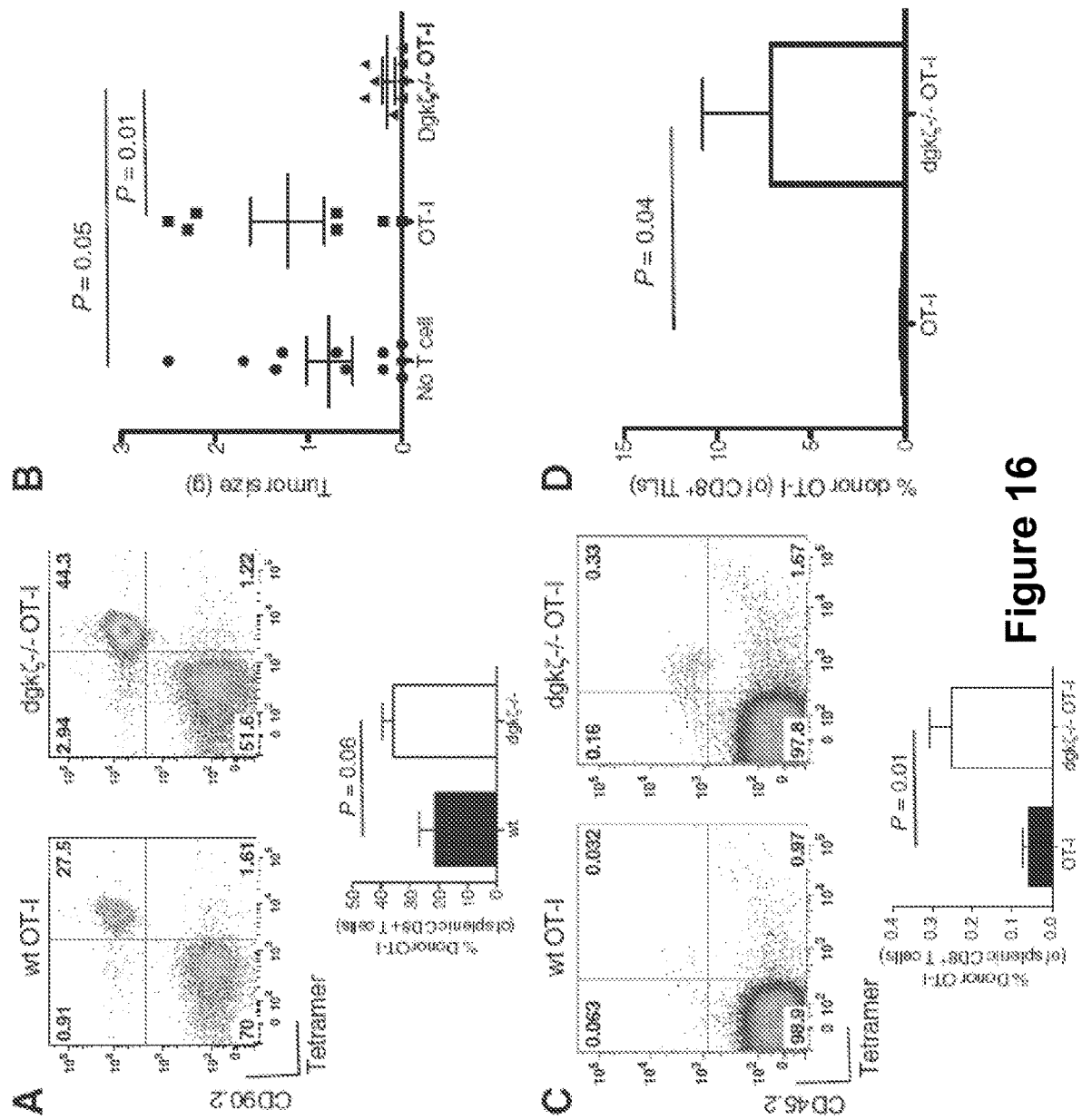
FIG. 16, comprising

It has been previously shown that naïve DGKζ-deficient CD8+ T cells specific for ovalbumin (OT-I cells) are better able to control tumor growth and undergo activation than naïve wild-type OT-I cells after transfer into mice bearing EL4-ova-expressing tumors (Riese et al., 2011, J Biol Chem 286:5254-65). However, in those studies, implanted tumors were not completely eradicated. It was examined herein whether the effect of DGKζ deletion would be improved if, instead of naïve T cells, activated T cells were used, which could potentially confer a more robust antitumor response. In addition, this approach would more closely mirror current clinical trials of adoptive CD8+ T-cell tumor immunotherapy that use cells preactivated before transfer. To generate uniform populations of activated cells, naïve OT-I cells sufficient or deficient in DGKζ were transferred into congenically marked mice, and the recipient animals were then infected with Listeria engineered to express ovalbumin. One week later, antigen-experienced (CD44-high) donor OT-I cells were recovered from spleens and transferred into EL4-ova tumor-bearing mice. Initially, it was noted that expansion of naïve DGKζ-deficient OT-I cells was more robust when compared with naïve wild-type OT-I cells in response to the antigenic challenge with Listeria-ova (FIG. 16A), as in other DGKζ-deficient CD8+ T cell-models of acute infection (Zhong et al., 2003, Nat Immunol 4:882-90; Riese et al., 2011, J Biol Chem 286:5254-65); however, there was no difference in activation phenotype of the recovered cells as assessed by CD44 expression between the 2 different genotypes. After transfer of equal numbers of wild-type or DGKζ-deficient effector cells into EL4-ova tumor-bearing mice, it was found that although wild-type OT-I cells conferred no appreciable antitumor effect, tumors in mice treated with DGKζ-deficient activated OT-I cells were significantly (P=0.05) reduced in size compared with untreated animals (FIG. 16B). DGKζ-deficient effector cells also persisted in increased numbers within the spleen of host animals (FIG. 16C) and were observed in larger quantities within the tumors of host animals (FIG. 16D). These data show that deficiency of DGK confers enhanced antitumor potential in preactivated T cells. As in previous studies with naïve DGKζ-deficient OT-I CD8+ T cells, however, it was found that transfer of activated DGKζ-deficient CD8+ T cells was insufficient to completely eradicate tumors, suggesting that the strategy of targeting DGK alone is insufficient in curtailing the progression of established tumors.

Deletion of DGKζ Enhances Functional Responses of T Cells Downstream of CARs

Figure 17:
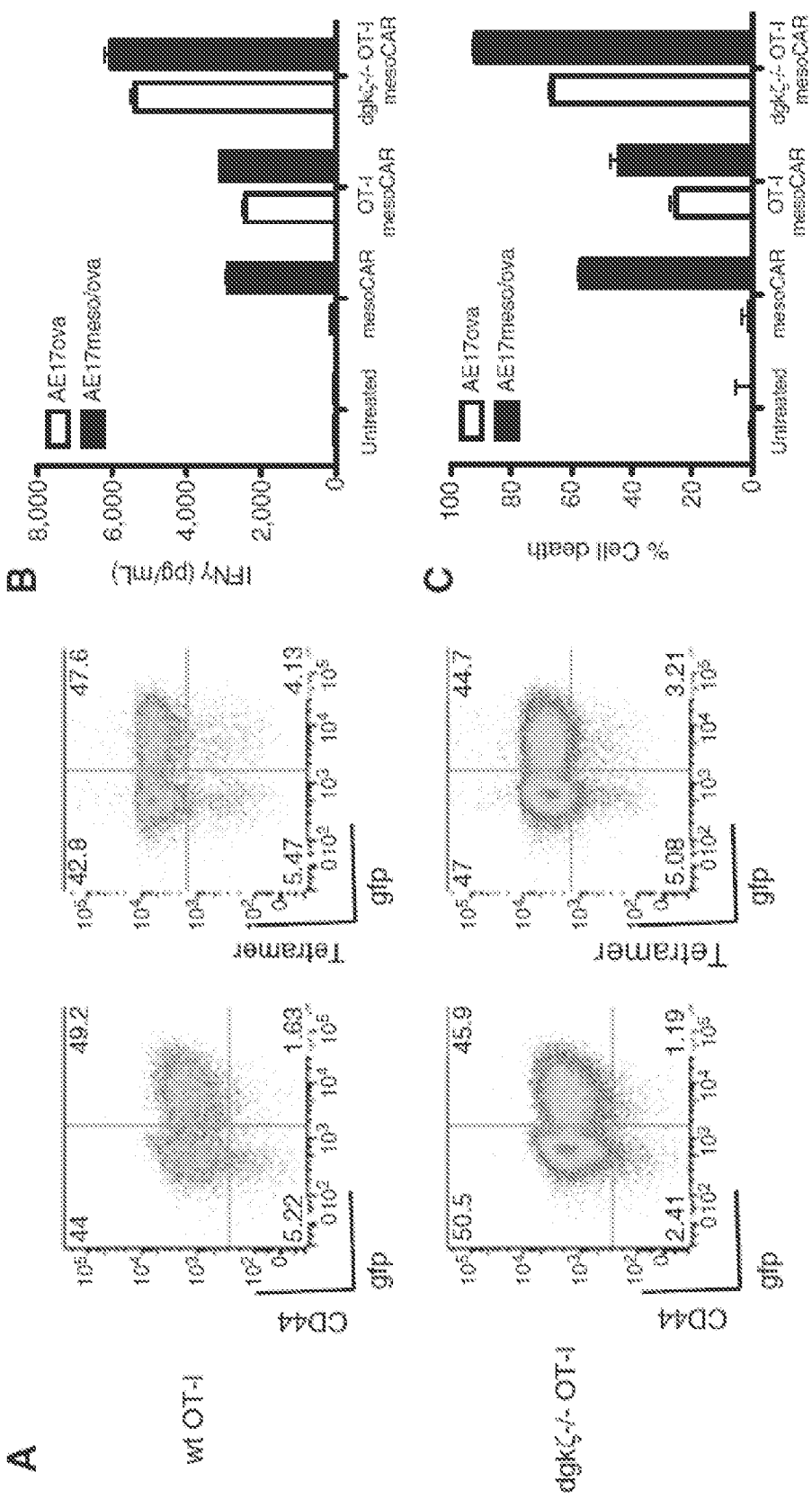
FIG. 17, comprising

Given that deletion of DGK conferred enhanced activity of CD8+ T cells against established tumors but did not seem to be curative, it was examined whether inhibition of DGK function might augment other approaches shown to have efficacy in enhancing T-cell responses against tumor. Therefore, studies were designed to test the impact of DGK deficiency on effector function of CAR-expressing T cells. Experiments first tested whether DGKζ loss would augment functional responses after ligation of CARs, similar to the augmentation of TCR-induced functions that have been shown previously (Zhong et al., 2003, Nat Immunol 4:882-90). For this analysis, mesoCAR was utilized, which is a fusion protein that has high affinity for the human tumor antigen mesothelin, present on human mesothelioma, pancreatic, and ovarian cancer, coupled to the signaling motifs of the TCR CD3ζ chain and the inducible T-cell costimulatory receptor 4-1BB. Wild-type or DGKζ-deficient activated OT-I cells were transduced with mesoCAR-expressing retrovirus, resulting in approximately 50% transduction efficiency (FIG. 17A). Transduction did not affect the activation state of the T cells, as assessed by expression of CD44, or expression of the endogenous TCR, as assessed with tetramer specific for OT-I (FIG. 17A). MesoCAR-transduced DGKζ-deficient and wild-type OT-I cells were then compared in their ability to produce IFNγ and mediate target cell lysis after incubation with AE17ova-meso, a murine cell line engineered to express both ovalbumin and human mesothelin. Transduced OT-I cells lacking DGKζ displayed enhanced IFNγ production and enhanced cytotoxicity after incubation with mesothelioma cell lines (FIG. 17B and FIG. 17C), indicating that deletion of DGKζ enhances the function of CAR-transduced CD8+ T cells against AE17 cells that express both ova and mesothelin.

Figure 18:
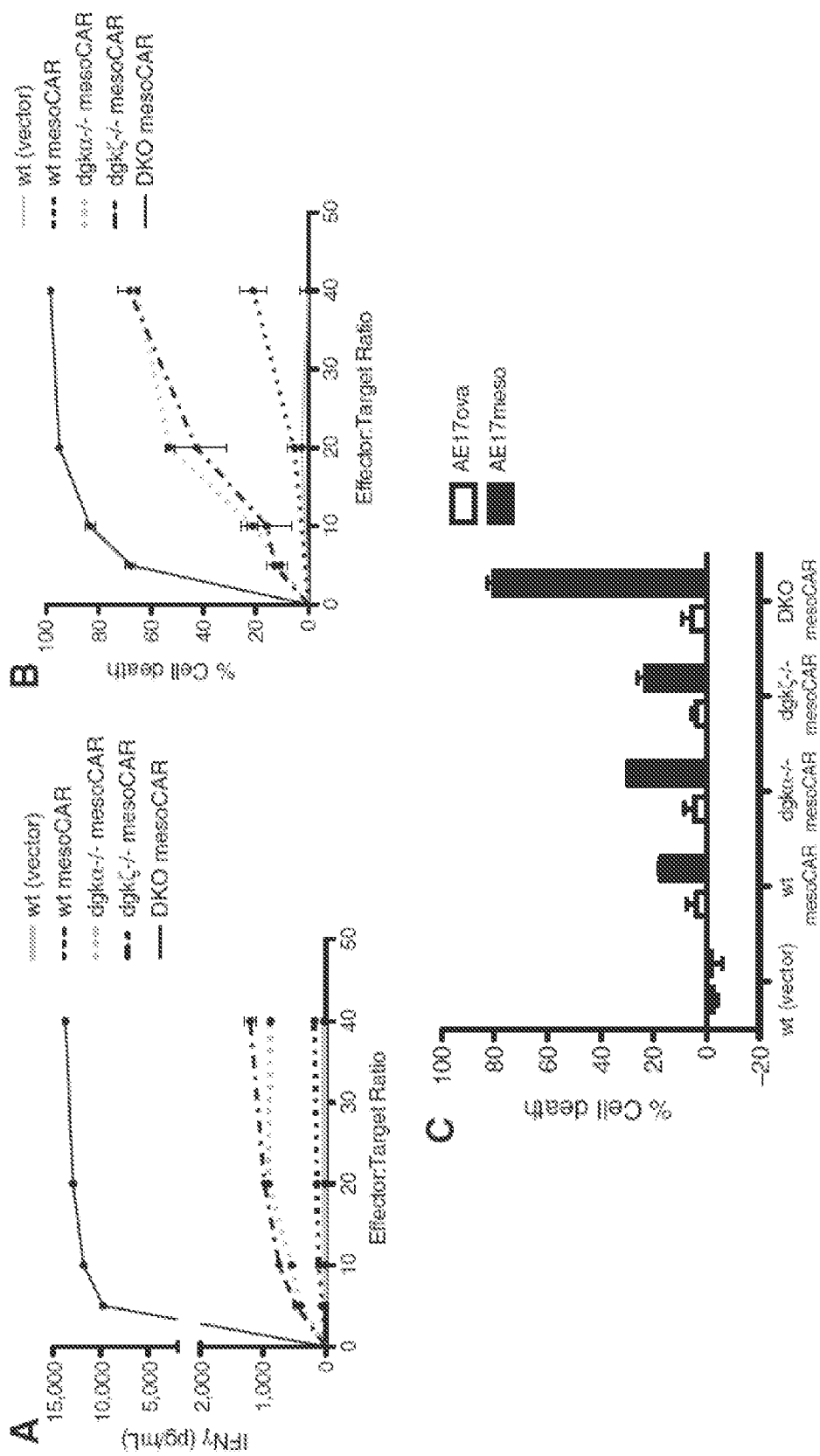
FIG. 18, comprising

Combined Deletion of DGKζ and DGKα Markedly Enhances T-Cell Responses after Stimulation of mesoCAR The finding that deletion of DGKζ enhanced mesoCAR T-cell functional responses suggested that these 2 strategies may be used together for potentiating CD8+ T-cell tumor responses. However, these initial experiments were complicated by the fact that the target cells expressed antigens for both TCR (ovalbumin) and CAR (mesothelin). Thus, to avoid potentially confounding results with ovalbumin-specific TCRs, experiments were conducted in non-TCR transgenic animals. Further, DGKα and DGKζ-deficient mice were intercrossed to generate animals deficient in both DGK isoforms to study CAR-T cells generated from double knockout (DKO) mice. Naïve T cells were isolated from wild-type, dgkα-/-, dgkζ-/-, or DKO mice and infected with retrovirus encoding mesoCAR under high IL-2 concentrations that favored CD8+ T-cell growth (cells were 85% CD8+ T cells at the end of incubation). As observed with deletion of DGK in OT-I cells, deletion of either DGKα or DGKζ in this population of cells expressing the mesoCAR receptor conferred enhanced cytokine production and cytotoxicity when the T cells were incubated with tumor cells expressing mesothelin (FIG. 18A and FIG. 18B). Strikingly, DKO cells showed profoundly enhanced effector functions compared with cells with deletion of either DGK isoform alone or wild-type cells. The enhanced cytotoxicity observed in these cell lines was mesothelin specific because mesoCAR-transduced DKO T cells did not lyse cells AE17 cells expressing an unrelated antigen (AE17ova cells; FIG. 18C).

Figure 19:
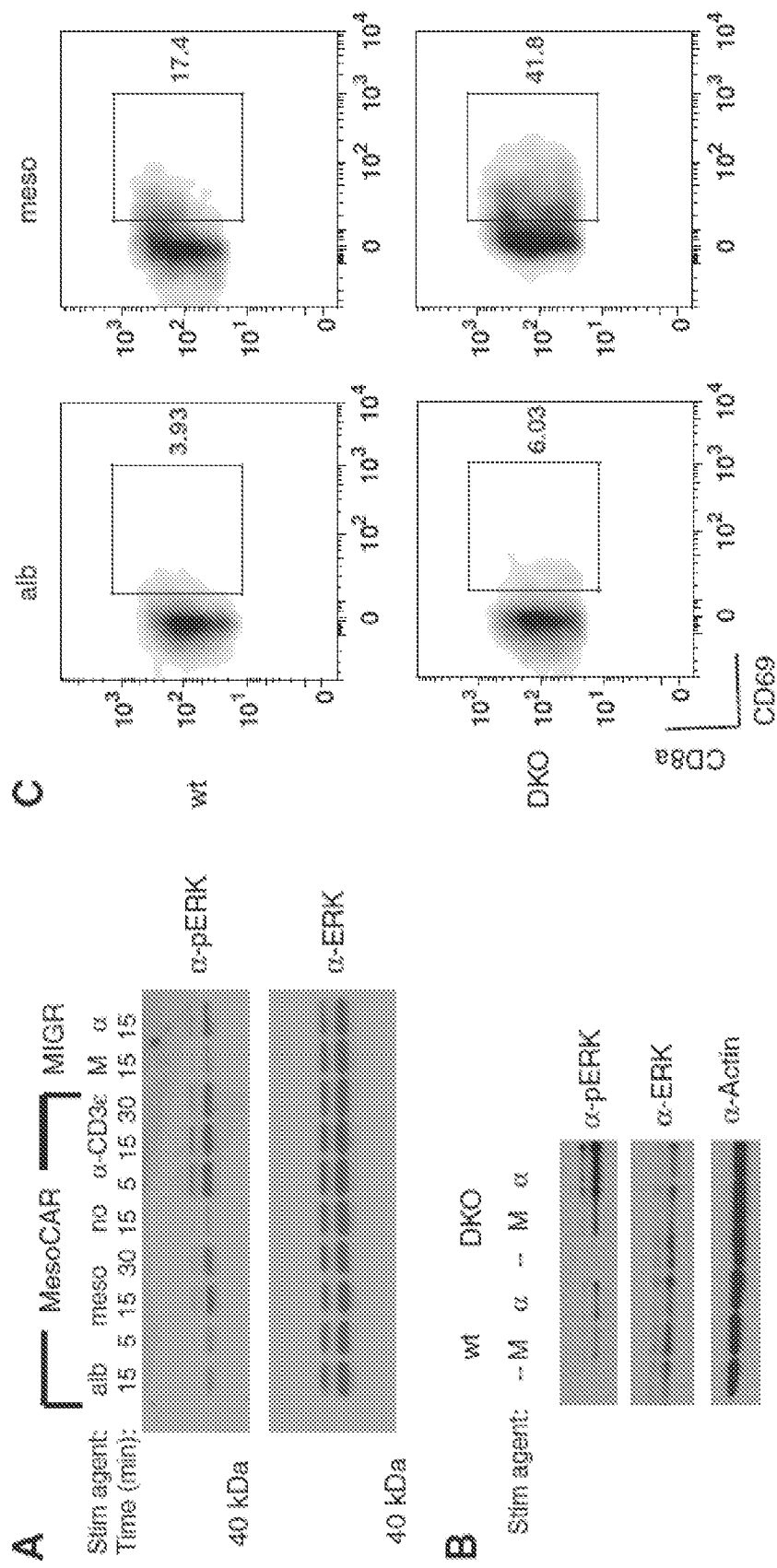
FIG. 19, comprising

It was next evaluated whether the changes in signal transduction that have been previously observed downstream of the TCR in DGK-deficient T cells, for example, enhanced Ras/Erk/AP-1 signaling (Zhong et al., 2003, Nat Immunol 4:882-90; Olenchock et al., 2006, Nat Immunol 7:1174-81), were also present downstream of CAR. To that end, a means to stimulate mesoCAR T cells that did not require mesothelin-expressing cells was developed, because these cells express their own Ras signaling molecules, such as Erk, that could interfere with identifying changes specific to T cells after stimulation. For these studies, tosylactivated beads coated with albumin (as a control) or beads coated with mesothelin were used to stimulate the mesoCAR-expressing cells. Although phosphorylation of Erk was not observed during incubation with control beads, Erk phosphorylation could be readily detected during incubation with mesothelin-coated beads or, as expected, after stimulation of the TCR complex through CD3ε (FIG. 19A). Moreover, activation of Erk by mesothelin beads required expression of mesoCAR because activation of T cells transduced with control retrovirus (MIGR) was not observed (FIG. 19A, right lanes). To test whether deletion of DGKs enhanced Erk activation downstream of mesoCAR, this experiment was then repeated with mesoCAR-transduced T cells derived from DKO mice. Similar to the enhanced activation of Erk known downstream of the TCR in T cells deficient in DGKs, loss of DGKs augmented the activation of Erk downstream of mesoCAR (FIG. 19B). The analysis was extended by investigating the upregulation of CD69 in mesothelin-stimulated wild-type or DKO T cells, as CD69 expression is controlled by activation of the transcription factor AP-1 following Ras/Erk signaling (Zhong et al., 2003, Nat Immunol 4:882-90). Consistent with the biochemical enhancement of Erk activation observed in DKO-transduced T cells, upregulation of CD69 was also increased in mesoCAR DKO T cells compared with wild-type cells (FIG. 19C), confirming a role for DGKs in regulation of this pathway downstream of CAR. Together, these data suggest that DGK influences CAR signaling in a manner similar to the TCR and that the combination of CAR expression and DGK deletion could represent an effective strategy for augmenting CD8+ T-cell antitumor responses.

Figure 20:
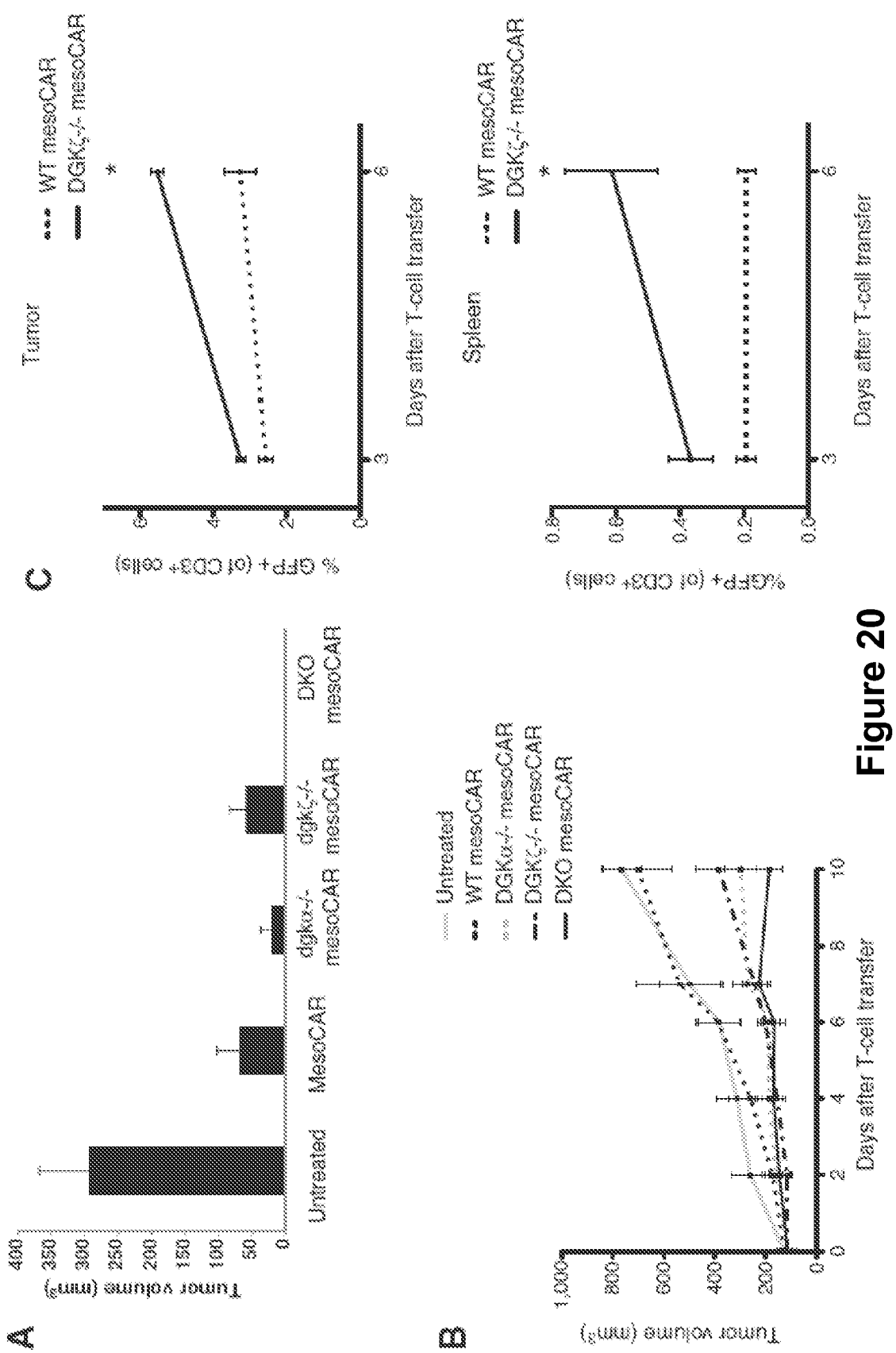
FIG. 20, comprising

Deletion of Both DGKs Enhances Activity of T Cells Downstream of CARs Against Tumor In Vivo It was next sought to determine whether deletion of DGK isoforms conferred enhanced antitumor responses in vivo making use of the WINN assay. For these experiments, mice were injected with a mixture of TC1 meso cells, a murine non-small cell lung cancer line (DeLong et al., 2003, Cancer Res 63:7845-52), along with mesoCAR-expressing wild-type T cells or mesoCAR T cells lacking DGKα, DGK, or both DGK isoforms. Although mice that received wild-type mesoCAR-transduced T cells or T cells lacking a single isoform of DGK were unable to completely control the growth of mesotheliomas, DKO T cells eradicated the mesotheliomas (FIG. 20A), indicating that, as suggested by in vitro studies, targeting DGK generates meaningful enhancement of CD8+ T cells against tumor. Pronounced differences were also noted when AE17meso cells were used as target cells in the WINN assay. Although this experiment offered proof-of-principle that DKO T cells conferred enhanced in vivo activity against mesothelioma, it did not directly assess whether deletion of DGK isoforms would be capable of limiting the growth of established tumors, which is more representative of how CAR-T cells would be used clinically. To that end, AE17meso cells were injected into the flanks of mice, and tumors were allowed to develop to approximately 100 mm$^3$ in size before intravenous administration of CAR-T cells. Under these conditions, although wild-type mesoCAR-transduced T cells were ineffective at limiting tumor growth, mesoCAR-transduced T cells deficient in either DGK isoform significantly ($P<0.05$) decreased the rate of tumor growth (FIG. 20B), an effect increased by the deletion of both DGK isoforms. In addition to enhanced effector function, this effect could, in part, be related to the increased number of DGK-deficient mesoCAR T cells in tumor-bearing mice because quantitative differences in T cells between mesoCAR wild-type and DGK T cells were appreciated 6 days after transfer (FIG. 20C); however, mesoCAR T cells of any genotype were not detected at day 10 or later timepoints under the experimental conditions used.

Inhibition of DGKs Confers Enhanced Antitumor Responses to Human T Cells

Figure 21:
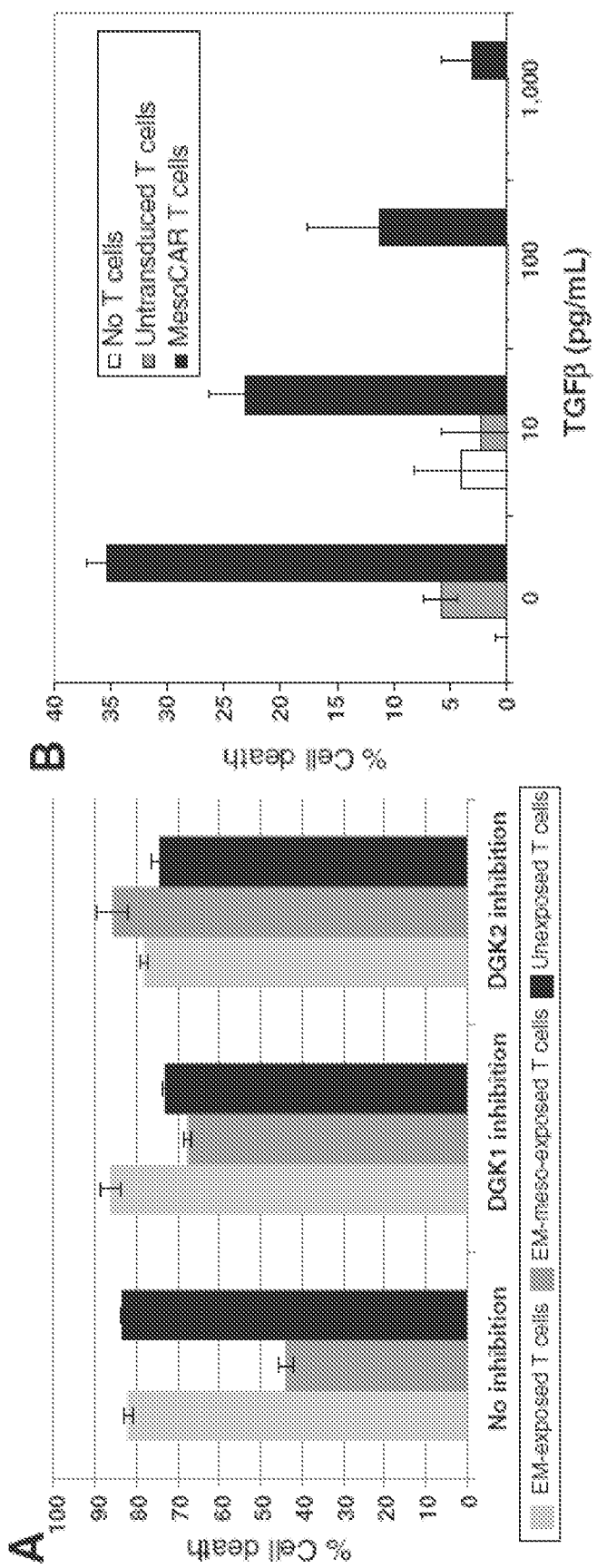
FIG. 21, comprising

Although the demonstration of enhanced mesoCAR function in murine T cells lacking DGK isoforms provides a rationale for targeting DGKs to augment T-cell responses against tumors, an important next step is to establish a role for DGKs in CAR-expressing primary human T cells. Over the course of studies with primary human T cells transduced with mesoCARs, it has been noted that these cells develop reduced functional responsiveness after extended coculture with mesothelin-expressing tumor cells. As shown, 96 hours of coincubation of mesoCAR T cells with EM-meso cells, a mesothelioma line engineered to express high levels of mesothelin, results in significant impairment of mesoCAR T cell lysis of target cells upon reculture (FIG. 21A, left). This effect is reminiscent of various models of antigen-induced anergy, as impaired cytotoxicity is not generated after coculture of mesoCAR T cells with parental EM cells that do not express mesothelin (FIG. 21A). Because it has been previously shown that deletion of DGKs mitigates the induction of anergy (Olenchock et al., 2006, Nat Immunol 7:1174-81; Zha et al., 2006, Nat Immunol 7:1166-73), it was examined whether inhibition of DGKs might also diminish the impaired cytotoxicity observed in the assay. To test this, mesoCAR T cells were incubated with EM-meso cells for 96 hours, and their ability to lyse target cells in the presence of DGK inhibitors R59022 (DGK1 inhibitor) or R59949 (DGK2 inhibitor) was then assessed. It was observed that the addition of either DGK inhibitor was sufficient to reverse the impaired cytotoxicity present in mesothelin-exposed mesoCAR T cells (FIG. 21A, center and right), indicating that, similar to the findings in mice, inhibition of DGK function seems to augment antitumor activity of primary human T cells expressing CARs. These data also suggest that in addition to augmenting TCR (or CAR)-mediated signaling, blockade of DGK enhances T-cell antitumor responses by mitigating antigen-induced unresponsiveness of the effector cells.

DGK-Deficient T Cells Show Reduced Sensitivity to TGFβ

Figure 22:
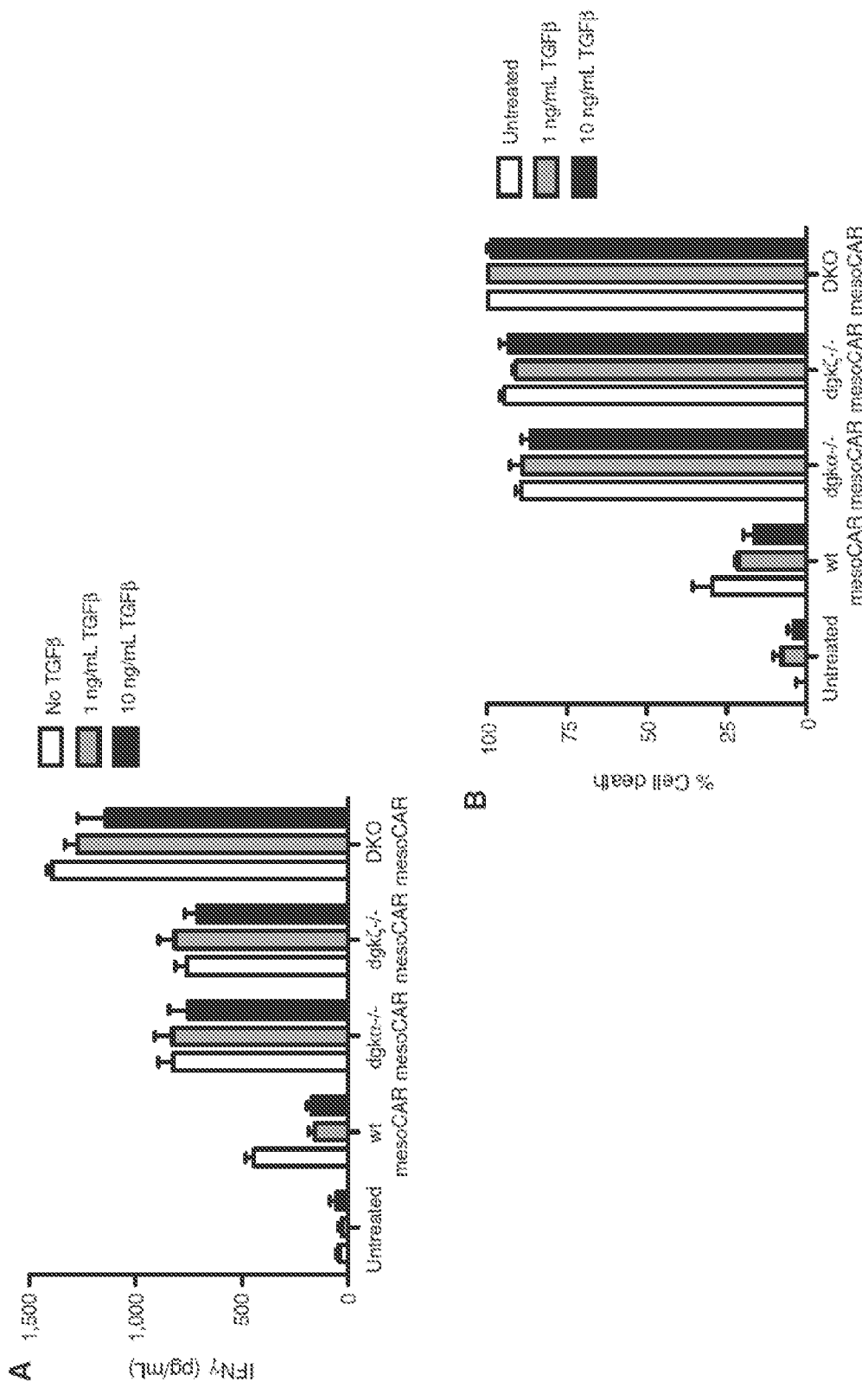
FIG. 22, comprising
Figure 23:
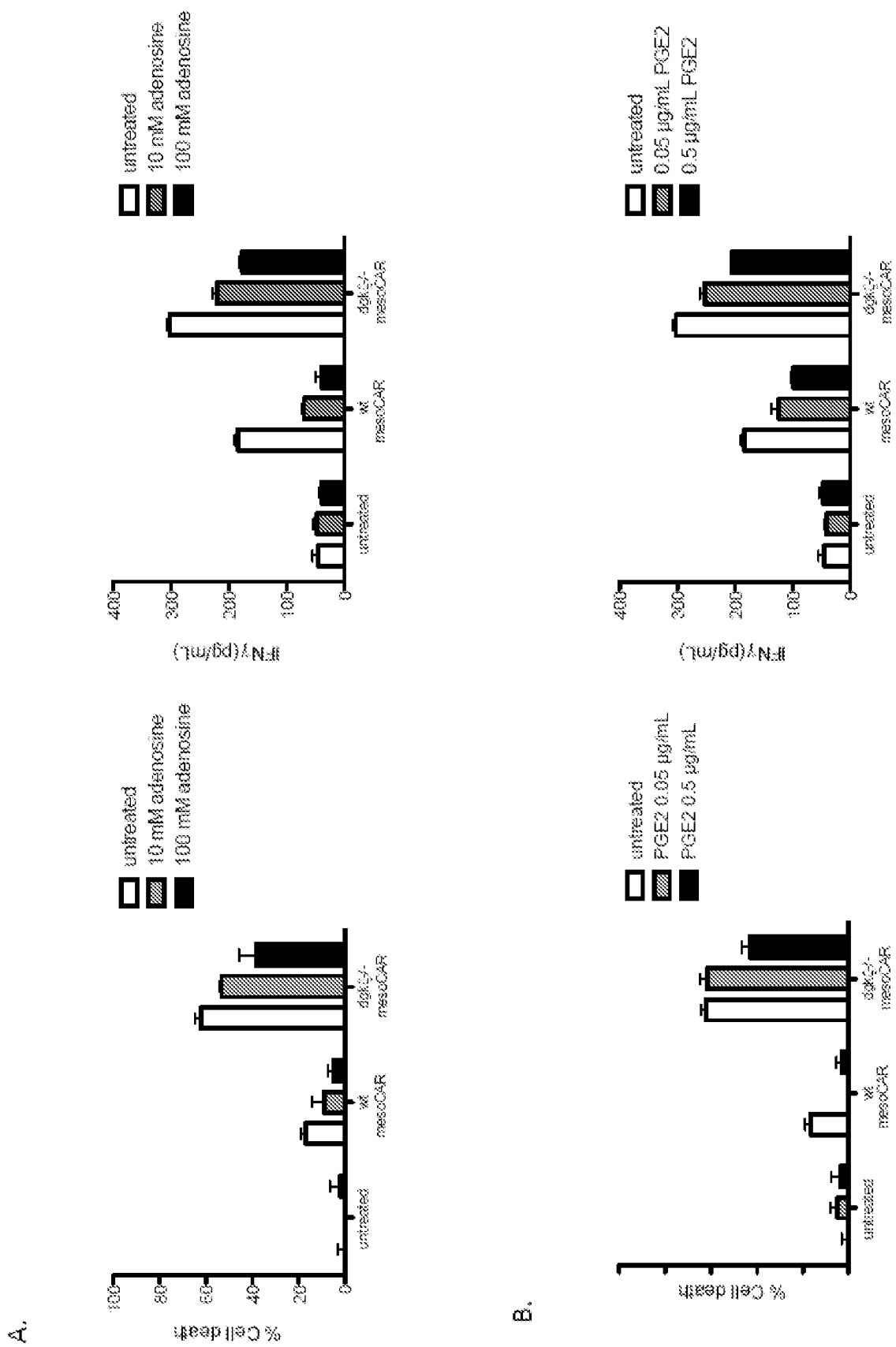
FIG. 23, comprising

Following the observation that inhibition of DGKs reverses the antigen-induced inactivation of CAR-expressing T cells, it was investigated whether deletion of DGK might also reduce sensitivity to other inhibitory influences of T cells. One such inhibitor, TGFβ, is of particular relevance, because secretion of this cytokine by tumor cells has been shown to actively inhibit $CD8^+$ effector T-cell responses against tumors (Flavell et al., 2010, Nat Rev Immunol 10:554-67). Furthermore, TGFβ is speculated to mediate its effects, in part, by dampening the Ras/Erk signal transduction pathway, which is known to be affected by DGKs (Nakamura et al., 2012, Cancer Sci 103:26-33; di Bari, et al., 2009, Cancer Immunol Immunother 58:1809-18). Initially, it was examined whether TGFβ could lead to inhibition of cytotoxicity of human mesoCAR T cells incubated with EM-meso cells. The addition of TGFβ resulted in diminished cytotoxicity by transduced mesoCAR human T cells (FIG. 6B), at levels of TGFβ similar to that present in culture media of EM-meso cells (81.31 µg/mL/24 hours/$10^6$ cells). Next, it was tested whether deletion of DGKs could diminish the effects of TGFβ. Murine mesoCAR T cells replete or deficient in DGKs were incubated with AE17meso cells as described previously, and cytotoxicity and IFNγ production were assessed in the presence or absence of TGFβ. As shown before, deletion of either or both DGK isoforms resulted in mesoCAR T cells with enhanced function when compared with wild-type mesoCAR T cells (FIG. 22A and FIG. 22B, white bars). Addition of TGFβ at lower (1 ng/mL) or higher (10 ng/mL) concentrations of TGFβ were found to reduce cytotoxicity and IFNγ secretion in wild-type mesoCAR T cells; however, these functions were not affected in mesoCAR T cells deficient in either or both DGKs (FIG. 22A and FIG. 22B). These data suggest that deletion of DGKs confers relative resistance to TGFβ for mesoCAR T cells. The finding of relative insensitivity to inhibitory stimuli seems not to be solely restricted to TGFβ because greater functional responses were also observed by DGK-deficient mesoCAR-transduced T cells in the presence of the inhibitory stimuli PGE2 and adenosine (FIG. 23), although to a lesser extent than that observed with TGFβ. Collectively the data presented herein suggest that deletion of DGKs augments effector function of CAR-expressing $CD8^+$ T cells not only by augmenting signaling through the CAR itself but also by reducing sensitivity of the effector cells to physiologically relevant inhibitory signals.

Increased FasL and TRAIL Expression in DGK-Deficient T Cells

Figure 24:
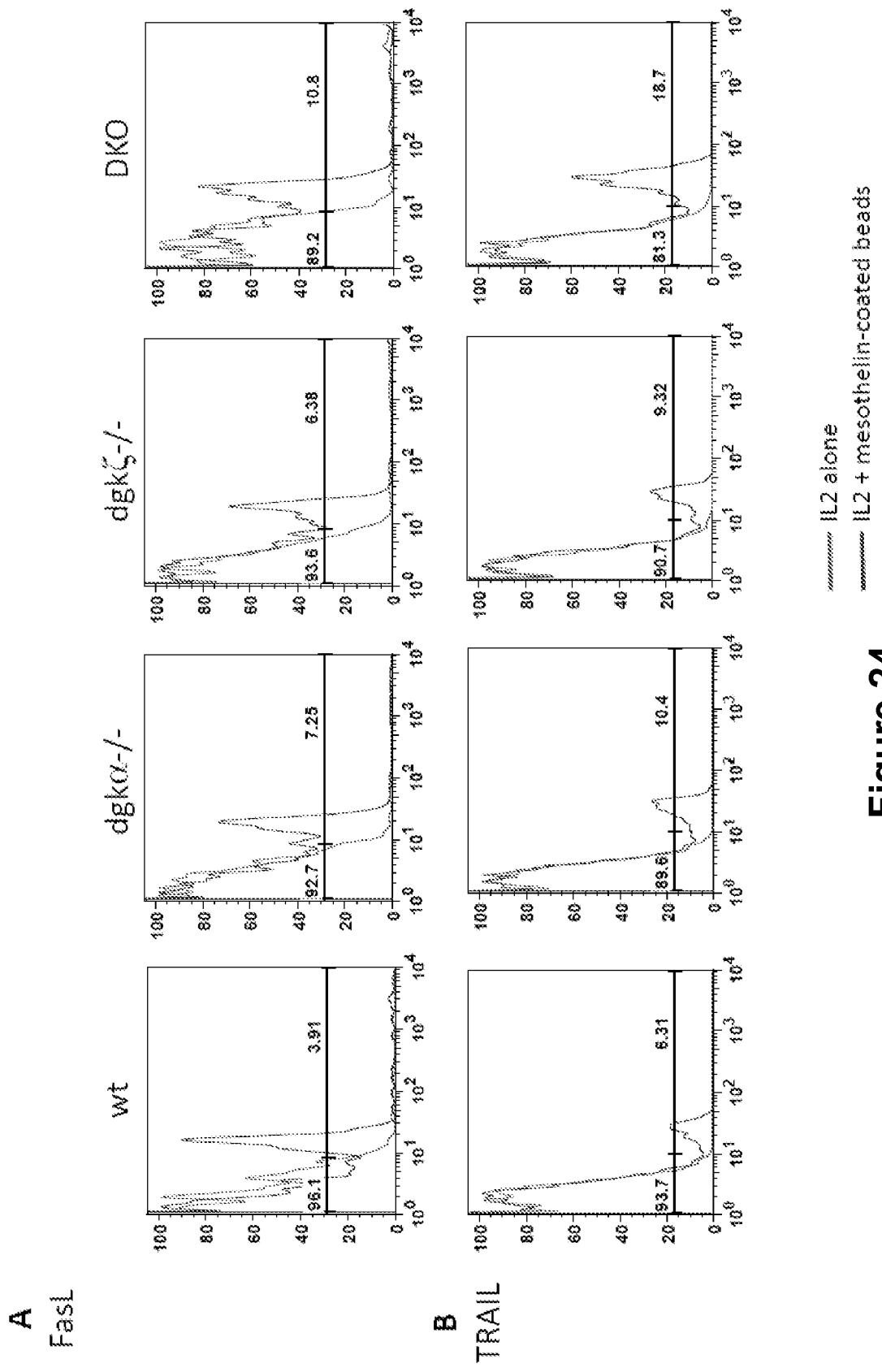
FIG. 24, comprising
Figure 25:
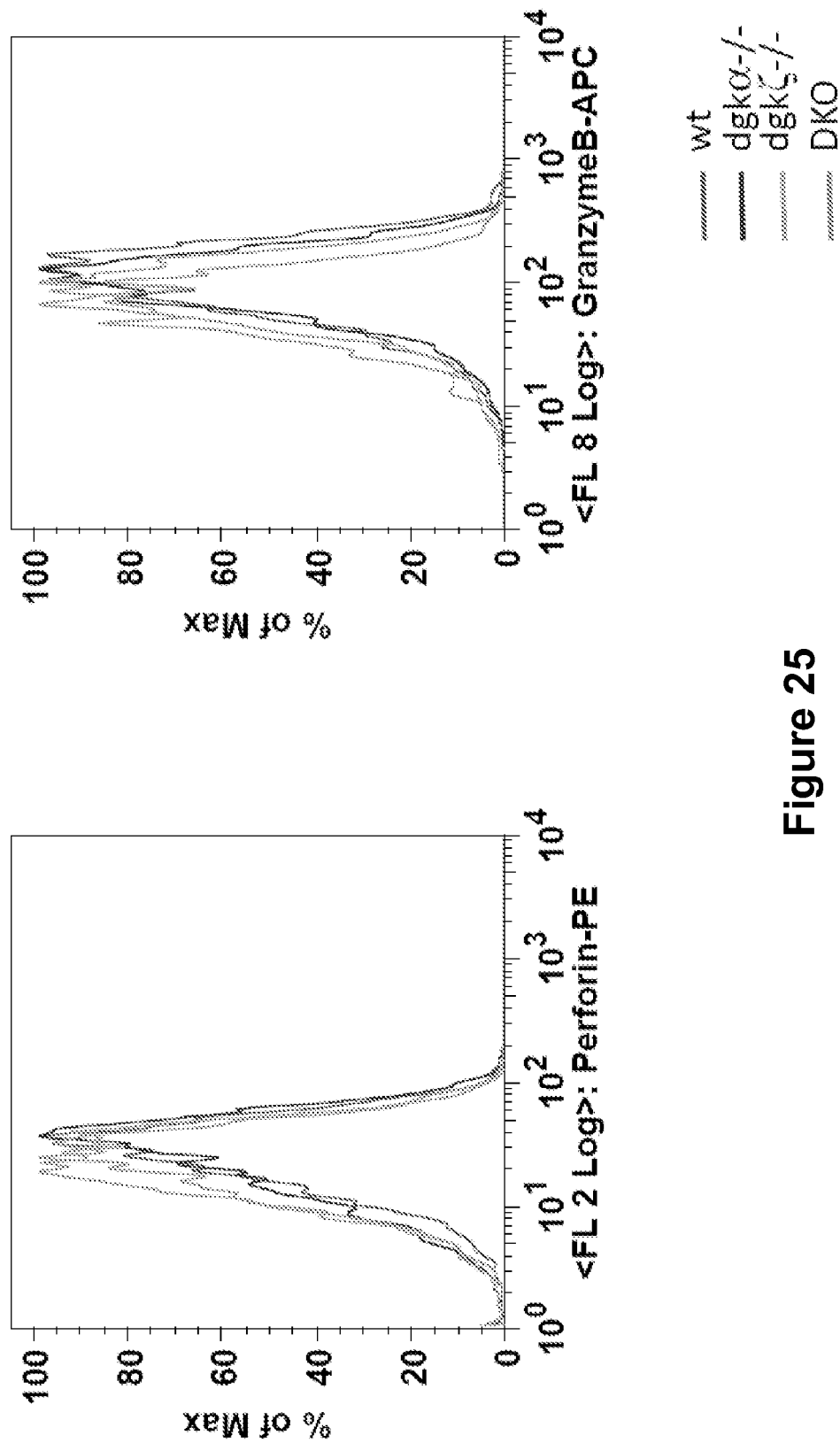
FIG. 25, comprising

Because TGFβ expression suppresses mediators of $CD8^+$ T-cell cytotoxicity (Bedi et al., 2012, Mol Cancer Ther 11:2429-39), such as perforin, granzyme B, FasL, and TRAIL, and because CAR T-cell cytotoxicity is mediated through these effector molecules (Cartellieri et al., 2010, J Biomed Biotechnol 2010:956304), it was examined whether DGK-deficient CAR cells would show greater upregulation of these cytotoxic mediators when compared with wild-type T cells and whether this upregulation may be the basis for the enhanced cytotoxicity observed in DGK-deficient mesoCAR T cells. Wild-type mesoCAR T cells or mesoCAR T cells deficient in one or both DGK isoforms were exposed to mesothelin-coated beads in the presence of IL-2 for 18 hours. Expression of FasL, TRAIL, granzyme B, and perforin were then evaluated by flow cytometry. As predicted, mesoCAR T cells deficient in one or both DGKs showed enhanced expression of the cytotoxic cell surface proteins FasL and TRAIL when compared with wild-type mesoCAR T cells (FIG. 24). In contrast, no difference was observed in the expression of the intracellular cytotoxic proteins granzyme B- or perforin expressing in cells lacking DGKs (FIG. 25). These data suggest that FasL and TRAIL help facilitate the augmented cytotoxicity observed in DGK-deficient mesoCAR T cells.

The Role of DGKs in Limiting the Effector Function of Activated CD8+ T Cells

Current strategies aimed at augmenting T-cell immune responses against malignancy have focused either on assisting the initial activation or priming of naïve T cells, or on potentiating the effects of activated or primed T cells. For instance, antibodies that activate CD40 on APCs upregulate costimulatory molecules that help facilitate priming of naïve cells (Ridge et al., 1998, Nature 393:474-8; Schoenberger et al., 1998, Nature 393:480-3; Bennett et al., 1998, Nature 393:478-80). In contrast, antibodies that block the T-cell inhibitory cell surface molecule CTLA-4 minimally impact naïve T cells but significantly enhance proliferation and effector function of primed T cells (Chambers et al., 1998, Eur J Immunol 28:3137-43; Gajewski et al., 2001, J Immunol 166:3900-7). Inhibition of proteins that negatively regulate signal transduction downstream of the TCR has garnered recent attention as a potential strategy for augmenting T-cell responses to malignancy at the time of T cell priming. For instance, deletion of Casitas-B-lineage lymphoma b (cbl-b), an E3 ubiquitin ligase responsible for the degradation of several proteins important in TCR signal transduction, results in T cells with a decreased requirement of costimulation at the time of activation and enhanced antitumor activity of naïve T cells (Chiang et al., 2007, J Clin Invest 117:1029-36; Loeser et al., 2007, J Exp Med 204:879-91; Stromnes et al., 2010, J Clin Invest 120:3722-34; Wallner et al., 2012, Clin Dev Immunol 2012:692639).

It has been previously shown that, similar to cbl-b, deletion of DGKζ enhanced the effector functions of naïve $CD8^+$ T cells (Riese et al., 2011, J Biol Chem 286:5254-65). Although deletion of cbl-b and DGKζ both results in changes downstream of the TCR, DGKζ, and DGKα, likely act directly to regulate the threshold for activation of T cells downstream of the TCR. Under a currently posited model of TCR signaling, the interplay of 2 Ras-activating proteins, the guanine nucleotide-exchange factors SOS and Ras-GRP1, determine whether the threshold for Ras activation is met within a T cell after TCR engagement, an event required for T-cell activation (Das et al., 2009, Cell 136:337-51). In this model, TCR ligation results in the production of DAG, which binds and activates RasGRP1, and generates small amounts of active Ras. If enough active Ras is generated, it is able to bind an allosteric Ras-binding site on SOS, activating SOS and facilitating generation of most of the active Ras within activated T cells. In a manner largely consistent with this model, it has been previously found that deletion of DGKζ resulted in a decreased threshold of T-cell activation, a finding that correlated with enhanced responses in naïve CD8+ T cells.

In the studies presented herein, it was found that deletion of DGKs also has profound effects on activated T cells. After uniform activation of naïve wild-type or DGKζ-deficient ovalbumin-specific T cells with *Listeria*-ova and then transfer into mice with subcutaneous ovalbumin-expressing EL4 lymphoma, it was found that DGKζ-deficient T cells showed enhanced activity against tumor and increased persistence, both within the spleen and the tumor itself. This finding suggests that alteration of T-cell threshold plays an important role at multiple stages with the T-cell life cycle and identifies DGKζ as a means to simultaneously target both naïve and activated populations of effector T cells.

The role of DGKs in limiting the effector function of activated CD8+ T cells makes DGKs a potential target for CAR-expressing T cells, a strategy gaining traction in the clinical treatment of human malignancies. In current clinical trial protocols, human T cells are transduced with lentivirus-expressing CARs that contain CD3 and CD28 or CD3 and 41BB (CD137), a process that induces T-cell division and activation upon tumor antigen binding (Kalos et al., 2011, Sci Transl Med 3:95ra73). However, it is now clear that additional strategies will be necessary to harness the full potential of CAR-T cells, especially in the treatment of solid malignancies. Although clinical trials in CLL seem promising (Kalos et al., 2011, Sci Transl Med 3:95ra73; Porter et al., 2011, N Engl J Med 365:725-33), earlier works with CAR-transduced T cells in solid malignancies, such as ovarian cancer (Kershaw et al., 2006, Clin Cancer Res 12(20 Pt 1):6106-15) and renal cell carcinoma (Lamers et al., 2006, J Clin Oncol 24:e20-2), were less encouraging, with an absence of objective tumor response and the lack of T-cell persistence. In the studies described here, it was evaluated whether DGKs represent a possible strategy for augmenting CAR-expressing T cells.

After establishing a retroviral system to efficiently transduce murine T cells, it was found, as with TCR signaling, that deletion of DGKζ augmented Erk activation, a phosphorylation event that occurs downstream of DAG formation, after CAR ligation. Deletion of DGK was also found to augment CAR-dependent effector functions because these cells exhibited enhanced cytokine production and target cell killing relative to their wild-type counterparts. Deletion of both T-cell isoforms of DGK resulted in even greater enhancement of effector functions of mesoCAR-transduced cells and resulted in control of tumor in vivo in tumor-bearing mice. These results are encouraging for ongoing clinical trials because murine studies of CAR-transduced T cells have accurately predicted clinical outcomes in past trials (Milone et al., 2009, Mol Ther 17:1453-64; Kalos et al., 2011, Sci Transl Med 3:95ra73; Carpenito et al., 2009, Proc Natl Acad Sci USA 106:3360-5).

Although CARs are uniquely positioned to deal with the limited presence of antigen and costimulation found within the tumor environment, they do not address a third issue relating to T-cell response to tumor: inhibitory stimuli. In these studies, deletion of DGKs was uncovered as a novel strategy for enhancing T-cell activity in the presence of inhibitory stimuli. Specifically, it was found that prolonged exposure to antigen or the tumor microenvironment inhibitors PGE2, adenosine, and TGFβ were less able to suppress CD8+ effector functions in T cells that lacked one or both T-cell isoforms of DGK. TGFβ is thought to be a key mediator of tumor-mediated inhibition because it is secreted by a variety of tumors, and inhibition of TGFβ signaling, through the expression of a dominant negative receptor, results in enhanced tumor-specific activity of cytotoxic lymphocytes (Gorelik & Flavell, 2001, Nat Med 7:1118-22; Bollard et al., 2002, Blood 99:3179-87). In fact, the amount of TGFβ produced by human cancers, such as prostate cancer, inversely correlates to a patient's overall prognosis (Wikström et al., 1998, Prostate 37:19-29; Eastham et al., 1995, Lab Invest 73:628-35). The enhanced Ras activation imparted by the loss of DGKs might explain how DGK-deficient lymphocytes develop insensitivity to TGFβ. Because TGFβ is known to result in the reduced phosphorylation of Itk, a Tec kinase important in PLCγ1 activation (Chen et al., 2003, J Exp Med 197:1689-99), and because PLCγ1 is the protein directly responsible for DAG generation in T cells, one could envision that deletion of DGKs might directly subvert this TGFβ-induced signaling alteration.

It has been shown herein that pharmacologic inhibition of DGKs augment the efficacy of human CAR T cells under inhibitory in vitro conditions. This finding suggests that DGKs play an important role in human T cells and that DGKs may represent attractive clinical targets in augmenting CAR T-cell-based therapies. Model systems in which DGK activity is suppressed through decreased DGK expression (e.g., through expression of shRNA specific for DGKs) or inhibited DGK function (e.g., through expression of dominant negative forms of DGKs) are being developed. Of course, as one develops more potent CAR T cells, issues of toxicity may become relevant. toxicity We could not be assessed in the present model system because the CAR T cells are specific for human mesothelin and do not react with an endogenous mouse protein. However, a second model has been developed using CARs specific for the murine antigen mouse fibroblast activation protein (FAP), an antigen overexpressed on cancer-associated fibroblasts. In initial studies, enhanced antitumor efficacy has been observed using DGKζ-deficient FAP-CAR T cells in tumor-bearing mice, without evidence of enhanced toxicity. One approach that is used when introducing CAR T cells with augmented function is to begin the trial using T cells transduced with short-lived CAR mRNA (Zhao et al., 2010, Cancer Res 70:9053-61), thus mitigating the potential for chronic CAR-induced autoimmunity.

The data presented herein supports the notion that combining CAR expression, which improves targeting of T cells to tumors and drives an initial stimulatory response, with inhibition of proteins known to blunt the effectiveness of the TCR signal may synergize to drive an effector response. The additional value of creating effector T cells resistant to the inhibitory environment generated by the tumor is also likely to contribute to the enhanced efficacy observed in this combined approach. Collectively, the data demonstrates that targeting DGKs, as one means to blunt an endogenous inhibitory response, is a useful mechanism to improve CAR-based strategies in the treatment of human malignancy.

Example 3: Deletion of DGK Enhances Effector Functions and Therapeutic Response of FAP-CAR T Cells that Target Tumor Stroma As presented herein, experiments were conducted utilizing a different CAR targeting a completely different target, fibroblast activation protein (FAP). It is shown that the efficacy of DGKζ-deficient CAR T cells is similarly enhanced as the data using the mesothelin CAR presented elsewhere herein. Fibroblast activation protein is protein expressed on tumor-associated fibroblasts and could be a good target for anti-cancer therapy.

The materials and methods used in these experiments are now described.

Synthesis of Anti-muFAP CAR Constructs

Figure 26:
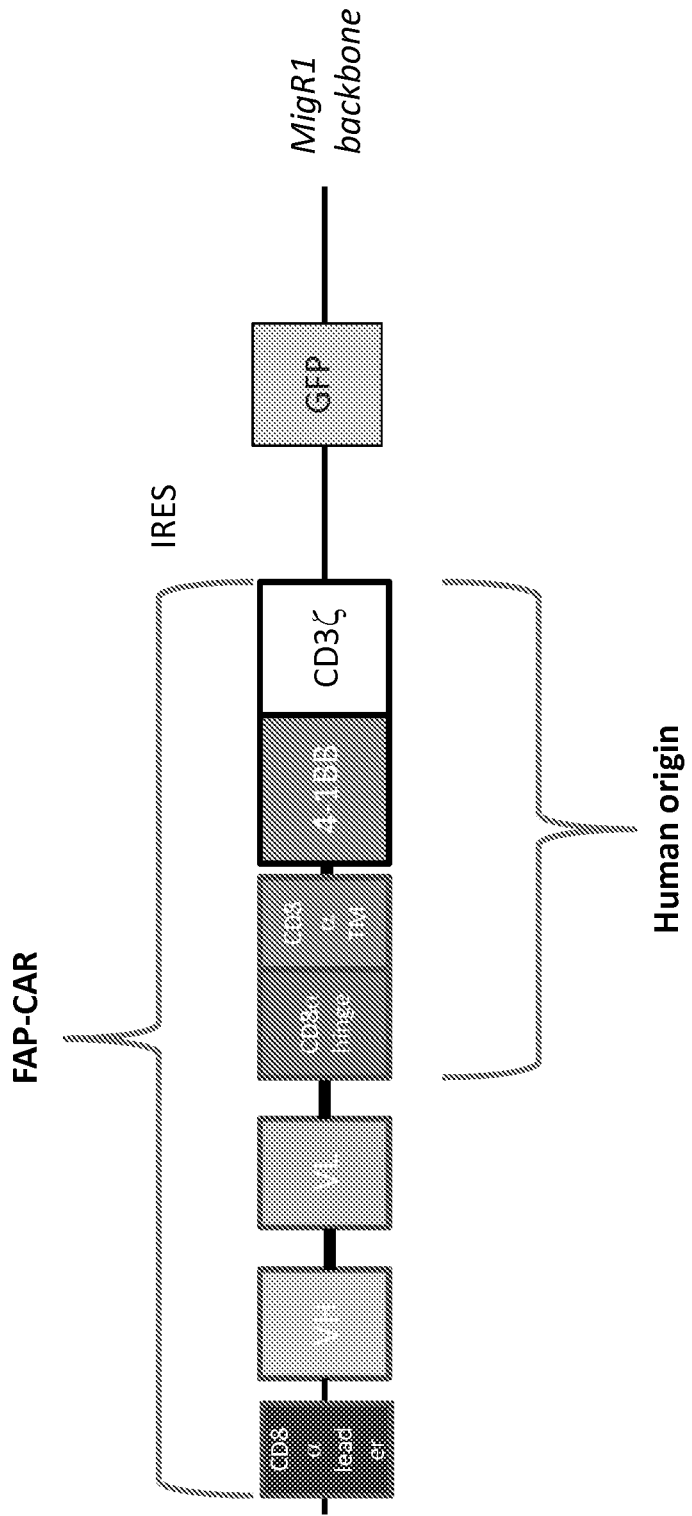
FIG. 26 is a schematic depicting the structure of FAP-CAR. Total RNA of 73.3 hybridoma was extracted, reverse transcribed to cDNA, and PCR amplified and inserted into cloning vector to obtain the sequence of variable domains of IgG heavy and light chains. The anti-muFAP CAR consists of the anti-muFAP scFv, CD8α hinge and transmembrane domain, plus 4-1BB and CD3ζ intracellular signaling domains, and was cloned into MigR1 retroviral vector in order to transduce primary mouse T cells.

Total RNA from 73.3 hybridoma cells was isolated and reverse transcribed to cDNA. Variable heavy ($V_H$) and light ($V_L$) chains of 73.3 anti-muFAP antibody were PCR amplified and sequenced. The $V_H$ and $V_L$ sequences were fused with a CAR construct that is being evaluated in clinical trials (CD8α hinge, CD8α transmembrane domain, and two human intracellular signaling domains derived from 4-1BB and CD3ζ). This CAR was then inserted into a retroviral MigR1 vector (FIG. 26) that also expresses green fluorescent protein (GFP) for tracking purposes (Pear W S et al, 1998, Blood, 92(10): 3780-3792). Infective particles were generated from the supernatants of 293T cells transfected with retroviral vector plasmid and helper plasmids using Lipofectamine 2000 (Invitrogen).

Isolation, Transduction and Expansion of Primary Mouse T Lymphocytes

Primary murine splenic T cells from regular C57BL/6 or DGKζ KO mice were isolated and transduced using the "Pan T cell Negative Selection" kit as suggested by the manufacturer (Miltenyi Biotec), and incubated in 24-well plates ($4 \times 10^6$ cells/well in 2 mL supplemented RPMI-1640 with 100 U/mL IL-2) pre-coated with α-CD3 (1 μg/mL) and α-CD28 (2 μg/mL). After 48 hours, cells ($1 \times 10^6$ cells/well) were mixed with retrovirus (1 mL crude viral supernatant) in a 24-well plate coated with Retronectin (50 μg/mL; Clontech) and centrifuged, without braking, at room temperature for 45 minutes at 1200 g. After overnight incubation, cells were expanded with 50 U/mL of IL-2 for additional 48 hours.

Cytotoxicity and IFNγ ELISA

Parental 3T3 and 3T3.FAP cells were transduced with luciferase as previously described (Moon et al, 2011, Clin Cancer Res, 17: 4719-4730). Cytotoxicity assays were performed by co-culture of T cells with target 3T3 cells at the indicated ratios, in triplicate, in 96-well round bottom plates. After 18 hours, the culture supernatants were collected for IFNγ analysis using an ELISA (mouse IFNγ, BD OpEIA). Cytotoxicity of transduced T cells was determined by detecting the remaining luciferase activity from the cell lysate.

Transfer of CAR-T Cells into Mice Bearing Established Tumors.

Mice were injected subcutaneously with $2 \times 10^6$ AE17.ova (into C57BL/6 mice) tumor cells into the dorsal-lateral flank. Tumor-bearing mice (100 mm³) were then randomly assigned to remain untreated or to receive FAP-CAR T cells with or without DGKζ deletion (minimum, five mice per group, each experiment repeated at least once). $10^7$ T cells were administered through the tail vein. The tumor size were measured by calipers. At the end of the experiment, tumors and spleens were harvested for flow cytometric analyses.

Flow Cytometric Analyses

Tumors were harvested at 11 days after adoptive transfer of FAP-CAR T cells to check for persistence of WT and DGKζ KO FAP-CAR T cells. Cell acquisition was performed on LSR-II using FACSDiva software (BD Bioscience, USA). Data were analyzed using FlowJo (Tree Star).

The results of the experiments are now described.

Figure 27:
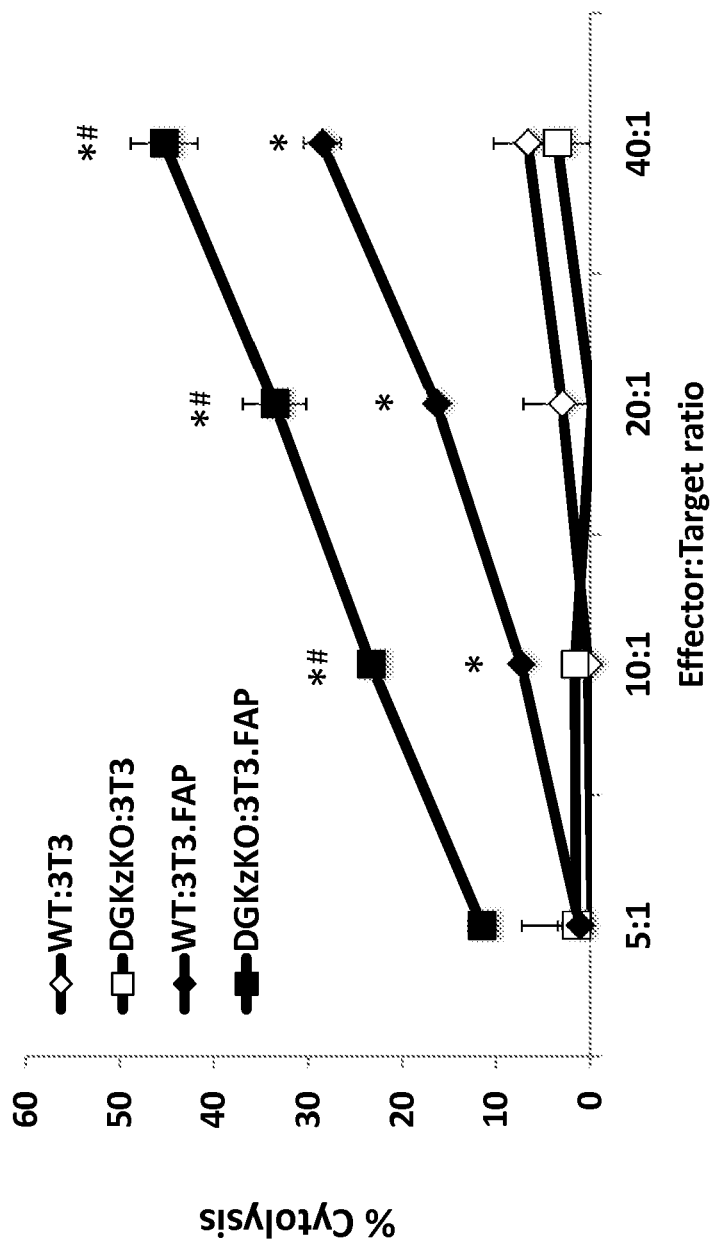
FIG. 27 is a graph depicting the results of experiments demonstrating that deletion of DGKζ enhanced cytolytic activity of FAP-CAR T cells. Splenic T cells were isolated from intact C57BL/6 mice, as well as DGK knockout mice. Isolated T cells were then activated, transduced with FAP-CAR and expanded. A week later, FAP-CAR T cells with or without DGKζ deletion were reacted with 3T3 or 3T3.FAP fibroblasts for 18 hours to determine cytotoxicity. * Denotes statistical significance between untreated and two FAP-CAR-treated samples, p value<0.05.# Denotes statistical significance between WT and DGKζ KO FAP-CAR-treated samples, p value<0.05.
Figure 28:
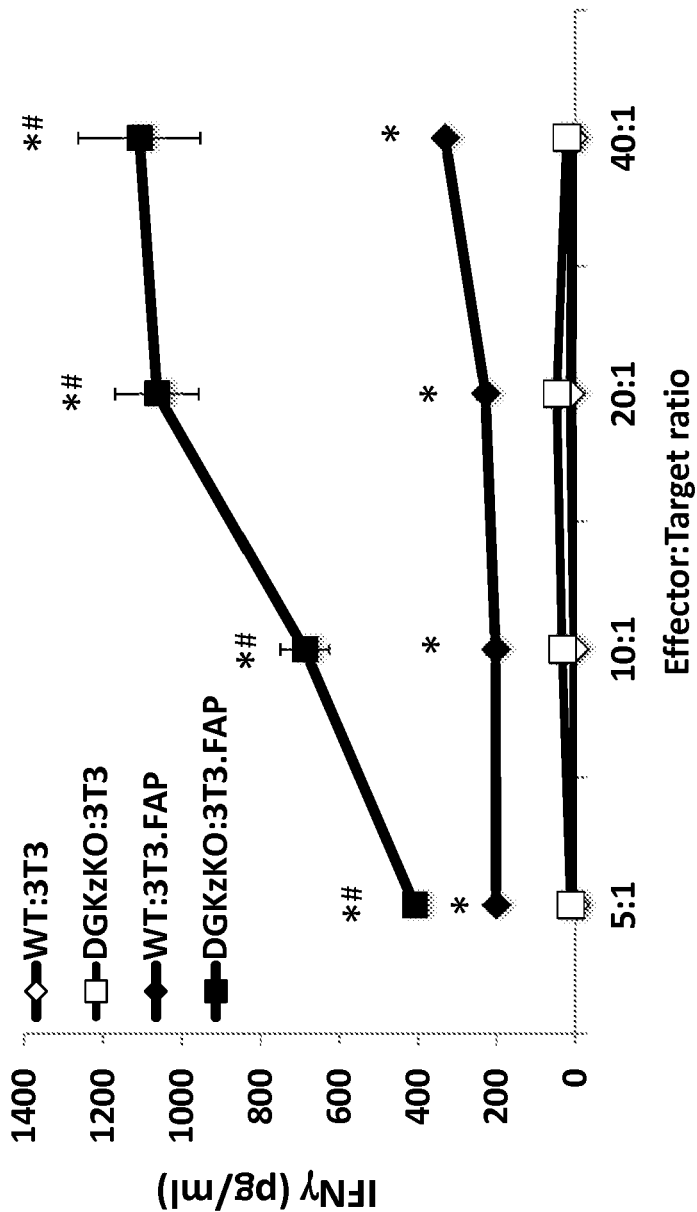
FIG. 28 is a graph depicting the results of experiments demonstrating that deletion of DGKζ enhanced IFNγ of FAP-CAR T cells. Splenic T cells were isolated from intact C57BL/6 mice, as well as DGKζ knockout mice. Isolated T cells were then activated, transduced with FAP-CAR and expanded. A week later, FAP-CAR T cells with or without DGKζ deletion were reacted with 3T3 or 3T3.FAP fibroblasts for 18 hours to determine IFNγ production. * Denotes statistical significance between untreated and two FAP-CAR-treated samples, p value<0.05.# Denotes statistical significance between WT and DGKζ KO FAP-CAR-treated samples, p value<0.05.
Figure 29:
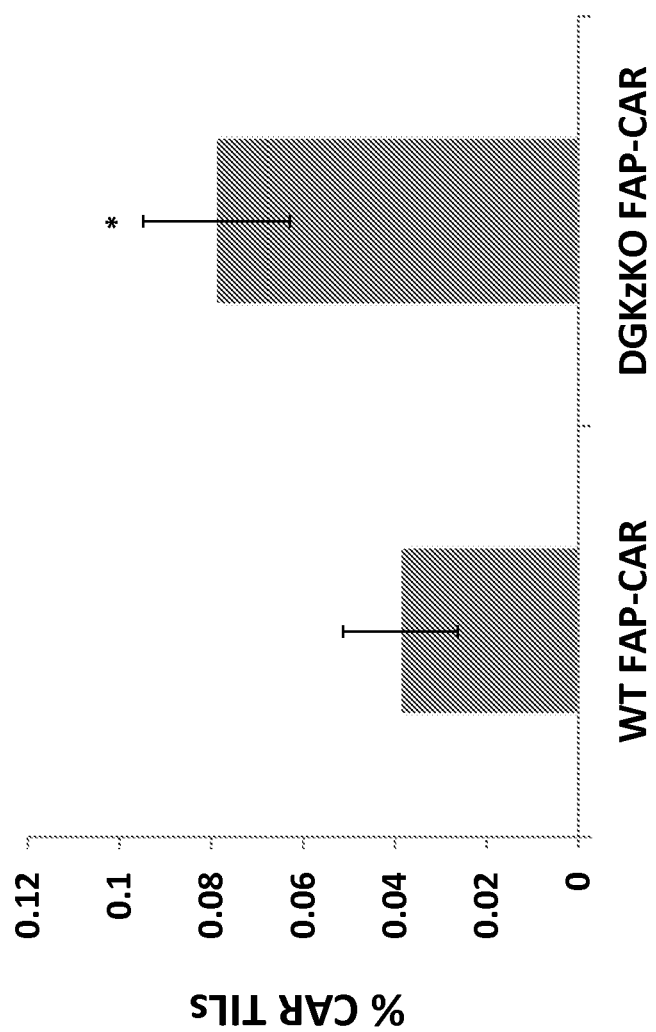
FIG. 29 is a graph depicting the results of experiments demonstrating that DGKζ knockout FAP-T cells persisted longer than wildtype FAP-CAR T cells. AE17.ova tumor mice were adoptively transferred with 10 million wildtype or DGKζ knockout FAP-CAR T cells when tumors reached 100 mm$^3$. Tumors were harvested 11 days post-injection to determine persistence of T cells. Percent FAP-CAR T cells were determined using flow cytometry. * Denotes statistical significance between WT and DGKζ KO FAP-CAR-treated samples, p value<0.05.
Figure 30:
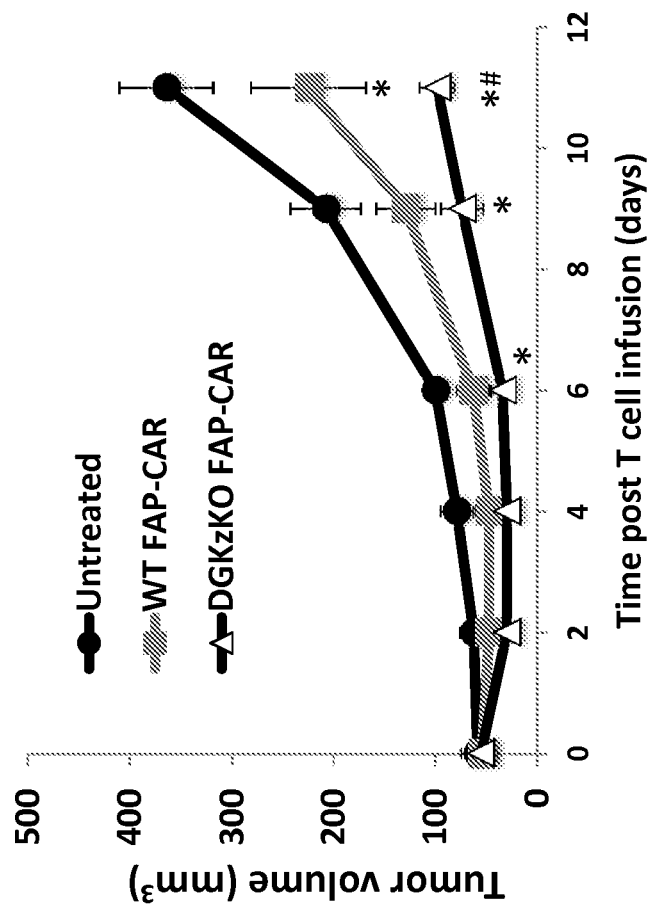
FIG. 30 is a graph depicting the results of experiments demonstrating an enhanced therapeutic response of FAP-CAR T cells conferred by deletion of a negative T cell regulator DGKζ. Mice with AE17.ova flank tumors were injected intravenously with FAP-CAR T cells with or without deletion of DGKζ when tumors were approximately 75 mm$^3$. The tumor measurements were then followed.* Denotes statistical significance between untreated and FAP-CAR-treated samples, p value<0.05.# Denotes statistical significance between single dose FAP-CAR treated group versus DGKζ KO FAP-CAR treated group

As mesothelin-targeted CAR mouse T cells deficient in the inhibitory enzyme diacylglycerol kinase zeta (DGKζ) had enhanced effector functions in vitro and in vivo and increased persistence, the efficacy of comparably transduced FAP-CAR splenic T cells isolated from WT C57BL/6 versus DGKζ-null mice was evaluated. DGKζ knockout FAP-CAR T cells were more efficient in lysing 3T3.FAP cells (FIG. 27) and in secreting more IFNγ (FIG. 28) with retention of specificity in vitro. The DGKζ-deficient FAP-CAR T cells were also more significantly more efficient (p<0.05 on day 11) after being injected into AE17.ova bearing mice (FIG. 29). The increased efficacy was associated with greater persistence of the DGKζ-knockout compared to WT FAP-CAR T cells (GFP+ cells) (FIG. 30). Thus, the enhanced anti-tumor efficacy was likely due to both increased T cell activity and to increased persistence.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. An isolated T cell having enhanced cytolytic activity, wherein the T cell is modified to express a chimeric antigen receptor (CAR), and wherein the T cell is further modified to lack expression of at least one diacylglycerol kinase (DGK) isoform.

2. The isolated T cell of claim 1, wherein the T cell is an activated T cell.

3. The isolated T cell of claim 1, wherein the DGK isoform is selected from the group consisting of DGKα, DGKζ, and both DGKα and DGKζ.

4. The isolated T cell of claim 3, wherein the DGK isoform is both DGKα and DGKζ.

* * * * *